(12) United States Patent
Moon et al.

(10) Patent No.: US 7,470,534 B2
(45) Date of Patent: Dec. 30, 2008

(54) MUTATED AQP, METHOD FOR DETECTING CANCER USING THE SAME, DNA CHIP HAVING OLIGONUCLEOTIDES OF SAID MUTATED AQP SEQUENCE

(75) Inventors: Woo-chul Moon, Seoul (KR); Chul-so Moon, Houston, TX (US); Young-ho Moon, Kwangmyung (KR); Byung-gu Kim, Seoul (KR); Dong-hwan Kim, Kwangmyung (KR); Chan-jae Shin, Seoul (KR); Tae-han Um, Seoul (KR); Hwa-su Kim, Seoul (KR); Mi-kyung Song, Seoul (KR); Hyeung-jae Kim, Kyungsangnamdo (KR); Seok-beom Song, Daejeon (KR)

(73) Assignee: Goodgene, Inc., Sungdong Ku, Seoul (KR)

( * ) Notice: Subject to any disclaimer, the term of this patent is extended or adjusted under 35 U.S.C. 154(b) by 512 days.

(21) Appl. No.: 10/363,925

(22) PCT Filed: Sep. 10, 2001
(Under 37 CFR 1.47)

(86) PCT No.: PCT/KR01/01528
§ 371 (c)(1),
(2), (4) Date: Jan. 5, 2004

(87) PCT Pub. No.: WO02/20787
PCT Pub. Date: Mar. 14, 2002

(65) Prior Publication Data
US 2005/0069872 A1    Mar. 31, 2005

(30) Foreign Application Priority Data
Sep. 9, 2000    (KR) ............................... 2000-53821

(51) Int. Cl.
*C12M 1/34* (2006.01)
*C12M 3/00* (2006.01)
*C07H 21/02* (2006.01)
*C07H 21/04* (2006.01)
*C12Q 1/68* (2006.01)

(52) U.S. Cl. ................. 435/287.2; 536/24.3; 536/24.33
(58) Field of Classification Search ....................... None
See application file for complete search history.

(56) References Cited

U.S. PATENT DOCUMENTS

| 5,302,509 | A  |   | 4/1994  | Cheeseman |
|-----------|----|---|---------|-----------|
| 5,474,796 | A  | * | 12/1995 | Brennan ..................... 427/2.13 |
| 5,741,671 | A  | * | 4/1998  | Agre ........................... 435/69.1 |
| 6,582,908 | B2 | * | 6/2003  | Fodor et al. ..................... 435/6 |

OTHER PUBLICATIONS

Ma et al; Genomics, vol 43, pp. 387-389; 1997.*

Lee et al; Journal of Biological Chemistry, vol 27, pp. 8599-8604, 1996.*
Lemieux et al; Molecular Breeding, vol. 4, 277-289, 1998.*
Genbank Accession No. U46566, U46567, U46568, and U46569; May 1996.*
Ron S. Israeli, Wilson H. Miller, Jr., Sai L. Su, C. Thomas Powell, William R. Fair, Dan S. Samadi, Robert F. Huryk, Anthony Deblasio, Elizabeth T. Edwards, Gilbert J. Wise, and Warren D. W. Heston, Sensitive Nested Reverse Transcription Polymerase Chain Reaction Detection of Circulating Prostatic Tumor Cells: Comparison of Prostate-specific Membrane Antigen and Prostate-specific Antigen-based Assays, Cancer Research, vol. 54, Dec. 15, 1994, pp. 6306-6310.
Early Lung Cancer Detection: Summary and Conclusion, Am. Rev. Respir. Dis., vol. 130, 1984, pp. 565-570.
Chulso Moon, Gregory M. Preston, Constance A. Griffin, Ethylin Wang Jabs, and Peter Agre, The Human Aquaportin-CHIP Gene, Structure,Organization, and Chromosomal Localization, J. Bio. Chem., vol. 268, No. 21, Jul. 25, 1993, pp. 15772-15778.
Landon S. King, Masato Yasui and Petr Agre, Aquaporins in Health and Disease, Molecular Medicine Today, vol. 6, Feb. 2000, pp. 60-65.
Thomas Walz, Teruhisa Hirai, Kazuyoshi Murata, J. Bernard Heymann, Kaoru Mitsuoka, Yoshinori Fujiyoshi, Barbara L. Smith, Peter Agre & Andreas Engel, The Three-Dimensional Structure of Aquaporin-1, Nature, vol. 387, Jun. 5, 1997, pp. 624-627.
Peter Agre, Aquaporin Water Channels in Kidney, J. Am. Soc. Nephrol., vol. 11, 2000; pp. 764-777.
Soren Nielsen, Landon S. King, Birgitte Monster Christensen, and Peter Agre, Aquaporins in Complex Tissues. II. Subcellular Distribution in Respiratory and Glandular Tissues of Rat. Am. J. of Physiol., vol. 273, 1997, pp. C1549-C1561.
Landon S. King, Soren Nielsen, and Peter Agre, Aquaporin-I Water Channel Protein in Lung Ontogeny, Steroid-Induced Expression, and Distribution in Rat, J. Clin. Invest., vol. 97, No. 10, May 1996, pp. 2183-2191.
Stephen C. Case-Green, Kalim U. Mir, Clare E. Pritchard and Edwin M. Southern, Analysing Genetic Information with DNA Arrays, Current Opinion in Chemical Biology, vol. 2, 1998, pp. 404-410.
Bertrand Lemieux, Asaph Aharoni and Mark Schena, Overview of DNA Chip Technology, Molecular Breeding, vol. 4, 1998, pp. 277-289.
C. R. Newton, A. Graham, L. E. Heptinstall, S. J. Powell, C. Summers, N. Kalsheker, J. C. Smith and A. F. Markham, Analysis of Any Point Mutation in DNA. The Amplification Refractory Mutation System (ARMS), Nucleic Acids Research, vol. 17, No. 7, 1989, pp. 2503-2516.
M. Douglas Lee et al., The Human Aquaporin-5 Gene, J. Bio. Chem., vol. 271, No. 15, Apr. 12, 1996, pp. 8599-8604.
Tonghui Ma, Baoxue Yang, Fuminori Umenishi, and A. S. Verkman, Closely Spaced Tandem Arrangement of AQP2, AQP5, and AQP6 Genes in a 27-Kilobase Segment at Chromosome Locus 12q13, Genomics, vol. 43, 1997, pp. 387-389.

(Continued)

Primary Examiner—Jehanne S Sitton
(74) Attorney, Agent, or Firm—Alston & Bird LLP

(57) ABSTRACT

The present invention relates to mutation genes of the AQP (aquaporin), a method for detecting cancer using mutations and expressions of the AQP and a DNA chip possessing oligonucleotides of mutated AQP base sequence. In case of the present method for detecting cancer and DNA chip using the AQP's mutations and expressions, it is highly accurate, rapid and effective in cancer diagnosis.

1 Claim, 76 Drawing Sheets

OTHER PUBLICATIONS

Jun Takenawa, Yoshiyuki Kaneko, Masamichi Kishishita, Hiroaki Higashitsuji, Hiroyuki Nishiyama, Toshiro Terachi, Yoichi Arai, Osamu Yoshida, Manabu Fukumoto and Jun Fujita, Transcript Levels of Aquaporin 1 and Carbonic Anhydrase IV as Predictive Indicators for Prognosis of Renal Cell Carcinoma Patients After Nephrectomy, Int. J. Cancer (Pred. Oncol.), vol. 79, 1998, pp. 1-7.

Yukio Kageyama, Sei Sasaki, Yasuko Yamamura, Hiroyuki Oshima and Yoji Ikawa, Water Channel Protein Subtype Suggests the Origin of Renal Cell Carcinoma, J. Urology, vol. 156, Jul. 1996, pp. 291-295.

Mitsuhiro Endo, Rakesh K. Jain, Brian Witwer, and Dennis Brown, Water Channel (Aquaporin 1) Expression and Distribution in Mammary Carinomas and Glioblastomas, Microvasular Research, vol. 58, 1999, pp. 89-98.

Gerard Evan and Trevor Littlewood, A Matter of Life and Cell Death, Science, vol. 281, Aug. 28, 1998, pp. 1317-1322.

Elizabeth A. Harrington, Abdallah Fanidi and Gerard I. Evan, Oncogenes and Cell Death, Imperial Cancer Research Fund, Current Opinion in Genetics and Development, vol. 4, 1994, pp. 120-129.

Kay MaCleod, Tumor Suppressor Genes, Current Opinion in Genetics & Development, vol. 10, 2000, pp. 81-93.

Peter D. Adams and William G. Kaelin, Jr., Negative Control Elements of the Cell Cycle in Human Tumors, Current Opinion in Cell Biology, vol. 10, 1998, pp. 791-797.

Yoshio Miki, et al., A Strong Candidate for the Breast and Ovarian Cancer Susceptibility Gene BRCA1, Science, vol. 266, Oct. 7, 1994, pp. 66-71.

Richard Wooster, et al., Identification of the Breast Cancer Susceptibility Gene BRCA2, Nature, vol. 378, Dec. 21, 28, 1995, pp. 789-792.

Kenneth W. Kinzler and Bert Vogelstein, Lessons from Hereditary Colorectal Cancer, Cell, vol. 87, Oct. 18, 1996, pp. 159-170.

Arnold J. Levine, p. 53, The Cellular Gatekeeper for Growth and Division, Cell, vol. 88, Feb. 7, 1997, pp. 323-331.

Thomas S. Frank, Laboratory Identification of Hereditary Risk of Breast and Ovarian Cancer, Current Opinion in Biotechnology, vol. 10, 1999, pp. 289-294

Steven A. Ahrendt, Sarel Halachmi, John T. Chow, Li Wu, Naomi Halachmi, Stephen C. Yang, Scott Wehage, Jin Jen, and David Sidransky, Rapid p. 53 Sequence C. Yang, Scott Wehage, Jin Jen, and David Sidransky, Rapid p. 53 Sequence Analysis in Primary Lung Cancer Using An Oligonucleotide Probe Array, Proc. Natl. Acad. Sci. USA, vol. 96, Jun. 1999, pp. 7382-7387.

* cited by examiner

FIG. 20

Sequence of oligo primer by AQP5 base number
(XQ:AQP5, as: antisense, s: sense)

| | |
|---|---|
| XQ-143as | CAGCGTGCCTATGACCAGGCCAAAC |
| XQ-143s  | CCTACCATCCTACAGATCGCGCTGG |
| XQ-144as | CCAGCGTGCCTATGACCAGGCCAAA |
| XQ-144s  | CTACCATCCTACAGATCGCGCTGGC |
| XQ-145as | GCCAGCGTGCCTATGACCAGGCCAA |
| XQ-145s  | TACCATCCTACAGATCGCGCTGGCG |
| XQ-146as | GGCCAGCGTGCCTATAGCCAGGCCA |
| XQ-146s  | ACCATCCTACAGATCGCGCTGGCGT |
| XQ-147as | GGGCCAGCGTGCCTATGGCCAGGCC |
| XQ-147s  | CCATCCTACAGATCGCGCTGGCGTT |
| XQ-148as | TGGGCCAGCGTGCATATGGCCAGGC |
| XQ-148s  | CATCCTACAGATCGCGCTGGCGTTT |
| XQ-149as | CTGTGCCAGCGTGCCTATGGCCAGG |
| XQ-149s  | ATCCTACAGATCGCGCTGGCGTTTG |
| XQ-150as | CCTGGGCCAGCGTGCCTATGGCCAG |
| XQ-150s  | TCCTGCAGATCGCGCTGGCGTTTGG |
| XQ-151as | GCCTGGGCCAGCGTGCCTATAGCCA |
| XQ-151s  | CCTGCAGATCGCGCTGGCGTTTGGC |

FIG. 20 (CONTINUED)

| | |
|---|---|
| XQ-152as | GGCCTGGACCAGCGTGCCTATGGCC |
| XQ-152s | CTGCAGATCGCGCTGGCGTTTGGCC |
| XQ-153as | GGGCCTGGGACAGCGTGCCTATGGC |
| XQ-153s | TGCAGATCGCGCTGGCGTTTGGCCT |
| XQ-154as | AGGGCCTGGGCCAGCGTGCCTATGG |
| XQ-154s | GCAGATCGCGCTGGCGTTTGGCCTG |
| XQ-155as | CAGGGCCTGGGCCAGCGTGCCTATG |
| XQ-155s | CAGATCGCGCTGGCGTTTGGCCTGG |
| XQ-156as | CAAGGGCCTGGGCCAGCGTGCCTAT |
| XQ-156s | AGATCGCGCTGGCGTTTGGCCTGGC |
| XQ-157as | CCAAGGGCCTGGGCCAGCGTGCCTA |
| XQ-157s | GATCGCGCTGGCGTTTGACCTGGCC |
| XQ-158as | TCCAAGGGCCTGGGCCAGCGTGCCT |
| XQ-158s | ATCGCGCTGGCGTTTGTCCTGGCCA |
| XQ-159as | GTCCAAGGGCCTGGGCCAGCGTGCC |
| XQ-159s | TCGCGCTGGCGTTAGGCCTGGCCAT |
| XQ-160as | GGTCCAAGGGCCTGGGCCAGCGTGC |
| XQ-160s | CGCGCTGGCGTTAGGCCTGGCCATA |
| XQ-161as | GGGTCCAAGGGCCTGGGCCAGCGTG |
| XQ-161s | GCGCTGGCGTTAGGCCTGGCCATAG |
| XQ-162as | CGGGTCCAAGGGCCTGGGCCAGCGT |

FIG. 20 (CONTINUED)

| | |
|---|---|
| XQ-162s | CGCTGGCGTTAGGCCTGGCCATAGG |
| XQ-163as | ACGGGTCCAAGGGCCTGGGCCAGCG |
| XQ-163s | GCTGGCGTTTGGCCAGGCCATAGGC |
| XQ-164as | CACGGGTCCAAGGGCCTGGGCCAGC |
| XQ-164s | CTGGCGTTAGGCCTGGCCATAGGCA |
| XQ-165as | TCACGGGTCCAGGGCATGGGCCAG |
| XQ-165s | TGGCGTTAGGCCTGGCCATAGGCAC |
| XQ-166as | CTCACGGGTCCAAGGGCCTGGGCCA |
| XQ-166s | GGCGTTTGGCCTGGCCATAGGCACG |
| XQ-167as | GCTCACGGGTCCAGGGCCTGGGCC |
| XQ-167s | GCGTTTGGCCTGGACATAGGCACGC |
| XQ-168as | CGCTCACGGGTCCAAGGGCCTGGGC |
| XQ-168s | CGTTTGGCCTGGACATAGGCACGCT |
| XQ-169as | CCGCTCACGGGTCACAGGGCCTGGG |
| XQ-169s | GTTTGGCCTGGACATAGGCACGCTG |
| XQ-170as | GCCGCTCACGGGTCCAAGGGCCTGG |
| XQ-170s | TTTGGCCTGGACATAGGCACGCTGG |
| XQ-171as | CGCCGCTCACGGGTCCAAGGGCCTG |
| XQ-171s | TTGGCCTGGACATAGGCACGCTGGC |
| XQ-172as | CCGCCGCTCACGGGTCCCAGGGCCT |

FIG. 20 (CONTINUED)

| | |
|---|---|
| XQ-172s | TGGCCTCGCCATAGGCACGCTGGCC |
| XQ-173as | GCCGCCGCTCACGGGTCCCAGGGCC |
| XQ-173s | GGCCTGGACATAGGCACGCTGGCCC |
| XQ-174as | GGCCGCCGCTCACGGGTCCCAGGGC |
| XQ-174s | GCCTGGACATAGGCACGCTGGCCCA |
| XQ-175as | TGGCCGCCGCTCACGGGTCCCAGGG |
| XQ-175s | CCTGGCCATAGGCACGCTGGCCCAG |
| XQ-176as | GTGGCCGCCGCTCACGGGTCCCAGG |
| XQ-176s | CTGGACATAGGCACGCTGGCCCAGG |
| XQ-177as | TGTGGCCGCCGCTCACGGGTCCCAG |
| XQ-177s | TGGACATAGGCACGCTGGCCCAGGC |
| XQ-178as | ATGTGGCCGCCGCTCACGGGTCCCA |
| XQ-178s | GGCCATAGGCACGCTGACCCAGGCC |
| XQ-179as | GATGTGGCCGCCGCTCACGGGTCCC |
| XQ-179s | GCCATAGGCACGCTGGCCCAGGCCC |
| XQ-180as | TGATGTGGCCGCCGCTCACGGGTCC |
| XQ-180s | CCATAGGCACGCTGGCCCAGGCCCT |
| XQ-181as | TTGATGTGGCCGCCGCTCACGGGTC |
| XQ-181s | CATAGGCACGCTGGCCCTGGCCCTG |
| XQ-182as | GTTGATGTGGCCGCCGCTCACGGGT |
| XQ-182s | ATAGGCACGCTGGCACAGGCCCTGG |

FIG. 20 (CONTINUED)

| | |
|---|---|
| XQ-183as | GGTTGATGTGGCCGCCGCTCACGGG |
| XQ-183s | TAGGCACGCTGGCACAGGCCCTGGG |
| XQ-184as | GGGTTGATGTGGCCGCCGCTCACGG |
| XQ-184s | AGGCACGCTGGCACAGGCCCTGGGA |
| XQ-185as | GGGGTTGATGTGGCCGCCGCTCACG |
| XQ-185s | GGCACGCTGGCACAGGCCCTGGGAC |
| XQ-186as | CGGGGTTGATGTGGCCGCCGCTCAC |
| XQ-186s | GCACGCTGGCACAGGCCCTGGGACC |
| XQ-187as | GCGGGGTTGATGTGGCCGCCGCTCA |
| XQ-187s | CACGCTGGCACAGGCCCTGGGACCC |
| XQ-188as | GGAGGGGTTGATGTGGCCGCCGCTC |
| XQ-188s | ACGCTGGCACAGGCCCTGGGACCCG |
| XQ-189as | TGGAGGGGTTGATGTGGCCGCCGCT |
| XQ-189s | CGCTGGCACAGGCCCTGGGACCCGT |
| XQ-190as | ATGGAGGGGTTGATGTGGCCGCCGC |
| XQ-190s | GCTGGCCAAGGCCCTGGGACCCGTG |
| XQ-191as | GATGGAGGGGTTGATGTGGCCGCCG |
| XQ-191s | CTGGCCAAGGCCCTGGGACCCGTGA |
| XQ-192as | TGATGACGGGGTTGATGTGGCCGCC |
| XQ-192s | TGGCCAAGGCCCTGGGACCCGTGAG |
| XQ-193as | GTGATGGAGGGGTTGATGTGGCCGC |

FIG. 20 (CONTINUED)

| | |
|---|---|
| XQ-193s | GGCCAAGGCCCTGGGACCCGTGAGC |
| XQ-194as | GGTGATGGCGGGGTTGATGTGGCCG |
| XQ-194s | GCCAAGGCCCTGGGACCCGTGAGCG |
| XQ-195as | GGGTGATGGCGGGGTTGATGTGGCC |
| XQ-195s | CCAAGGCCCTGGGACCCGTGAGCGG |
| XQ-196as | AGGGTGATGGCGGGGTTGATGTGGC |
| XQ-196s | CAAGGCCCTGGGACCCGTGAGCGGC |
| XQ-197as | CAGGGTGATGGCGGGGTTGATGTGG |
| XQ-197s | CAGGCCCTGGGACCCGTGAGCGGCG |
| XQ-198as | CCAGGGTGATGGCGGGGTTGATGTG |
| XQ-198s | AGGCCCTGGGACCCGTGAGCGGCGG |
| XQ-199as | GCCAGGGTGATGGCGGGGTTGATGT |
| XQ-199s | GGCCCTGGGACCCGTGAGCGGCGGC |
| XQ-200as | GGCCAGGGTGATGGCGGGGTTGATG |
| XQ-200s | GCCCTGGGACCCGTGAGCGGCGGCC |
| XQ-201as | GGGCCAGGGTGATGGCGGGGTTGAT |
| XQ-201s | CCCTGGGACCCGTGAGCGGCGGCCA |
| XQ-202as | AGGGCCAGGGTGATGGCGGGGTTGA |
| XQ-202s | CCTGGGACCCGTGAGCGGCGGCCAC |
| XQ-203as | GAGGGCCAGGGTGATGGCGGGGTTG |
| XQ-203s | CTGGGACCCGTGAGCGGCGGCCACA |

FIG. 20 (CONTINUED)

| | |
|---|---|
| XQ-204as | AGAGGGCCAGGGTGATGGCGGGGTT |
| XQ-204s  | TGGGACCCGTGAGCGGCGGCCACAT |
| XQ-205as | AAGAGGGCCAGGGTGATGGCGGGGT |
| XQ-205s  | GGGACCCGTGAGCGGCGGCCACATC |
| XQ-206as | CAAGAGGGCCAGGGTGATGGCGGGG |
| XQ-206s  | GGACCCGTGAGCGGCGGCCACATCA |
| XQ-207as | CCAAGAGGGCCAGGGTGATGGCGGG |
| XQ-207s  | GACCCGTGAGCGGCGGCCACATCAA |
| XQ-208as | ACCAAGAGGGCCAGGGTGATGGCGG |
| XQ-208s  | ACCCGTGAGCGGCGGCCACATCAAC |
| XQ-209as | CACCAAGAGGGCCAGGGTGATGGCG |
| XQ-209s  | CCCGTGAGCGGCGGCCACATCAACC |
| XQ-210as | CCACCAAGAGGGACAGGGTGATGGC |
| XQ-210s  | CCGTGAGCGGCGGCCACATCAACCC |
| XQ-211as | CCCACCAAGAGGGCCAGGGTGATGG |
| XQ-211s  | CGTGAGCGGCGGCCACATCAACCCC |
| XQ-212as | GCCCACCAAGAGGGCCAGGGTGATG |
| XQ-212s  | GTGAGCGGCGGCCACATCAACCCCG |

FIG. 20 (CONTINUED)

| | |
|---|---|
| XQ-213as | TGCCCACCAAGAGGGCCAGGGTGAT |
| XQ-213s | TGAGCGCCGGCCACATCAACCCCGC |
| XQ-214as | TTGCCCACCAAGAGGGCCAGGGTGA |
| XQ-214s | GAGCGACGGCCACATCAACCCCGCC |
| XQ-215as | GTTGCCAACCAAGAGGGCCAGGGTG |
| XQ-215s | AGCGGAGGCCACATCAACCCCGCCA |
| XQ-216as | GGTTGCCCACCAAGAGGGCCAGGGT |
| XQ-216s | GCGGAGGCCACATCAACCCCGCCAT |
| XQ-217as | TGGTTGCCCACCAAGAGGGCCAGGG |
| XQ-217s | CGGAGGCCACATCAACCCCGCCATC |
| XQ-218as | CTGGTTGCCCACCAAGAGGGCCAGG |
| XQ-218s | GGAGGCCACATCAACCCCGCCATCA |
| XQ-219as | TATGGTTGCCCACCAAGAGGGCCAG |
| XQ-219s | GCGGCCACATCAACCCCGCCATCAC |
| XQ-220as | ATCTGGTTGCCCACCAAGAGGGCCA |
| XQ-220s | CGGCCACATCAACCCCGCCATCACC |
| XQ-221as | GATCTGGTTGCCCACCAAGAGGGCC |

FIG. 20 (CONTINUED)

| | |
|---|---|
| XQ-221s | GGCCACATCAACCCCGCCATCACCC |
| XQ-222as | AGATCTGGTTGACCACCAAGAGGGC |
| XQ-222s | GCCACATCAACCCCGCCATCACCCT |
| XQ-223as | GAGATCTGGTTGCCCACCAAGAGGG |
| XQ-223s | CCACATCAACCCCGCCATCACCCTG |
| XQ-224as | CGAGATCTGGTTGCCCACCAAGAGG |
| XQ-224s | CACATCAACCCCGCCATCACCCTGG |
| XQ-225as | GCGAGATCTGGTTGCCCACCAAGAG |
| XQ-225s | ACATCAACCCCGACATCACCCTGGC |
| XQ-226as | AGCGAGATCTGGTTGCCCACCAAGA |
| XQ-226s | CATCAACCCCGCCATCACCCTGGCC |
| XQ-227as | CAGCGAGATCTGGTTGCCCACCAAG |
| XQ-227s | ATCAACCCCGCCATCACCCTGGCCC |
| XQ-228as | GCAGCGAGATCTGGTTGCCCACCAA |
| XQ-228s | TCAACCCCGCCATCACCCTGGCCCT |
| XQ-229as | AGCAGCGAGATCTAGTTGCCCACCA |
| XQ-229s | CAACCCCGCCATCACCCTGGCCCTC |

FIG. 20 (CONTINUED)

| | |
|---|---|
| XQ-230as | GAGCAGCGAGATCTGGTTGCCCACC |
| XQ-230s  | AACCCGCCATCACCCTGGCCCTCT |
| XQ-231as | GGAGCAGCGAGATCTGGTTGCCCAC |
| XQ-231s  | ACCCCGCCATCACCCTGGCCCTCTT |
| XQ-232as | CGGAGCAGCGAGATCTGGTTGCCCA |
| XQ-232s  | CCCCGCCATCACCCTGGCCCTCTTG |
| XQ-233as | CCGGAGCAGCGAGATCTGGTTGCCC |
| XQ-233s  | CCCGCCATCACCCTGGCCCTCTTGG |
| XQ-234as | CCCGGAGCAGCGAGATCTGGTTGCC |
| XQ-234s  | CCGCCATCACCCTGGCCCTCTTGGT |
| XQ-235as | GCCCGGAGCAGCGAGATCTGGTTGC |
| XQ-235s  | CGCCATAACCCTGGCCCTCTTGGTG |
| XQ-236as | AGCCCGGAGCAGCGAGATCTGGTTG |
| XQ-236s  | GCCATCACCCTGGCCCTCTTGGTGG |
| XQ-237as | AAGCCCGGAGCAGCGAGATCTGGTT |
| XQ-237s  | CCATCACCCTGGCCCTCTTGGTGGG |
| XQ-238as | AAAGCCCGGAGCAGCGAGATCTGGT |

FIG. 20 (CONTINUED)

| | |
|---|---|
| XQ-238s | CATCACCCTGGACCTCTTGGTGGGC |
| XQ-239as | GAAAGCCCGGAGCAGCGAGATCTGG |
| XQ-239s | ATCACCCTGGCCCTCTTGGTGGGCA |
| XQ-240as | AGAAAGCCCGGAGCAGCGAGATCTG |
| XQ-240s | TCACCCTGGCCCTCTTGGTGGGCAA |
| XQ-241as | AAGAAAGCCCGGAGCAGCGAGATCT |
| XQ-241s | CACCCTGGCCCTCTTGGTGGGCAAC |
| XQ-242as | GAAGAAAGCCCGGAGCAGCGAGATC |
| XQ-242s | ACCCTGGCCCTCTTGGTGGGCAACC |
| XQ-243as | AGAAGAAAGCCCGGAGCAGCGAGAT |
| XQ-243s | CCCTGGCCCTCTTAGTGGGCAACCA |
| XQ-244as | TAGAAGAAAGCCCGGAGCAGCGAGA |
| XQ-244s | CATGGCCCTCTTGGTGGGCAACCAG |
| XQ-245as | GTAGAAGAAAGCCCGGAGCAGCGAG |
| XQ-245s | CTGGCCCTCTTGGTGGGCAACCAGA |
| XQ-246as | CGTAGAAGAAAGCCCGGAGCAGCGA |
| XQ-246s | TGGCCCTCTTGGTGGGCAACCAGAT |

FIG. 20 (CONTINUED)

| | |
|---|---|
| XQ-247as | ACGTAGAAGAAAGCCCGGAGCAGCG |
| XQ-247s  | GGCCCTCTTGGTGGGCAACCAGATC |
| XQ-248as | CACGTAGAAGAAAGCCCGGAGCAGC |
| XQ-248s  | GCCCTCTTGGTGGGCAACCAGATCT |
| XQ-249as | CCACGTAGAAGAAAGCCCGGAGCAG |
| XQ-249s  | CCCTCTTGGTGGGCAACCAGATCTC |
| XQ-250as | GCCACGTAGAAGAAAGCCCGGAGCA |
| XQ-250s  | CCTCTTGGTGGGCAACCAGATCTCG |
| XQ-251as | CGCCACGTAGAAGAAAGCCCGGAGC |
| XQ-251s  | CTCTTGGTGGGCAACCAGATCTCGC |
| XQ-252as | CCGCCACGTAGAAGAAAGCCCGGAG |
| XQ-252s  | TCTTGGTGGGCAACCAGATCTCGCT |
| XQ-253as | GCCGCCACGTAGAAGAAAGCCCGGA |
| XQ-253s  | CTTGGTGGGCAACCAGATCTCGCTG |
| XQ-254as | GGCCGCCACGTAGAAGAAAGCCCGG |
| XQ-254s  | TTGGTGGGCAACCAGATCTCGCTGC |
| XQ-255as | GGGCCGCCACGTAGAAGAAAGCCCG |

FIG. 20 (CONTINUED)

| | |
|---|---|
| XQ-255s | TGGTGGGCAACCAGATCTCGCTGCT |
| XQ-256as | TGAGCCGCCACGTAGAAGAAAGCCC |
| XQ-256s | GGTGGGCAACCAGATCTCGCTGCTC |
| XQ-257as | CTGGGCCGCCACGTAGAAGAAAGCC |
| XQ-257s | GTGGGCAACCAGATCTCGCTGCTCC |
| XQ-258as | GCTGGGCCGCCACGTAGAAGAAAGC |
| XQ-258s | TGGGCAACCAGATCTCGCTGCTCCG |
| XQ-259as | AGCTGGGCCGCCACGTAGAAGAAAG |
| XQ-259s | GGGCAACCAGATCTCGCTGCTCCGG |
| XQ-260as | CAGCTGGGCCGCCACGTAGAAGAAA |
| XQ-260s | GGCAACCAGATCTCGCTGCTCCGGG |
| XQ-261as | CCAGCTGGGCCGCCACGTAGAAGAA |
| XQ-261s | GCAACCAGATCTCGCTGCTCCGGGC |
| XQ-262as | ACCAGCTGGGCCGCCACGTAGAAGA |
| XQ-262s | CAACCAGATCTCGCTGCTCCGGGCT |
| XQ-263as | CACAAGCTGGGCCGCCACGTAGAAG |
| XQ-263s | AACCAGATCTCGCTGCTCCGGGCTT |

FIG. 20 (CONTINUED)

| | |
|---|---|
| XQ-264as | CCACAAGCTGGGCCGCCACGTAGAA |
| XQ-264s  | ACCAGATCTCGCTGCTCCGGGCTTT |
| XQ-265as | CCCACAAGCTGGGCCGCCACGTAGA |
| XQ-265s  | CCAGATCTCGCTGCTCCGGGCTTTC |
| XQ-266as | GCCCACCAGCTGGGCCGCCACGTAG |
| XQ-266s  | CAGATCTCGCTGCTCCGGGCTTTCT |
| XQ-267as | CGCCCACCAGCTGGGCCGCCACGTA |
| XQ-267s  | AGATCTCGCTGCTCCGGGCTTTCTT |
| XQ-268as | GCGCCCACCAGCTGGGCCGCCACGT |
| XQ-268s  | GATCTCGCTGCTCCGGGCTTTCTTC |
| XQ-269as | GGCGCCCACCAGCTGGGCCGCCACG |
| XQ-269s  | ATCTCGCTGCTCCGGGCTTTCTTCT |
| XQ-270as | TGGCGCCCACCAGCTGGGCCGCCAC |
| XQ-270s  | TCTCGCTGCTCCGGGCTTTCTTCTA |
| XQ-271as | ATGGCGCCCACCAGCTGGGCCGCCA |
| XQ-271s  | CTCGCTGCTCCGGGCTTTCTTCTAC |
| XQ-272as | AATGGCGCCCACCAGCTGGGCCGCC |

FIG. 20 (CONTINUED)

| | |
|---|---|
| XQ-272s | TCGCTGCTCCGGGCTTTCTTCTACG |
| XQ-273as | CAATGGCGCCCACCAGCTGGGCCGC |
| XQ-273s | CGCTGCTCCGGGCTTTCTTCTACGT |
| XQ-274as | GCAATGGCGCCCACCAGCTGGGCCG |
| XQ-274s | GCTGCTCCGGGCTTTCTTCTACGTG |
| XQ-275as | GGCAATGGCGCCCACCAGCTGGGCC |
| XQ-275s | CTGCTCCGGGCTTTCTTCTACGTGG |
| XQ-276as | CGGCAATGGCGCCCACCAGCTGGGC |
| XQ-276s | TGCTCCGGGCTTTCTTCTACGTGGC |
| XQ-277as | CCGGCAATGGCGCCAACCAGCTGGG |
| XQ-277s | GCTCCGGGCTTTCTTCTACGTGGCG |
| XQ-278as | CCCGGCAATGGCGCCCAACAGCTGG |
| XQ-278s | CTCCGGGCTTTCTTCTACGTGGCGG |
| XQ-279as | CCCCGGCAATGGCGCCCACAAGCTG |
| XQ-279s | TCCGGGCTTTCTTCTACGTGGCGGC |
| XQ-280as | GCCCCGGCAATGGAGCCCACCAGCT |

FIG. 20 (CONTINUED)

| | |
|---|---|
| XQ-280s | CCGGGCTTTCTTCTACGTGGCGGCC |
| XQ-281as | AGCCCCGGCAATGGAGCCCACCAGC |
| XQ-281s | CGAGCTTTCTTCTACGTGGCGGCCC |
| XQ-282as | CAGCCCCGGCAATGGAGCCCACCAG |
| XQ-282s | GGGCTTTCTTCTACGTGGCGGCCCA |
| XQ-283as | CCAGCCCCGGCAATGGAGCCCACCA |
| XQ-283s | GGCTTTCTTCTACGTGGCGGCCCAG |
| XQ-284as | GCCAGCCCCGGCAATGGAGCCCACC |
| XQ-284s | GCTTTCTTCTACGTGGCGGCCCAGC |
| XQ-285as | TGCCAGCCCCGGCAATGGAGCCCAC |
| XQ-285s | CTTTCTTCTACGTGGCGGCCCAGCT |
| XQ-286as | ATGCCAGCCCCGGCAATGGAGCCCA |
| XQ-286s | TTTCTTCTACGTGGCGGCCAGCTG |
| XQ-287as | GATGCCAGCCCCGGCAATGGAGCCC |
| XQ-287s | TTCTTCTACGTGGCGGCCAAGCTGG |

FIG. 20 (CONTINUED)

| | |
|---|---|
| XQ-288as | GGATGCCAGCCCCGGCAATGACGCC |
| XQ-288s | TCTTCTACGTGGCGGCCAAGCTGGT |
| XQ-289as | AGGATGCCAGCCCCGGCAATGGCGC |
| XQ-289s | CTTCTACGTGGCGGCCAAGCTGGTG |
| XQ-290as | GAGGATGCCAGCCCCGGCAATGGCG |
| XQ-290s | TTCTACGTGGCGGCCAAGCTGGTGG |
| XQ-291as | AGAGGATGACAGCCCCGGCAATGGC |
| XQ-291s | TCTACGTGGCGGCCAAGCTGGTGGG |
| XQ-292as | TAGAGGATGCCAGCCCCGGCAATGG |
| XQ-292s | CTACGTGGCGGCCAAGCTGGTGGGC |
| XQ-293as | GTAGAGGATGCCAGCCCCGGCAATG |
| XQ-293s | TACGTGGCGGCCAAGCTGGTGGGCG |
| XQ-294as | CGTAGAGGATGCCAGCCCCGGCAAT |
| XQ-294s | ACGTGGCGGCCAAGCTGGTGGGCGC |

FIG. 20 (CONTINUED)

| | |
|---|---|
| XQ-295as | CCGTAGAGGATGCCAGCCCCGGCAA |
| XQ-295s  | CGTGGCGGCCCAGCTGGTGGGCGCC |
| XQ-296as | ACCGTAGAGGATACCAGCCCCGGCA |
| XQ-296s  | GTCGCGGCCCAGCTGGTGGGCGCCA |
| XQ-297as | CACCGTAGAGGATGCCAGCCCCGGC |
| XQ-297s  | TGGCGGCCCAGCTGGTGGGCGCCAT |
| XQ-298as | ACACCGTAGAGGATGCCAGCCCCGG |
| XQ-298s  | GGCGGCCCAGCTGGTGGGCGCCATT |
| XQ-299as | CACACCGTAGAGGATGCCAGCCCCG |
| XQ-299s  | GCGGCCCAGCTGGTGGGCGCCATTG |
| XQ-300as | CCACACCGTAGAGGATGCCAGCCCC |
| XQ-300s  | CGGCCCAGCTGGTGGGCGCCATTGC |
| XQ-301as | GCCACACCGTAGAGGATGCCAGCCC |
| XQ-301s  | GGCCCAGCTGGTGGGCGCCATTGCC |
| XQ-302as | TGCCACACCGTAGAGGATGCCAGCC |
| XQ-302s  | GCCCAGCTGGTGGGCGCCATTGCCG |
| XQ-303as | GTGCCACACCGTAGAGGATGCCAGC |

FIG. 20 (CONTINUED)

| | |
|---|---|
| XQ-303s | CCCAGCTGGTGGGAGCCATTGCCGG |
| XQ-304as | GGTGCCACACCGTAGAGGATGCCAG |
| XQ-304s | CCAGCTGGTGGGAGCCATTGCCGGG |
| XQ-305as | CGATGCCACACCGTAGAGGATGCCA |
| XQ-305s | CAGCTGGTGGGAGCCATTGCCGGGG |
| XQ-306as | GCGATGCCACACCGTAGAGGATGCC |
| XQ-306s | AGCTGGTGGGAGCCATTGCCGGGGC |
| XQ-307as | AGCGATGCCACACCGTAGAGGATGC |
| XQ-307s | GCTGGTGGTCGCCATTGCCGGGGCT |
| XQ-308as | GAGCGATGCCACACCGTAGAGGATG |
| XQ-308s | CTGGTGGGAGCCATTGCCGGGGCTG |
| XQ-309as | TGAGCGATGCCACACCGTAGAGGAT |
| XQ-309s | TGGTGGGAGCCATTGCCGGGGCTGG |
| XQ-310as | TTGAGCGATGCCACACCGTAGAGGA |
| XQ-310s | GGTGGGCGACATTGCCGGGGCTGGC |
| XQ-311as | ATTGAGCGATGCCACACCGTAGAGG |
| XQ-311s | GTGGGCGCCATTGACGGGGCTGGCA |

FIG. 20 (CONTINUED)

| | |
|---|---|
| XQ-312as | CATTGAGCGATGCCACACCGTAGAG |
| XQ-312s | TGGGCGCCATTGCCGGGGCTGGCAT |
| XQ-313as | GCATTGAGCGATGCCACACCGTAGA |
| XQ-313s | GGGCGCCATTGCCGGGGCTGGCATC |
| XQ-314as | GGCATTGAGCGTTGCCACACCGTAG |
| XQ-314s | GGCGCCATTGCCGGGGCTGGCATCC |
| XQ-315as | GGGCATTGAGCGTTGCCACACCGTA |
| XQ-315s | GCGCCATTGCCGGGGCTGGCATCCT |
| XQ-316as | CGGGCATTGAGCGTTGCCACACCGT |
| XQ-316s | CGCCATTGCCGGGGCTGGCATCCTC |
| XQ-317as | CCGGGCATTGAGCAGTGCCACACCG |
| XQ-317s | GCCATTGCCGGGGCTGGCATCCTCT |
| XQ-318as | CCCGGGCATTGAGCGTTGCCACACC |
| XQ-318s | CCATTGCCGGGGCTGGCATCCTCTA |
| XQ-319as | CCCCGGGCATTGAGCGGTGCCACAC |
| XQ-319s | CATTGCCGGGGCTGGCATCCTCTAC |
| XQ-320as | GCCCCGGGCATTGAGCGGTGCCACA |

FIG. 20 (CONTINUED)

| | |
|---|---|
| XQ-320s | ATTGCCGGGGCTGGCATCCTCTACG |
| XQ-321as | TGCCCCGGGCATTGAGCGGTGCCAC |
| XQ-321s | TTGCCGGGGCTGGCATCCTCTACGG |
| XQ-322as | TTGCCCCGGGCATTGAGCGGTGCCA |
| XQ-322s | TGCCGGGGCTGGCATCCTCTACGGT |
| XQ-323as | ATTGCCCCGGACATTGAGCGGTGCC |
| XQ-323s | GCCGGGGCTGGCATCCTCTACGGTG |
| XQ-324as | GATTGCCCCGGGCATTGAGCGGTGC |
| XQ-324s | CCGGGGCTGGCATCCTCTACGGTGT |
| XQ-325as | AGATTGCCCCGGGCATTGAGCGGTG |
| XQ-325s | CGGGGCTGGCATCCTCTACGGTGTG |
| XQ-326as | CAGATTCCCCGGGCATTGAGCGGT |
| XQ-326s | GGGGCTGGCATCCTCTACGGTGTGG |
| XQ-327as | CCAGATTGCACCGGGCATTGAGCGG |
| XQ-327s | GGGCTGGCATCCTCTACGGTGTGGC |
| XQ-328as | GCCAGATTGCACCGGGCATTGAGCG |
| XQ-328s | GGCTGGCATCCTCTACGGTGTGGCA |

FIG. 20 (CONTINUED)

| | |
|---|---|
| XQ-329as | GGCCAGATTGCACCGGGCATTGAGC |
| XQ-329s | GCTGGCATCCTCTACGGTGTGGCAC |
| XQ-330as | CGGCCAGATTGCACCGGGCATTGAG |
| XQ-330s | CTGGCATCCTCTACGATGTGGCACC |
| XQ-331as | ACGGCCAGATTGCACCGGGCATTGA |
| XQ-331s | TGGCATCCTCTACAGTGTGGCACCG |
| XQ-332as | GACGGCCAGATTGCACCGGGCATTG |
| XQ-332s | GGCATCCTCTACGATGTGGCACCGC |
| XQ-333as | TGACGGCCAGATTGCACCGGGCATT |
| XQ-333s | GCATCCTCTACGATGTGGCACCGCT |
| XQ-334as | TTGACGGCCAGATTGCACCGGGCAT |
| XQ-334s | CATCCTCTACGATGTGGCACCGCTC |
| XQ-335as | GTTGACGGCCAGATTGCACCGGGCA |
| XQ-335s | ATCCTCTACGATGTGGCACCGCTCA |
| XQ-336as | CGTTGACGGCCAGATTGCACCGGGC |
| XQ-336s | TCCTCTACGATGTGGCACCGCTCAA |

FIG. 20 (CONTINUED)

| | |
|---|---|
| XQ-337as | GCGTTGACGGCCAGATTGCCACGGG |
| XQ-337s | CCTCTACGATGTGGCACCGCTCAAT |
| XQ-338as | CGCGTTGACGGCCAGATTGCCCCGG |
| XQ-338s | CTCTACGATGTGGCACCGCTCAATG |
| XQ-339as | GCGCGTTGACGGCCAGATTGCCCCG |
| XQ-339s | TCTACGATGTGGCACCGCTCAATGC |
| XQ-340as | AGCGCGTTGACGGCCAGATTGCCCC |
| XQ-340s | CTACGGTGTGGAACCGCTCAATGCC |
| XQ-341as | GAGCGCGTTGACGGCCAGATTGCCC |
| XQ-341s | TACGATGTGGCACCGCTCAATGCCC |
| XQ-342as | TGAGCGCGTTGACGGCCAGATTGCC |
| XQ-342s | ACGATGTGGCACCGCTCAATGCCCG |
| XQ-343as | TTGAGCGCGTTGACGGCCAGATTGC |
| XQ-343s | CGATGTGGCACCGCTCAATGCCCGG |
| XQ-344as | GTTGAGCGCGTTGACGGCCAGATTG |
| XQ-344s | GGTGTGGCACCGCTCAATGCACGGG |

FIG. 20 (CONTINUED)

| | |
|---|---|
| XQ-345as | TGTTGAGCGCGTTGACGGCCAGATT |
| XQ-345s  | GTGTGGCACCGCTCAATGCACGGGG |
| XQ-346as | TTGTTGAGCGCGTTGACGGCCAGAT |
| XQ-346s  | TGTGGCACCGCTCAATGACCGGGGC |
| XQ-347as | GTTGTTGAGCGCGTTGACGGCCAGA |
| XQ-347s  | GTGGCACCGCTCAATGCCCGGGGCA |
| XQ-348as | TGTTGTTGAGCGCGTTGACGGCCAG |
| XQ-348s  | TGGCACCGCTCAATGACCGGGGCAA |
| XQ-349as | TTGTTGTTGAGCGCGTTGACGGCCA |
| XQ-349s  | GGCACCGCTCAATGACCGGGGCAAT |
| XQ-350as | GTTGTTGTTGAGCGCGTTGACGGCC |
| XQ-350s  | GCACCGCTCAATGACCGGGGCAATC |
| XQ-351as | TGTTGTTGTTGAGCGCGTTGACGGC |
| XQ-351s  | CACCGCTCAATGACCGGGGCAATCT |
| XQ-352as | GTGTTGTTGTTGAGCGCGTTGACGG |

FIG. 20 (CONTINUED)

| | |
|---|---|
| XQ-352s | ACCGCTCAATGACCGGGGCAATCTG |
| XQ-353as | TGTGTTGTTGTTGAGCGCGTTGACG |
| XQ-353s | CCGCTCAATGACCGGGGCAATCTGG |
| XQ-354as | TTGTGTTGTTGTTGAGCGCGTTGAC |
| XQ-354s | CGCTCAATGACCGGGGCAATCTGGC |
| XQ-355as | GTTGTGTTGTTGTTGAGCGCGTTGA |
| XQ-355s | GCTCAATGACCGGGGCAATCTGGCC |
| XQ-356as | CGTTGTGTTGTTGTTGAGCGCGTTG |
| XQ-356s | CTCAATGACCGGGGCAATCTGGCCG |
| XQ-357as | GCGTTGTGTTGTTGTTGAGCGCGTT |
| XQ-357s | TCAATGACCGGGGCAATCTGGCCGT |
| XQ-358as | TGCGTTGTGTTGTTGTTGAGCGCGT |
| XQ-358s | CAATGACCGGGGCAATCTGGCCGTC |
| XQ-359as | CTGCGTTGTGTTGTTGTTGAGCGCG |
| XQ-359s | AATGGCCGGGGCAATCTGGCCGTCA |
| XQ-360as | CCTGCGTTGTGTTGTTGTTGAGCGC |
| XQ-360s | ATGACCGGGGCAATCTGGCCGTCAA |

FIG. 20 (CONTINUED)

| | |
|---|---|
| XQ-361as | CCCTGCGTTGTGTTGTTGTTGAGCG |
| XQ-361s | TGACCGGGGCAATCTGGCCGTCAAC |
| XQ-362as | GCCTGCGTTGTGTTGTTGTTGAGC |
| XQ-362s | GCCCGGGGCAATCTGGCCGTCAACG |
| XQ-363as | GGCCTGCGTTGTGTTGTTGTTGAG |
| XQ-363s | CCCGGGGCAATCTGGCCGTCAACGC |
| XQ-364as | TGGCCTGCGTTGTGTTGTTGTTGA |
| XQ-364s | CCGGGGCAATCTGGCCGTCAACGCG |
| XQ-365as | CTGGCCTGCGTTGTGTTGTTGTTG |
| XQ-365s | CGGGGCAATCTGGCCGTCAACGCGC |
| XQ-366as | CCTGGCCTGCGTTGTGTTGTTGTT |
| XQ-366s | GGGGCAATCTGGCCGTCAACGCGCT |
| XQ-367as | GCCTGGCCTGCGTTGTGTTGTTGT |
| XQ-367s | GGGCAATCTGGCCGTCAACGCGCTC |
| XQ-368as | GGCCTGGCCTGCGTTGTGTTGTTG |
| XQ-368s | GGCAATCTGGCCGTCAACGCGCTCA |
| XQ-369as | TGGCCTGGCCCTGCGTTGTGTTGTT |

FIG. 20 (CONTINUED)

| | |
|---|---|
| XQ-369s | GCAATCTGGCCGTCAACGCGCTCAA |
| XQ-370as | ATGGCCTGGCCCTGCGTTGTGTTGT |
| XQ-370s | CAATCTGGCCGTCAACGCGCTCAAC |
| XQ-371as | CATGGCCTGGCCCTGCGTTGTGTTG |
| XQ-371s | AATCTGGCCGTCAACGCGCTCAACA |
| XQ-372as | CCATGGCCTGGCCCTGCGTTGTGTT |
| XQ-372s | ATCTGGCCGTCAACGCGCTCAACAA |
| XQ-373as | ACCATGGCCTGGCCCTGCGTTGTGT |
| XQ-373s | TCTGGCCGTCAACGCGCTCAACAAC |
| XQ-374as | CACCATGGCCTGGCCCTGCGTTGTG |
| XQ-374s | CTGGCCGTCAACGCGCTCAACAACA |
| XQ-375as | CCACAATGGCCTGGCCCTGCGTTGT |
| XQ-375s | TGGCCGTCAACGCGCTCAACAACAA |
| XQ-376as | ACCACAATGGCCTGGCCCTGCGTTG |
| XQ-376s | GGCCGTCAACGCGCTCAACAACAAC |
| XQ-377as | CACCACAATGGCCTGGCCCTGCGTT |
| XQ-377s | GCCGTCAACGCGCTCAACAACAACA |

FIG. 20 (CONTINUED)

| | |
|---|---|
| XQ-378as | CCACCACAATGGCCTGGCCCTGCGT |
| XQ-378s | CCGTCAACGCGCTCAACAACAACAC |
| XQ-379as | TCCACCACAATGGCCTGGCCCTGCG |
| XQ-379s | CGTCAACGCGCTCAACAACAACACA |
| XQ-380as | CTCCACCACAATGGCCTGGCCCTGC |
| XQ-380s | GTCAACGCGCTCAACAACAACACAA |
| XQ-381as | GCTCCACCACAATGGCCTGGCCCTG |
| XQ-381s | TCAACGCGCTCAACAACAACACAAC |
| XQ-382as | AGCTCCACCACAATGGCCTGGCCCT |
| XQ-382s | CAACGCGCTCAACAACAACACAACG |
| XQ-383as | CAGCTCCACCACAATGGCCTGGCCC |
| XQ-383s | AACGCGCTCAACAACAACACAACGC |
| XQ-384as | TCAGCTCCACCACCATGACCTGGCC |
| XQ-384s | ACGCGCTCAACAACAACACAACGCA |
| XQ-385as | ATCAGCTCCACCACAATGGCCTGGC |
| XQ-385s | CGCGCTCAACAACAACACAACGCAG |

FIG. 20 (CONTINUED)

| | |
|---|---|
| XQ-386as | AATCAGCTCCACCACAATGGCCTGG |
| XQ-386s  | GCGCTCAACAACAACACAACGCAGG |
| XQ-387as | GAATCAGCTCCACCACAATGGCCTG |
| XQ-387s  | CGCTCAACAACAACACAACGCAGGG |
| XQ-388as | AGAATCAGCTCCACCACAATGGCCT |
| XQ-388s  | GCTCAACAACAACACAACGCAGGGC |
| XQ-389as | CAGAATCAGCTCCACCACAATGGCC |
| XQ-389s  | CTCAACAACAACACAACGCAGGGCC |
| XQ-390as | TCAGAATCAGCTCCACCACAATGGC |
| XQ-390s  | TCAACAACAACACAACGCAGGGCCA |
| XQ-391as | GTCAGAATCAGCTCCACCACAATGG |
| XQ-391s  | CAACAACAACACAACGCAGGGCCAG |
| XQ-392as | GGTCAGAATCAGCTCCACCACCATG |
| XQ-392s  | AACAACAACACAACGCAGGGCCAGG |

FIG. 20 (CONTINUED)

| | |
|---|---|
| XQ-393as | AGGTCAGAATCAGCTCCACCACCAT |
| XQ-393s  | ACAACAACACAACGCAGGGCCAGGC |
| XQ-394as | AAGGTCAGAATCAGCTCCACCACCA |
| XQ-394s  | CAACAACACAACGCAGGACCAGGCC |
| XQ-395as | GAAGGTCAGAATCAGCTCCACCACC |
| XQ-395s  | AACAACACAACGCAGGGCCAGGCCA |
| XQ-396as | GGAAGGTCAGAATCAGCTCCACCAC |
| XQ-396s  | ACAACACAACGCAGGGCCAGGCCAT |
| XQ-397as | TGGAAGGTCAGAATCAGCTCCACCA |
| XQ-397s  | CAACACAACGCAGGGCCAGGCCATG |
| XQ-398as | CTGGAAGGTCAGAATCAGCTCCACC |
| XQ-398s  | AACACAACGCAGGGCCAGGCAATGG |
| XQ-399as | GCTGGAAGGTCAGAATCAGCTCCAC |
| XQ-399s  | ACACAACGCAGGGCCAGGCAATGGT |

FIG. 20 (CONTINUED)

| | |
|---|---|
| XQ-400as | AGCTAGAAGGTCAGAATCAGCTCCA |
| XQ-400s | CACAACGCAGGGCCAGGCAATGGTG |
| XQ-401as | CAGATGGAAGGTCAGAATCAGCTCC |
| XQ-401s | ACAACGCAGGGCCAGGCAATGGTGG |
| XQ-402as | CCAGATGGAAGGTCAGAATCAGCTC |
| XQ-402s | CAACGCAGGGCCAGGCAATGGTGGT |
| XQ-403as | GCCAACTGGAAGGTCAGAATCAGCT |
| XQ-403s | AACGCAGGGCCAGGCAATGGTGGTG |
| XQ-404as | TGCCAGATGGAAGGTCAGAATCAGC |
| XQ-404s | ACGCAGGGCCAGGCAATGGTGGTGG |
| XQ-405as | GTGCAAGCTGGAAGGTCAGAATCAG |
| XQ-405s | CGCAGGGCCAGGCAATGGTGGTGGA |
| XQ-406as | AGTGCAAGCTGGAAGGTCAGAATCA |
| XQ-406s | GCAGGGCCAGGCAATGGTGGTGGAG |
| XQ-407as | GAGTGCAAGCTGGAAGGTCAGAATC |
| XQ-407s | CAGGGCCAGGCAATGGTGGTGGAGC |
| XQ-408as | AGAGTGCAAGCTGGAAGGTCAGAAT |
| XQ-408s | AGGGCCAGGCAATGGTGGTGGAGCT |

FIG. 20 (CONTINUED)

| | |
|---|---|
| XQ-409as | CAGAGTGCAAGCTGGAAGGTCAGAA |
| XQ-409s | GGGCCAGGCAATGGTGGTGGAGCTG |
| XQ-410as | GCAGAGTGCAAGCTGGAAGGTCAGA |
| XQ-410s | GGCCAGGCAATGGTGGTGGAGCTGA |
| XQ-411as | TGCAGAGTGCAAGCTGGAAGGTCAG |
| XQ-411s | GCCAGGCAATGGTGGTGGAGCTGAT |
| XQ-412as | ATGCAGAGTGCAAGCTGGAAGGTCA |
| XQ-412s | CCAGGCAATGGTGGTGGAGCTGATT |
| XQ-413as | GATGCAGAGTGCAAGCTGGAAGGTC |
| XQ-413s | CAGGCAATGGTGGTGGAGCTGATTC |
| XQ-414as | AGATGCAGAGTGCAAGCTGGAAGGT |
| XQ-414s | AGGCAATGGTGGTGGAGCTGATTCT |
| XQ-415as | AAGATGCAGAGTGCAAGCTGGAAGG |
| XQ-415s | GGCCATGGTGGTGGAGCTGATTCTG |
| XQ-416as | GAAGATGCAGAGTGCAAGCTGGAAG |
| XQ-416s | GCCATGGTGGTGGAGCTGATTCTGA |
| XQ-417as | CGAAGATGCAGAGTGCAAGCTGGAA |

FIG. 20 (CONTINUED)

| | |
|---|---|
| XQ-417s | CCATGGTGGTGGAGCTGATTCTGAC |
| XQ-418as | GCGAAGATGCAGAGTGCAAGCTGGA |
| XQ-418s | CATGGTGGTGGAGCTGATTCTGACC |
| XQ-419as | GGCGAAGATGCAGAGTGCAAGCTGG |
| XQ-419s | ATGGTGGTGGAGCTGATTCTGACCT |
| XQ-420as | AGGCGAAGATGCAGAGTGCAAGCTG |
| XQ-420s | TGGTGGTGGAGCTGATTCTGACCTT |
| XQ-421as | GAGGCGAAGATGCAGAGTGCCAGCT |
| XQ-421s | GGTGGTGGAGCTGATTCTGACCTTC |
| XQ-422as | GGAGGCGAAGATGCAGAGTGCCAGC |
| XQ-422s | GTGGTGGAGCTGATTCTGACCTTCC |
| XQ-423as | TGGAGGCGAAGATGCAGAGTGCCAG |
| XQ-423s | TGGTAGAGCTGATTCTGACCTTCCA |
| XQ-424as | GTGGAGGCGAAGATGCAGAGTGCCA |
| XQ-424s | GGTGGAGCTGATTCTGACCTTCCAG |
| XQ-425as | AGTGGAGGCGAAGATGCAGAGTGCC |
| XQ-425s | GTGGAGATGATTCTGACCTTCCAGC |

FIG. 20 (CONTINUED)

| | |
|---|---|
| XQ-426as | CAGTGGAGGCGAAGATGCAGAGTGC |
| XQ-426s  | TGGAACTGATTCTGACCTTCCAGCT |
| XQ-427as | TCAGTGGAGGCGAAGATGCAGAGTG |
| XQ-427s  | GGAGCTGATTCTGACCTTCAAGCTG |
| XQ-428as | GTCAGTGGAGGCGAAGATGCAGAGT |
| XQ-428s  | GAGCTGATTCTGACCTTCAAGCTGG |
| XQ-429as | AGTCAGTGGAGGCGAAGATGCAGAG |
| XQ-429s  | AGCTGATTCTGACCTTCCAGCTGGC |
| XQ-430as | GAGTCAGTGGAGGCGAAGATGCAGA |
| XQ-430s  | GCTGATTCTGACCTTCAAGCTGGCA |
| XQ-431as | GGAGTCAGTGGAGGCGAAGATGCAG |
| XQ-431s  | CTGATTCTGACCTTCAAGCTGGCAC |
| XQ-432as | GGGAGTCAGTGGAGGCGAAGATGCA |
| XQ-432s  | TGATTCTGACCTTCAAGCTGGCACT |
| XQ-433as | CGGGAGTCAGTGGAGGCGAAGATGC |
| XQ-433s  | GATTCTGACCTTCAAGCTGGCACTC |

FIG. 20 (CONTINUED)

| | |
|---|---|
| XQ-434as | GCGGGAGTCAGTGGAGGCGAAGATG |
| XQ-434s  | ATTCTGACCTTCAAGCTGGCACTCT |
| XQ-435as | GGCGGGAGTCAGTGGAGGCGAAGAT |
| XQ-435s  | TTCTGACCTTCAAGCTGGCACTCTG |
| XQ-436as | CGGCGGGAGTCAGTGGAGGCGAAGA |
| XQ-436s  | TCTGACCTTCAAGCTGGCACTCTGC |
| XQ-437as | GCGGCGGGAGTCAGTGGAGGCGAAG |
| XQ-437s  | CTGACCTTCAAGCTGGCACTCTGCA |
| XQ-438as | TGCGGCGGGAGTCAGTGGAGGCGAA |
| XQ-438s  | TGACCTTCAAGCTGGCACTCTGCAT |
| XQ-439as | GTGCGGCGGGAGTCAGTGGAGGCGA |
| XQ-439s  | GACCTTCAAGCTGGCACTCTGCATC |
| XQ-440as | GGTGCGGCGGGAGTCAGTGGAGGCG |
| XQ-440s  | ACCTTCAAGCTGGCACTCTGCATCT |
| XQ-441as | TGGTGCGGCGGGAGTCAGTGGAGGC |
| XQ-441s  | CCTTCAAGCTGGCACTCTGCATCTT |
| XQ-442as | CTGGTGCGGCGGGAGTCAGTGGAGG |
| XQ-442s  | CTTCAAGCTGGCACTCTGCATCTTC |

FIG. 20 (CONTINUED)

| | |
|---|---|
| XQ-443as | GCTGGTGCGGCGGGAGTCAGTGGAG |
| XQ-443s  | TTCAAGCTGGCACTCTGCATCTTCG |
| XQ-444as | GGCTGGTGCGGCGGGAGTCAGTGGA |
| XQ-444s  | TCCAGCTGGCACTCTGCATCTTCGC |
| XQ-445as | GGGCTGGTGCGGCGGGAGTCAGTGG |
| XQ-445s  | CCAGCTGGCACTCTGCATCTTCGCC |
| XQ-446as | AGGGCTGGTGCGGCGGGAGTCAGTG |
| XQ-446s  | CAGCTGGCACTCTGCATCTTCGCCT |
| XQ-447as | CAGGGCTGGTGCGGCGGGAGTCAGT |
| XQ-447s  | AGCTGGCACTCTGCATCTTCGCCTC |
| XQ-448as | ACAGGGCTGGTGCGGCGGGAGTCAG |
| XQ-448s  | GCTGGCACTCTGCATCTTCGCCTCC |
| XQ-449as | CACAGGGCTGGTGCGGCGGGAGTCA |
| XQ-449s  | CTGGCACTCTGCATCTTCGCCTCCA |
| XQ-450as | CCACAGGGCTGGTGCGGCGGGAGTC |
| XQ-450s  | TGGCACTCTGCATCTTCGCCTCCAC |
| XQ-451as | CCCACAGGGCTGGTGCGGCGGGAGT |

FIG. 20 (CONTINUED)

| | |
|---|---|
| XQ-451s | GGCACTCTGCATCTTCGCCTCCACT |
| XQ-452as | GCCCACAGGGCTGGTGCGGCGGGAG |
| XQ-452s | GCACTCTGCATCTTCGCCTCCACTG |
| XQ-453as | AGACCACAGGGCTGGTGCGGCGGGA |
| XQ-453s | CACTCTGCATCTTCGCCTCCACTGA |
| XQ-454as | GAGACCACAGGGCTGGTGCGGCGGG |
| XQ-454s | ACTCTGCATCTTCGCCTCCACTGAC |
| XQ-455as | GGAGACCACAGGGCTGGTGCGGCGG |
| XQ-455s | CTCTGCATCTTCGCCTCCACTGACT |
| XQ-456as | GGGAGACCACAGGGCTGGTGCGGCG |
| XQ-456s | TCTGCATCTTCGCCTCCACTGACTC |
| XQ-457as | GGGGAGACCACAGGGCTGGTGCGGC |
| XQ-457s | CTGCATCTTCGCCTCCACTGACTCC |
| XQ-458as | TGGGGAGACCACAGGGCTGGTGCGG |
| XQ-458s | TGCATCTTCGCCTCCACTGACTCCC |
| XQ-459as | CTGGGGAGACCACAGGGCTGGTGCG |
| XQ-459s | GCATCTTCGCCTCCACTGACTCCCG |
| XQ-460as | GCTGGGGAGACCACAGGGCTGGTGC |

FIG. 20 (CONTINUED)

| | |
|---|---|
| XQ-460s | CATCTTCGCCTCCACTGACTCCCGC |
| XQ-461as | GGCTGGGGAGACCACAGGGCTGGTG |
| XQ-461s | ATCTTCGCCTCCACTGACTCCCGCC |
| XQ-462as | GGGCTGGGGAGCCCACAGGGCTGGT |
| XQ-462s | TCTTCGCCTCCACTGACTCCCGCCG |
| XQ-463as | AGGGCTGGGGAGCCCACAGGGCTGG |
| XQ-463s | CTTCGCCTCCACTGACTCCCGCCGC |
| XQ-464as | CAGGGCTGGGGAGCCCACAGGGCTG |
| XQ-464s | TTCGCCTCCACTGACTCCCGCCGCA |
| XQ-465as | ACAGGGCTGGGGAACCCACAGGGCT |
| XQ-465s | TCGCCTCCACTGACTCCCGCCGCAC |
| XQ-466as | GACAGGGCTGGGGAGACCACAGGGC |
| XQ-466s | CGCCTCCACTGACTCCCGCCGCACC |
| XQ-467as | GGACAGGACTGGGGAGCCCACAGGG |
| XQ-467s | GCCTCCACTGACTCCCGCCGCACCA |
| XQ-468as | TGGACAGGACTGGGGAGCCCACAGG |
| XQ-468s | CCTCCACTGACTCCCGCCGCACCAG |

FIG. 20 (CONTINUED)

| | |
|---|---|
| XQ-469as | ATGGACAGGACTGGGGAGCCCACAG |
| XQ-469s  | CTCCACTGACTCCCGCCGCACCAGC |
| XQ-470as | AATGGACAGGACTGGGGAGCCCACA |
| XQ-470s  | TCCACTGACTCCCGCCGCACCAGCC |
| XQ-471as | CAATGGACAGGACTGGGGAGCCCAC |
| XQ-471s  | CCACTGACTCCCGCCGCACCAGCCC |
| XQ-472as | CCAATGGACAGGGCAGGGGAGCCCA |
| XQ-472s  | CACTGACTCCCGCCGCACCAGCCCT |
| XQ-473as | GCCAATGGACAGAGCTGGGGAGCCC |
| XQ-473s  | ACTGACTCCCGCCGCACCAGCCCTG |
| XQ-474as | GGCCAATGGACAGGACTGGGGAGCC |
| XQ-474s  | CTGACTCCCGCCGCACCAGCCCTGT |
| XQ-475as | AGGCCAATGGACAGGGCTGGGGAGC |
| XQ-475s  | TGACTCCCGCCGCACCAGCCCTGTG |
| XQ-476as | CAGGCCAATGGACAGGGCTGGGGAG |
| XQ-476s  | GACTCCCGCCGCACCAGCCCTGTGG |
| XQ-477as | ACAGGCCAATGGACAGGGCTGGGGA |
| XQ-477s  | ACTCCCGCCGCACCAGCCCTGTGGG |

FIG. 20 (CONTINUED)

| | |
|---|---|
| XQ-478as | GACAGGCCAATGGACAGGGCTGGGG |
| XQ-478s  | CTCCCGCCGCACCAGACCTGTGGGC |
| XQ-479as | AGACAGGCCAATGGACAGGGCTGGG |
| XQ-479s  | TCCCGCCGCACCAACCCTGTGGGCT |
| XQ-480as | CAGACAGGCCAATGGACAGGGCTGG |
| XQ-480s  | CCCGCCGCACCAGACCTGTGGGCTC |
| XQ-481as | ACAGACAGGCCAATGGACAGGGCTG |
| XQ-481s  | CCGCCGCACCAGACCTGTGGGCTCC |
| XQ-482as | GACAGACAGGCCAATGGACAGGGCT |
| XQ-482s  | CGCCGCACCAGACCTGTGGGCTCCC |
| XQ-483as | TGACAGACAGGCCAATGGACAGGGC |
| XQ-483s  | GCCGCACCAGACCTGTGGGCTCCCC |
| XQ-484as | GTGACAGACAGGCCAATGGACAGGG |
| XQ-484s  | CCGCACCAGCCCTGTAGGCTCCCCA |
| XQ-485as | GGTGACAGACAGGCCAATGGACAGG |
| XQ-485s  | CGCACCAGACCTGTGGGCTCCCCAG |
| XQ-486as | GGGTGACAGACAGGCCAATGGACAG |

FIG. 20 (CONTINUED)

| | |
|---|---|
| XQ-486s | GCACCAGACCTGTGGGCTCCCCAGC |
| XQ-487as | AGGGTGACAGACAGGCCAATGGACA |
| XQ-487s | CACCAGCCCTGTGGACTCCCCAGCC |
| XQ-488as | CAGGGTGACAGACAGGCCAATGGAC |
| XQ-488s | ACCAGCCCTGTGTGCTCCCCAGCCC |
| XQ-489as | CCAGGGTGACAGACAGGCCAATGGA |
| XQ-489s | CCAGCCCTGTGGGCTCCCCAGCCCT |
| XQ-490as | CCCAGGGTGACAGACAGGCCAATGG |
| XQ-490s | CAGCCCTGTGGGCTCCCCAGCCCTG |
| XQ-491as | GCCCAGGGTGACAGACAGGCCAATG |
| XQ-491s | AGCCCTGTGGGCTCCCCAGCCCTGT |
| XQ-492as | GGCCCAGGGTGACAGACAGGCCAAT |
| XQ-492s | GCCCTGTGGACTCCCCAGCCCTGTC |
| XQ-493as | TGACCCAGGGTGACAGACAGGCCAA |
| XQ-493s | CCCTGTGGTCTCCCCAGCCCTGTCC |
| XQ-494as | GTAGCCCAGGGTGACAGACAGGCCA |
| XQ-494s | CCTGTGGTCTCCCCAGCCCTGTCCA |
| XQ-495as | GGTGACCCAGGGTGACAGACAGGCC |

FIG. 20 (CONTINUED)

| | |
|---|---|
| XQ-495s | CTGTGGTCTCCCCAGCCCTGTCCAT |
| XQ-496as | AGGTGGCCCAGGGTGACAGACAGGC |
| XQ-496s | TGTGGTCTCCCCAGCCCTGTCCATT |
| XQ-497as | AAGGTGGCCCAGGGTGACAGACAGG |
| XQ-497s | GTGGTCTCCCCAGCCCTGTCCATTG |
| XQ-498as | CAAGGTGGCCCAGGGTGACAGACAG |
| XQ-498s | TGGTCTCCCCAGCCCTGTCCATTGG |
| XQ-499as | ACAAGGTGGCCCAGGGTGACAGACA |
| XQ-499s | GGACTCCCCAGCCCTGTCCATTGGC |
| XQ-500as | GACAAGGTGGCCCAGGGTGACAGAC |
| XQ-500s | GGCTCCCCAGCCCTGTCCATTGGCC |
| XQ-501as | CGACAAGGTGGCCCAGGGTGACAGA |
| XQ-501s | GCTCCCCAGCCCTGTCCATTGGCCT |
| XQ-502as | CCGACAAGGTGGCCCAGGGTGACAG |
| XQ-502s | CTCCCCAGCCCTGTCCATTGGCCTG |
| XQ-503as | TCCGACAAGGTGGCCCAGGGTGACA |
| XQ-503s | TCCCCAGCCCTGTCCATTGGCCTGT |

FIG. 20 (CONTINUED)

| | |
|---|---|
| XQ-504as | TTCCGACAAGGTGGCCCAGGGTGAC |
| XQ-504s | CCCCAGCCCTGTCCATTGGCCTGTC |
| XQ-505as | ATTCCGACAAGGTGGCCCAGGGTGA |
| XQ-505s | CCCAGCCCTGTCCATTGGCCTGTCT |
| XQ-506as | GATTCCGACAAGGTGGCCCAGGGTG |
| XQ-506s | CCAGCCCTGTCCATTGGCCTGTCTG |
| XQ-507as | AGATTCCGACAAGGTGGCCCAGGGT |
| XQ-507s | CAGCCCTGTCCATTGGCCTGTCTGT |
| XQ-508as | TAGATTCCGACAAGGTGGCCCAGGG |
| XQ-508s | AGCCCTGTCCATTGGCCTGTCTGTC |
| XQ-509as | GTAGATTCCGACAAGGTGGCCCAGG |
| XQ-509s | GCCCTGTCCATTGGCCTGTCTGTCA |
| XQ-510as | AGTAGATTCCGACAAGGTGGCCCAG |
| XQ-510s | CCCTGTCCATTGGCCTGTCTGTCAC |
| XQ-511as | AAGTAGATTCCGACAAGGTGGCCCA |
| XQ-511s | CCTGTCCATTGGCCTGTCTGTCACC |
| XQ-512as | GAAGTAGATTCCGACAAGGTGGCCC |
| XQ-512s | CTGTCCATTGGCCTGTCTGTCACCC |

FIG. 20 (CONTINUED)

| | |
|---|---|
| XQ-513as | TGAAGTAGATTCCGACAAGGTGGCC |
| XQ-513s | TGTCCATTGGCCTGTCTGTCACCCT |
| XQ-514as | GTGAAGTAGATTCCGACAAGGTGGC |
| XQ-514s | GTCCATTGGCCTGTCTGTCACCCTG |
| XQ-515as | AGTGAAGTAGATTCCGACAAGGTGG |
| XQ-515s | TCCATTGGCCTGTCTGTCACCCTGG |
| XQ-516as | CAGTGAAGTAGATTCCGACAAGGTG |
| XQ-516s | CCATTGGCCTGTCTGTCACCCTGGG |
| XQ-517as | CCAGTGAAGTAGATTCCGACAAGGT |
| XQ-517s | CATTGGCCTGTCTGTCACCCTGGGC |
| XQ-518as | GCCAGTGAAGTAGATTCCGACAAGG |
| XQ-518s | ATTGACCTGTCTGTCACCCTGGGCC |
| XQ-519as | AGCCAGTGAAGTAGATTCCGACAAG |
| XQ-519s | TTAGCCTGTCTGTCACCCTGGGCCA |
| XQ-520as | CAGCCAGTGAAGTAGATTCCGACAA |
| XQ-520s | TGACCTGTCTGTCACCCTGGGCCAC |
| XQ-521as | GCAGCCAGTGAAGTAGATTCCGACA |

FIG. 20 (CONTINUED)

| | |
|---|---|
| XQ-521s | GGCCTGTCTGTCACCCTGGGCCACC |
| XQ-522as | AGCAGCCAGTGAAGTAGATTCCGAC |
| XQ-522s | GCCTGTCTGTCACCCTGGGCCACCT |
| XQ-523as | GAGCAGCCAGTGAAGTAGATTCCGA |
| XQ-523s | CCTGTCTGTCACCCTGGGCCACCTT |
| XQ-524as | GGAGCAGCCAGTGAAGTAGATTCCG |
| XQ-524s | CTGTCTGTCACCCTGGGCCACCTTG |
| XQ-525as | TGGAGCAGCCAGTGAAGTAGATTCC |
| XQ-525s | TGTCTGTCACCCTGGGCCACCTTGT |
| XQ-526as | ATGGAGCAGCCAGTGAAGTAGATTC |
| XQ-526s | GTCTGTCACCCTGGGCCACCTTGTC |
| XQ-527as | CATGGAGCAGCCAGTGAAGTAGATT |
| XQ-527s | TCTGTCACCCTGGGCCACCTTGTCG |
| XQ-528as | TCATGGAGCAGCCAGTGAAGTAGAT |
| XQ-528s | CTGTCACCCTGGGCCACCTTGTCGG |
| XQ-529as | TTCATGGAGCAGCCAGTGAAGTAGA |
| XQ-529s | TGTCACCCTGGGCCACCTTGTCGGA |
| XQ-530as | GTTCATGGAGCAGCCAGTGAAGTAG |

FIG. 20 (CONTINUED)

| | |
|---|---|
| XQ-530s | GTCACCCTGGGCCACCTTGTCGGAA |
| XQ-531as | GGTTCATGGAGCAGCCAGTGAAGTA |
| XQ-531s | TCACCCTGGGCCACCTTGTCGGAAT |
| XQ-532as | GGGTTCATGGAGCAGCCAGTGAAGT |
| XQ-532s | CACCCTGGGCCACCTTGTCGGAATC |
| XQ-533as | TGGGTTCATGGAGCAGCCAGTGAAG |
| XQ-533s | ACCCTGGGCCACCTTGTCGGAATCT |
| XQ-534as | CTGGGTTCATGGAGCAGCCAGTGAA |
| XQ-534s | CCCTGGGCCACCTTGTCGGAATCTA |
| XQ-535as | GCTGGGTTCATGGAGCAGCCAGTGA |
| XQ-535s | CCTGGGCCACCTTGTCGGAATCTAC |
| XQ-536as | GGATGGGTTCATGGAGCAGCCAGTG |
| XQ-536s | CTGGGCCACCTTGTCGGAATCTACT |
| XQ-537as | GGGATGGGTTCATGGAGCAGCCAGT |
| XQ-537s | TGGGCCACCTTGTCGGAATCTACTT |
| XQ-538as | CGGGATGGGTTCATGGAGCAGCCAG |
| XQ-538s | GGGCCACCTTGTCGGAATCTACTTC |

FIG. 20 (CONTINUED)

| | |
|---|---|
| XQ-539as | GCGGGATGGGTTCATGGAGCAGCCA |
| XQ-539s | GGCCACCTTGTCGGAATCTACTTCA |
| XQ-540as | AGCGGACTGGGTTCATGGAGCAGCC |
| XQ-540s | GCCACCTTGTCGGAATCTACTTCAC |
| XQ-541as | GAGCGGGATGGGTTCATGGAGCAGC |
| XQ-541s | CCACCTTGTCGGAATCTACTTCACT |
| XQ-542as | AGAGCGGGCTGGGTTCATGGAGCAG |
| XQ-542s | CACCTTGTCGGAATCTACTTCACTG |
| XQ-543as | AAGAGCGGGCTGGGTTCATGGAGCA |
| XQ-543s | ACCTTGTCGGAATCTACTTCACTGG |
| XQ-544as | AAAGAGCGGGCTGGGTTCATGGAGC |
| XQ-544s | CCTTGTCGGAATCTACTTCACTGGC |
| XQ-545as | AAAAGAGCGGGCTGGGTTCATGGAG |
| XQ-545s | CTTGTCGGAATCTACTTCACTGGCT |
| XQ-546as | CAAAAGAGCGGGCTGGGTTCATGGA |
| XQ-546s | TTGTCGGAATCTACTTCACTGGCTG |
| XQ-547as | CCAAAAGAGCGGGCTGGGTTCATGG |
| XQ-547s | TGTCGGAATCTACTTCACTGGCTGC |

FIG. 20 (CONTINUED)

| | |
|---|---|
| XQ-548as | GCCAAAAGAGCGGGCTGGGTTCATG |
| XQ-548s | GTCGGAATCTACTTCACTGGCTGCT |
| XQ-549as | GGCCAAAAGAGCGGGCTGGGTTCAT |
| XQ-549s | TCGGAATCTACTTCACTGGCTGCTC |
| XQ-550as | GGGCCAAAAGAGCGGGCTGGGTTCA |
| XQ-550s | CGGAATCTACTTCACTGGCTGCTCC |
| XQ-551as | AGGGCCAAAAGAGCGGGCTGGGTTC |
| XQ-551s | GGAATCTACTTCACTGGCTGCTCCA |
| XQ-552as | CAGGGCCAAAAGAGCGGGCTGGGTT |
| XQ-552s | GAATCTACTTCACTGGCTGCTCCAT |
| XQ-553as | GCAGGGCCAAAAGAGCGGGCTGGGT |
| XQ-553s | AATCTACTTCACTGGCTGCTCCATG |
| XQ-554as | CGCAGGGCCAAAAGAGCGGGCTGGG |
| XQ-554s | ATCTACTTCACTGGCTGCTCCATGA |
| XQ-555as | CCGCAGGGCCAAAAGAGCGGGCTGG |
| XQ-555s | TCTACTTCACTGGCTGCTCCATGAA |
| XQ-556as | ACCGCAGGGCCAAAAGAGCGGGCTG |

FIG. 20 (CONTINUED)

| | |
|---|---|
| XQ-556s | CTACTTCACTGGCTGCTCCATGAAC |
| XQ-557as | CACCGCAGGGCCAAAAGAGCGGGCT |
| XQ-557s | TACTTCACTGGCTGCTCCATGAACC |
| XQ-558as | CCACCGCAGGGCCAAAAGAGCGGGC |
| XQ-558s | ACTTCACTGGCTGCTCCATGAACCC |
| XQ-559as | ACCACCGCAGGGCCAAAAGAGCGGG |
| XQ-559s | CTTCACTGGCTGCTCCATGAACCCA |
| XQ-560as | GACCACAGCAGGGCCAAAAGAGCGG |
| XQ-560s | TTCAATGGCTGCTCCATGAACCCAG |
| XQ-561as | TGACCACCGCAGGGCCAAAAGAGCG |
| XQ-561s | TCACTGGATGCTCCATGAACCCAGC |
| XQ-562as | ATGACCACCGCAGGGCCAAAAGAGC |
| XQ-562s | CACTGACTGCTCCATGAACCCAGCC |
| XQ-563as | CATGACCACCGCAGGGCCAAAAGAG |
| XQ-563s | ACTGGATGCTCCATGAACCCAGCCC |
| XQ-564as | TCATGACCACCGCAGGGCCAAAAGA |
| XQ-564s | CTGGATGCTCCATGAACCCAGCCCG |
| XQ-565as | TTCATGACCACCGCAGGGCCAAAAG |

FIG. 20 (CONTINUED)

| | |
|---|---|
| XQ-565s | TGGATGCTCCATGAACCCAGCCCGC |
| XQ-566as | ATTCATGACCACCGCAGGGCCAAAA |
| XQ-566s | GGATGCTCCATGAACCCAGCCCGCT |
| XQ-567as | GATTCATGACCACCGCAGGGCCAAA |
| XQ-567s | GCTGCTCCATGAACCCAGCCCGCTC |
| XQ-568as | CGATTCATGACCACCGCAGGGCCAA |
| XQ-568s | CTGCTCCATGAACCCAGCCCGCTCT |
| XQ-569as | CCGATTCATGACCACCGCAGGGCCA |
| XQ-569s | TGCTCCATGAACCCAGCCCGCTCTT |
| XQ-570as | ACCGATTCATGACCACCGCAGGGCC |
| XQ-570s | GCTCCATGAACCCAGCCCGCTCTTT |
| XQ-571as | AACCGATTCATGACCACCGCAGGGC |
| XQ-571s | CTCCATGAACCCAGCCCGCTCTTTT |
| XQ-572as | GAACCGATTCATGACCACCGCAGGG |
| XQ-572s | TCCATGAACCCAGCCCGCTCTTTTG |
| XQ-573as | TGAACCGATTCATGACCACCGCAGG |
| XQ-573s | CCATGAACCCAGCCCGCTCTTTTGG |

FIG. 20 (CONTINUED)

| | |
|---|---|
| XQ-574as | CTGAACCGATTCATGACCACCGCAG |
| XQ-574s  | CATGAACCCAGCCCGCTCTTTTGGC |
| XQ-575as | GCTGAACCGATTCATGACCACCGCA |
| XQ-575s  | ATGAACCCAGCCCGCTCTTTTGGCC |
| XQ-576as | GGCTGAACCGATTCATGACCACCGC |
| XQ-576s  | TGAACCCAGCCCGCTCTTTTGGCCC |
| XQ-577as | GGGCTGAACCGATTCATGACCACCG |
| XQ-577s  | GAACCCAGCCCGCTCTTTTGGCCCT |
| XQ-578as | GGGGCTGAACCGATTCATGACCACC |
| XQ-578s  | AACCCAGCCCGCTCTTTTGGCCCTG |
| XQ-579as | CGGGGCTGAACCGATTCATGACCAC |
| XQ-579s  | ACCCAGCCCGCTCTTTTGGCCCTGC |
| XQ-580as | GCGGGGCTGAACCGATTCATGACCA |
| XQ-580s  | CCCAGCCCGCTCTTTTGGCCCTGCG |
| XQ-581as | AGCGGGGCTGAACCGATTCATGACC |
| XQ-581s  | CCAGCCAGCTCTTTTGGCCCTGCGG |
| XQ-582as | GAGCGGGGCTGAACCGATTCATGAC |
| XQ-582s  | CAGCCCGCTCTTTTGGCCCTGCGGT |

FIG. 20 (CONTINUED)

| | |
|---|---|
| XQ-583as | TGAGCGGGGCTGAACCGATTCATGA |
| XQ-583s  | AGCCCGCTCTTTTGGCCCTGCGGTG |
| XQ-584as | GTGAGCGGGGCTGAACCGATTCATG |
| XQ-584s  | GCCCGCTCTTTTGGCCCTGCGGTGG |
| XQ-585as | AGTGAGCGGGGCTGAACCGATTCAT |
| XQ-585s  | CCCGCTCTTTTGGCCCTGCGGTGGT |
| XQ-586as | CAGTGAGCGGGGCTGAACCGATTCA |
| XQ-586s  | CCGCTCTTTTGGCCCTGCGGTGGTC |
| XQ-587as | CCAGTGAGCGGGGCTGAACCGATTC |
| XQ-587s  | CGCTCTTTTGGCCCTGCGGTGGTCA |
| XQ-588as | CCCAGTGAGCGGGGCTGAACCGATT |
| XQ-588s  | GCTCTTTTGGCCCTGCGGTGGTCAT |
| XQ-589as | ACCCAGTGAGCGGGGCTGAACCGAT |
| XQ-589s  | CTCTTTTGGCCCTGCGGTGGTCATG |
| XQ-590as | AACCCAGTGAGCGGGGCTGAACCGA |
| XQ-590s  | TCTTTTGGCCCTGCGGTGGTCATGA |
| XQ-591as | AAACCCAGTGAGCGGGGCTGAACCG |

FIG. 20 (CONTINUED)

| | |
|---|---|
| XQ-591s | CTTTTGGCCCTGCGGTGGTCATGAA |
| XQ-592as | AAAACCCAGTGAGCGGGGCTGAACC |
| XQ-592s | TTTTGGCCCTGCGGTGGTCATGAAT |
| XQ-593as | GAAAACCCAGTGAGCGGGGCTGAAC |
| XQ-593s | TTTGGCCCTGCGGTGGTCATGAATC |

Oligonucleotide chip assay

Automated nucleic acid sequencing assay (ABI PRISM)

MUTATED AQP, METHOD FOR DETECTING CANCER USING THE SAME, DNA CHIP HAVING OLIGONUCLEOTIDES OF SAID MUTATED AQP SEQUENCE

TECHNICAL FIELD

The present invention relates to mutant aquaporin (AQP) gene, a method for detecting cancer by using the mutant and expression thereof; and DNA chip having oligonucleotides of said mutated AQP sequence.

BACKGROUND ART

Neoplastic diseases, including most: particularly the collection of diseases known as cancer, are major cause of mortality and morbidity of human and are the most difficult disease to treat. Although medical science and natural science has recently advanced so much, cancer still remains unresolved problem. In United States of America, cancer is surpassed only by cardiovascular diseases as the primary cause of adult death, one million and three hundred thousands of new cases of cancer develop yearly and five hundred and fifty thousands of men die of cancer every year. This means that one of every 2 or 3 American people falls victim to cancer. The four major cancers in United States of America include lung cancer, colorectal cancer, prostate cancer and breast cancer, and the risk of American people to get these 4 major cancer are shown in Table 1 (Bang Y J et al. Cancer: Current Diagnosis and Therapy. Hanuri Company:Seoul, 1999;69-107)

TABLE 1

The risk of American men to get four major cancers (from National Cancer Institute of United States, SEER Data)

| Type of cancer | Sex | Risk of getting cancer (%) | Risk of dying of cancer (%) |
|---|---|---|---|
| Lung cancer | Male | 8.6 | 7.1 |
|  | Female | 5.4 | 4.2 |
| Colorectal cancer | Male | 6.2 | 2.6 |
|  | Female | 5.9 | 2.6 |
| Prostate cancer | Male | 18.5 | 3.6 |
| Breast cancer | Female | 12.6 | 3.6 |

The mechanism of development of human cancer is being clarified in more detail owing to advances of molecular biology and genetics; especially human genome project, functional genomics, nanotechnology and bioinformatics. Cancer is genetic disease, ie. Cancer develops secondary to genetic abnormality. Acquired genetic abnormality secondary to chemical carcinogen, UV light, irradiation or virus and hereditary genetic abnormality induces change (ie, mutation) into genetic information (DNA, RNA) of genome. When these mutation activate oncogenes and inactivate tumor suppressor genes, cancers may develop. Oncogene and tumor suppressor genes play key roles in regulation of signal transduction, cell cycle progression, cellular death and survival, accommodation with neighbor cells and angiogenesis is. Oncogenes induce proliferation, survival and escape from death, invasion of adjacent tissues and angiogenesis and thus stimulate development of cancer, whereas, tumor suppressor genes counteract oncogenes and thus inhibit development of cancer (Evan G et al. Matter of life and cell death, Science (1998) 281, 1317-1322; Harrington E A et al. Oncogene and cell death. Curr Opin Genet Dev (1994) 4, 120-129).

During the past twenty years, many medical scientists have focused on oncogenes and tumor suppressor genes and have tried to find genetic markers of cancer and tumor markers through investigation of oncogenes and tumor suppressor genes. Through these research, they have found important genes such as p53, Rb, p16 and other CDK inhibitors, which regulate cell cycle and cellular apoptosis (Macleod K et al. Tumor suppressor genes. Curr Opin Genet Dev (2000) 10, 81-93; Adams P D et al. Negative control elements of the cell cycle in human tumors. Curr. Opin. Cell. Biol. (1998); 10, 791-797), BRCA1 and BRCA2 which are closely related with hereditary breast cancer and hereditary ovarian cancer (Miki Y et al. A strong candidate for the breast and ovarian susceptibility gene BRCA1, Science (1994) 266, 66-71); Wooster R et al. Identification of the breast cancer susceptibility gene BRCA2. Nature (1995) 378, 789-792), and APC gene which is closely related with hereditary colorectal cancer (Kinzier K, et al, Lessons from hereditary colorectal cancer, Cell (1996) 87, 159-170). These findings, had greatly contributed to progress of cancer research. In addition, these research stimulated establishment of many research centers which tested specific gene mutation on a commercial basis, in particular, BRCA1 and BRCA2 in women with high risk of development of breast cancer and ovarian cancer owing to family history (Levine A J. p53, the cellular gatekeeper for growth and division, Cell(1997), 88, 323-331; Frank T S. Laboratory. identification of hereditary risk of breast and ovarian cancer, Curr. Opin. Biotech. (1999) 10, 289-294).

However, ideal genetic marker remains not to be found for acquired solid tumors which constitute most of human cancers. In addition, no molecular marker common to all human cancer has been found so far. It is p53 gene that shows highest frequency of mutation in all forms of human cancer, but even for p53 gene, the frequency of mutation or deletion is only 30 to 50%, which suggests that p53 is inappropriate for use as a molecular diagnostic marker of human cancer in clinical practice (Levine A J et al. p53, the cellular gatekeeper for growth and division, Cell (1997) 88, 323-331). Oligonucleotide DNA chip which detects mutation of p53 gene has recently been tested in patients with lung cancer, but only 40% of the lung cancer tissues showed mutation of p53 gene, which indicates limitation of analysis of mutation of p53 gene as a diagnostic tool of lung cancer (Ahrendt S A et al. Rapid p53 sequence analysis in primary lung cancer using an oligonucleotide probe array, Proc Natl Acad Sci U.S.A (1999) 96, 7382-7387). So far, no marker has been found to be of practical value for the clinical management of lung cancer, stomach cancer, colorectal cancer and breast cancer which form more than 50% of all human cancers.

Affymetrix company (www.affymetrix.com) has recently manufactured Human Cancer G110 Array, a new type complementary DNA(cDNA) chip which detects expression of about 100 oncogenes and tumor suppressor genes which have been found so far. However, it is questionable whether this DNA chip pan detect all human cancer, due to the fact that the genes found so far are at most 5-10% of the genes related to all human cancer.

Despite progress of surgery, chemotherapy, radiation therapy and immunotherapy, the success rate of treatment of human cancer except some hematologic cancer and childhood malignancies has not been remarkably improved during last several decades. The main reason for the poor treatment outcome of human cancer lies in the delayed diagnosis of cancer in advanced status when it has already metastasized and cure is hard to attain rather than limited efficacy of current therapy for cancer. Nowadays the prevention of cancer takes a key place in clinical science as does treatment of cancer.

Primary method of cancer prevention is so called chemoprevention which aims to delay or inhibit multistep development of cancer by change of life style, diet or drugs. The chemoprevention is appropriate in particular for asymptomatic people with high risk of cancer because of family history or past medical history of cancer. For example, a clinical study of chemoprevention is under way to administer retinoic acid to patients in status of long term remission from lung cancer after therapy. However, we still do not exactly know either the etiology of cancer (except smoking) or effective chemopreventive drugs, and we have no reliable marker to identify the efficacy of chemopreventive agents, all of which limit the practical value of chemoprevention of cancer.

The secondary method of cancer prevention is early detection or screening of cancer. The fate of individual cancer patient, ie. cure rate and long term survival, is primarily determined by volume and stage of tumor at the time of diagnosis; The cure rate and survival rate is highest among cancers in stage 1 or stage 2. In fact, we can expect cure of cancer only when it is diagnosed in early stage, ie. stage 1 and/or stage 2. Therefore, medical society makes every effort to detect cancer from the general public in early stage. Screening methods of cancer include inspection (skin, oral cavity, external genitalia, uterine, cervix), palpation (breast, oral cavity, thyroid, anus and rectum, prostate, testicle, uterus, lymph nodes), clinical chemistry tests such as, Papanicolaou smear and tumor markers including serum prostate specific antigen (PSA) or α-feto protein, radiologic study such as barium enema study of colon, chest X ray, and endoscopic examination. Table 2 shows the cancer screening methods recommended by American Cancer Society.

TABLE 2

Cancer screening methods: Guideline recommended by American Cancer Society (1993).

| Target Cancer | Screening method | Sex | Age of screening population | Screening frequency |
|---|---|---|---|---|
| Prostate cancer | Digital rectal examination | Male | 50 years or after | yearly |
| | Serum PSA assay | Male | 50 years or after | Yearly |
| Breast cancer | Self examination | Female | 20 years or after | monthly |
| | Clinical breast examination | Female | 20-40 years/ 40 years or after | Every 3 years/ Yearly |
| | Mammography | Female | 50 years or after | Yearly |
| Colorectal cancer | Stool occult blood test | Male and female | 50 years or after | Yearly |
| | Colonoscopy | Male and female | 50 years or after | Every 3 to 5 years |
| Uterine cervix cancer | Pap smear | Female | 18 years or after | Yearly |
| | Pelvix examination | Female | 18-40 years/ 40 years or after | Every 1-3 years/ Yearly |
| | Endometrial biopsy | Female | Postmenopausal, High risk women | Depending on doctor's recommendation |
| Lung cancer | Chest X ray Sputum cytology | Not recommended as a routine study | | |

The cancer screening tests listed in Table 2 have been shown actually to improve the treatment outcome of target cancers. In particular, serum PSA assay is widely used for the screening, diagnosis, follow up after therapy of prostate cancers (Rimer B K et al. Cancer Screening. In DeVita V T Jr, Hellman S, Rosenberg S A. eds. Cancer. Principles and Practice of Oncology. fifth ed., Lippincott-Rave:Philadelphia, 1997; 619-631).

Detection of expression of specific gene in blood has recently been used to identify specific cells and diagnosis of specific diseases, especially cancer. For example, detection of benign or malignant prostatic epithelial cells which express PSA or prostate specific membrane antigen (PSMA) from blood by using reverse transcription, polymerase chain reaction (RT-PCR) assay has been shown to be of value for the staging of cancer, ie. detection of metastatic cancer (which has been called molecular staging) as well as diagnosis of prostatic cancer. Presence of cancer cells within blood does not indicate metastasis by itself, but highly suggests metastasis (Katz A E et al. Molecular staging of prostate cancer with the use of an enhanced reverse transcriptase-PCR assay; Israeli R S et als. Sensitive nested reverse transcription polymerase chain reaction detection of circulating prostatic tumor cells: comparison of prostate specific membrane antigen and prostate specific antigen-based assays. Cancer Research (1994) 54: 6306). However, no pan-tumor molecular marker has been found so far which show abnormality in most human cancers and thus is of practical value for the diagnosis and staging of cancer in clinical practice.

Lung cancer ranks the first of all human cancers both in the incidence and death rates in United States of America: About 180,000 new cases of lung cancer develop yearly, about 160,000 patients die of lung cancer and overall 5-year survival rate of patients with lung cancer is only around 10%. Most of human lung cancers are bronchogenic carcinomas, which is primarily classified into small cell carcinoma and non-small cell carcinoma. The small cell carcinomas are a single type, while the non-small cell carcinomas consist of adenocarcinoma, squamous cell carcinoma, large cell carcinoma, bronchioalveolar carcinoma. Primary cause of lung cancer is smoking and the amount and duration of smoking is directly correlated with incidence and death rates of lung cancer.

The risk of getting lung cancer increases twenty-folds and risk of death of lung cancer becomes 13% on smoking 25 cigarettes daily for 10 years. Of remark is that the risk of lung cancer increases not only in primary or direct smokers but also in secondary or indirect smokers. The screening for lung cancer is indicated both in primary smokers and secondary smokers and also in men who had been exposed to lung carcinogen such as asbestos.

Classical methods for the screening of lung cancer include chest radiography (simple X ray) and sputum cytology examination, however the former and the latter has a diagnostic sensitivity for lung cancer of only 30% and 40-60%, respectively. It is hard for these two studies to detect lung cancer in early stage and to significantly improve treatment outcomes of lung cancer, and for this reason these two studies were excepted from a list of recommended screening tests for cancers by American Cancer Society.

Owing to lack of effective screening methods, ninety percent of cases of lung cancer are nowadays diagnosed in advanced status(stage III or IV), in which cases most of the patients die within 2 years after diagnosis and 5 year survival rate is less than five percent despite aggressive chemotherapy and irradiation therapy (Choi S J et al. eds. Lung: neoplasia and cancer. In Current Diagnosis and Therapy. Han-Uri Publishing Co.:Seoul. 1999;323-332). In contrast, if lung cancer can be detected by screening study in occult carcinoma status when patient has no symptoms and radiologic study of the lung shows no cancerous lesion, the cure rate of cancer is more than eighty percent. In fact some reports showed evidence that treatment outcomes of lung cancer are remarkably improved even by limited classical screening study of chest radiography and sputum cytology examination and that there were significant differences in 5 year survival rate between lung cancers detected by screening study (35%) and those diagnosed by lung cancer-related symptoms (13%) (Berlin N I et al. Early lung cancer detection: Summary and conclusions, American Review of respiratory diseases (1984) 30, 565).

Diagnostic study and follow up study after therapy of lung cancer leaves much room for improvement. Accurate diagnosis of lung cancer is in reality not easy. It is hard to detect early stage lung cancer by chest X ray and sputum cytology examination and, even after detection of lung mass, it is not easy to differentiate between lung cancer and benign lung mass and between primary lung cancer and metastatic lung cancer. Definitive diagnosis of lung cancer is usually made by bronchoscopic biopsy, brush biopsy, bronchoalveolar lavage cytology examination, percutaneous needle aspiration cytology examination, mediastinoscopic biopsy, lymph node biopsy or pleural biopsy, but sometimes requires even open lung biopsy. The diagnosis is often ambiguous even after radiologic study and biopsy, in particular for solitary pulmonary nodules with diameter of less than 5 mm as being important in clinic (Ginsberg R J et al. Cancer of the lung. Section 2. Non-small cell lung cancer. In DeVita V T Jr. Hellman S, Rosenberg S A. eds. Cancer. Principles and Practice of Oncology, 5th ed., Lippincott-Raven: Philadelphia, 1997; 858-910).

The next step after diagnosis of lung cancer is staging work up, ie., study of extent of cancer. The conventional staging methods for lung cancer include: computerized tomography (CT) scan, bronchoscopy, thoracoscopy, mediastinoscopy, and biopsy and cell examination using them, but all of these methods have limited accuracy and endoscopic studies are invasive. Lung cancer commonly invades pleura band and thus induce pleural effusion, in which cases, pleural fluid cytology examination and/or pleural biopsy are performed to identify the cause of pleural effusion, but reveals definitive diagnosis in only about half of the cases. Therefore, staging method for lung cancer definitely leaves much room for improvement.

The appropriate follow up study is essential after therapy for lung cancer which can accurately define the results of therapy, detect residual or recurrent cancer in a sensitive and rapid way. The current follow Up study of lung cancer include radiologic study such as CT scan and endoscopic examination, but it is almost impossible to detect microscopic residual or recurrent cancer by these study. Therefore, novel method for follow up of lung cancer is urgently necessary.

Appropriate maintenance of membrane water permeability is a fundamental requirement of all living organisms. Aquaporin (AQP) is a family of water channel proteins of membranes through which water are transported into and out of cells. AQP exists in all type of living organisms which include microorganisms, plants, mammalians. Ten types of mammalian AQP, ie., from type 1 to type 10 AQP, have been identified so far, whereas, more than 100 types of AQP exist in plants in which transport of water are more critical for the survival than in mammalians. AQP1 was the first type to be isolated in erythrocytes. Human type AQP1 was cloned for the first time by one of the present inventors (Moon C et als. Cloning of human aquaporin 1 gene, J Biol Chem (1993) 268, 15772-15778). Two functional groups of AQP are now being recognized. The first, including AQP1, AQP2, AQP4, AQP5, AQP6, AQP8 and AQP10 are permeable only to water, as classically defined. A second group, including AQP3, AQP7 and AQP9 are highly permeable to water, but also are permeable by glycerol (King L S et al. Aquaporin in health and disease, Molecular Medicine Today (2000) 6, 60-65). The present inventors have recently found the evidence that AQP also plays important roles in cell cycle regulation, signal transduction, delayed early response to growth factors, and gas exchange in hypoxic condition.

AQP proteins exist in cell membranes, and to adapt to water channel function, its structure has six transmembrane domains and five connecting loops (loop A-E). The. Amino terminal (NH2 terminal) and carboxy terminal (COOH terminal) portion of AQP are located inside cytoplasm. Loop B and E of AQP contains signature motif Asn-Pro-Ala, which is called NPA, and adjacent cysteine. Two NPA motifs and cysteine combine to become center of the water channel (Walz T et als. Three-dimensional electron density map of human aquaporin 1 at 6 A resolution. Nature (1997) 387, 624-627; Lee M D et al. The human aquaporine-5 gene. J. Biol. Chem (1996) 271, 8599-8604).

Each type of 10 mammalian aquaporins has a distinct tissue and cellular distribution and plays a diverse and specific role depending on the type of tissues and cells where it is located. AQP1 is located in erythrocytes, kidney, lung, eye, choroid plexus, biliary tract, nonfenestrated endothelia. AQP1 is abundant in proximal tubules and descending thin limb of Henle's loop segments, actively reabsorbs most of glomerular, filtrate and thus greatly contributes to concentration of urine. AQP2 is located in collecting duct epithelia of kidney, secreted in response to stimulation of antidiuretic hormone and thus contribute to concentration of urine. Deficiency of AQP2 produces nephrogenic diabetes insipidus which is characterized by failure to concentrate urine. AQP3 is located in renal collecting duct, gastrointestinal tract, airway epithelia, corneal epithelium and brain. AQP4 is abundant in glial cells and ependymal cell of brain tissue, but is also located in retina and airway epithelia. AQP5 is located in salivary gland, lacrimal gland and lung, in which plays an important role in production of saliva, tear and airway secretions. AQP6 is located in proximal tubular epithelia and collecting duct epithelia of kidney and characteristically acts as intracellular water channel and also is involved in regulation of acid base balance. AQP7 and AQP8 are expressed in germ cells and sperms. AQP9 is abundant in adipocytes (Deen P R T et al. Epithelial aquaporins., Current Opinion in Cell Biology (1999) 10, 435-442; King L S et al. Aquaporin in health and disease, Molecular Medicine Today (2000) 6, 60-65; Agre P. Aquaporin water channels in kidney. J. American Society of Nephrology (2000) 11, 764-777).

AQP plays important roles particularly in kidney, lung, brain, eye and eythrocytes. The lung has exceptionally high epithelial and endothelial permeability. Appropriate removal and supply of water in the airway, vascular and interstitial compartments of the lung are essential for normal gas exchange and lung defence. AQP is actively involved in the maintenance of liquid layer of surface of airway epithelia, which is essential for normal mucosal ciliary action, and also involved in appropriate supply of water to airway which prevents dehydration of airway and ensures adequate dehydration of expired air. Four water channels, including AQP1, AQP3, AQP4 and AQP5 have been indentified in the lung of rats and mice. AQP1 (Genebank No. NM-000385) is abundant in apical and basolateral membrane, of microvasculature and pleural membrane. AQP5 (Genebank No. NM-001651) is abundant in apical membrane of type 1 alveolar pneumocytes and secretory cells of airway submucosal gland. AQP3 (Genebank No. NM-004925) and AQP4 (Genebank No. U63623) are expressed in epithelial cells of airway and nasopharynx. AQP is also reported to be involved in $CO_2$ exchange of alveolar cells, which suggest that AQP may act as a gas channel (Nielsen S et al. Aquaporin in complex tissue II., Cellular and subcellular distribution in respiratory tract and glands of rat., American J. Physiology (1997) 273, 1549-1561; King L S et al. Aquaporin-1 water channel protein in lung: ontogeny, steroid-induced expression, and distribution in rat., J. Clin Invest (1996) 97, 2183-2191). However, distribution and function of each type of AQP in the human lung remain to be indefinite. In addition, role of AQP in human cancer, in particular lung cancer, remains to be indefinite.

Considering the prior art up to now, there is a need for the development of new tumor markers, which is useful for screening, diagnosis, and follow-up study after treatment for human cancer including lung cancer.

DISCLOSURE OF INVENTION

Based on the background information as summarized in the above, inventors have carried out extensive study and have found that analysis of mutation or expression of AQP is invaluable for the accurate, efficient and rapid detection of cancer and the present invention is based on these findings.

Therefore, the object of the present invention is to provide information on mutant AQP5 gene by which we can detect cancers.

It is another object of the present invention to provide a method for detecting cancer in quick, efficient and accurate ways by using analysis of mutation of AQP5 and expression of AQPs.

It is a further object of the present invention to provide DNA chip (microarray) on which oligonucleotides of AQP5 are arrayed.

In A: antisense probe of aquaporin type 1 (AQP1) was used,

In B: sense probe of AQP1 was used,

In C: antisense probe of aquaporin type 5 (AQP5) was used,

In D: sense probe of AQP5 was used,

In E: antisense probe of aquaporin type 3 (AQP3) was used,

In F: sense probe AQP3 was used,

In G: antisense probe of aquaporin type 4 (AQP4) was used,

In H: sense probe of AQP4 was used.

Figure 2:
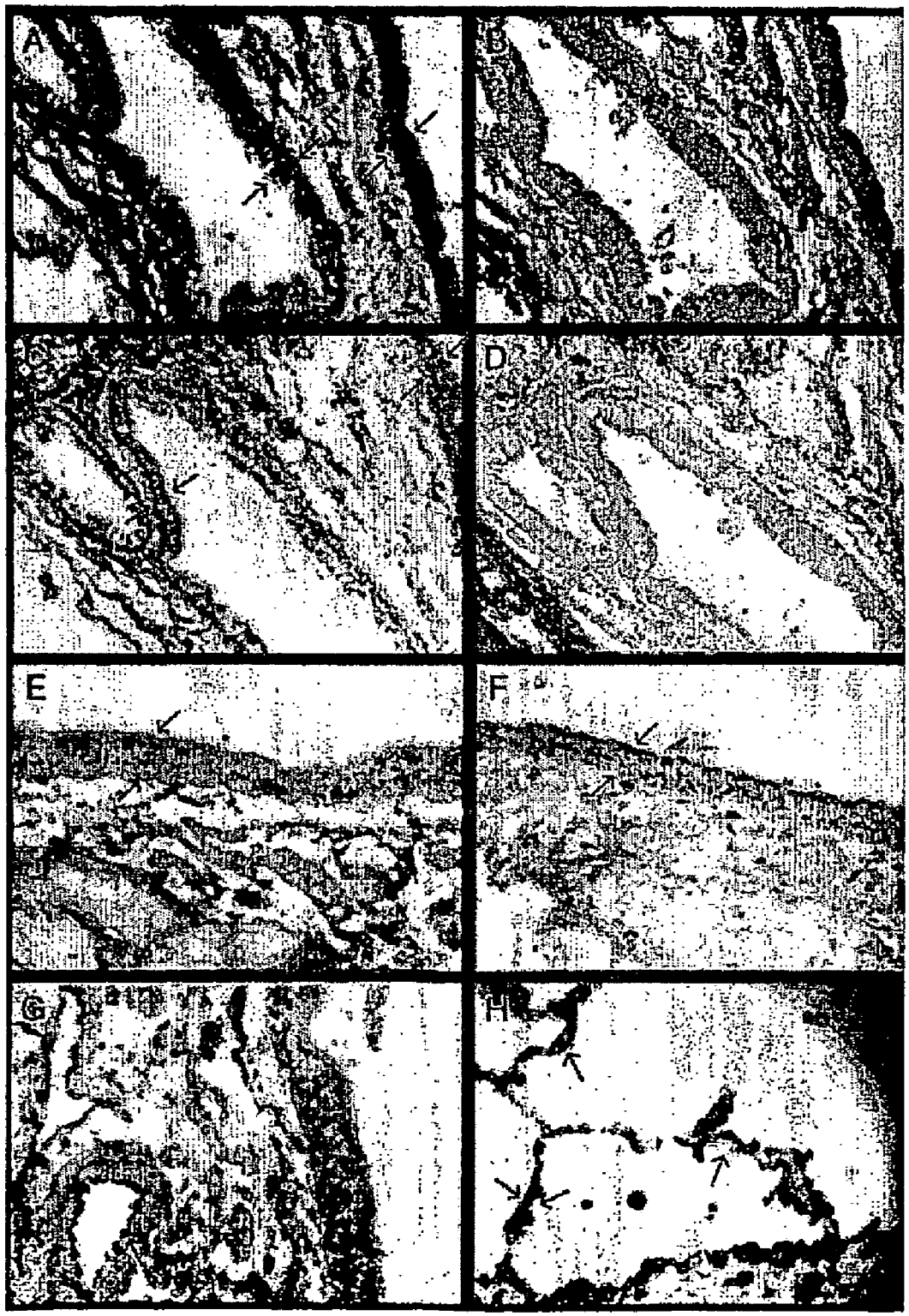

FIG. 2 illustrates expression of aquaporin (AQP) gene in bronchial and airway tissues of 17-week old male infant by using in situ hybridization methodology.

Figure 3:
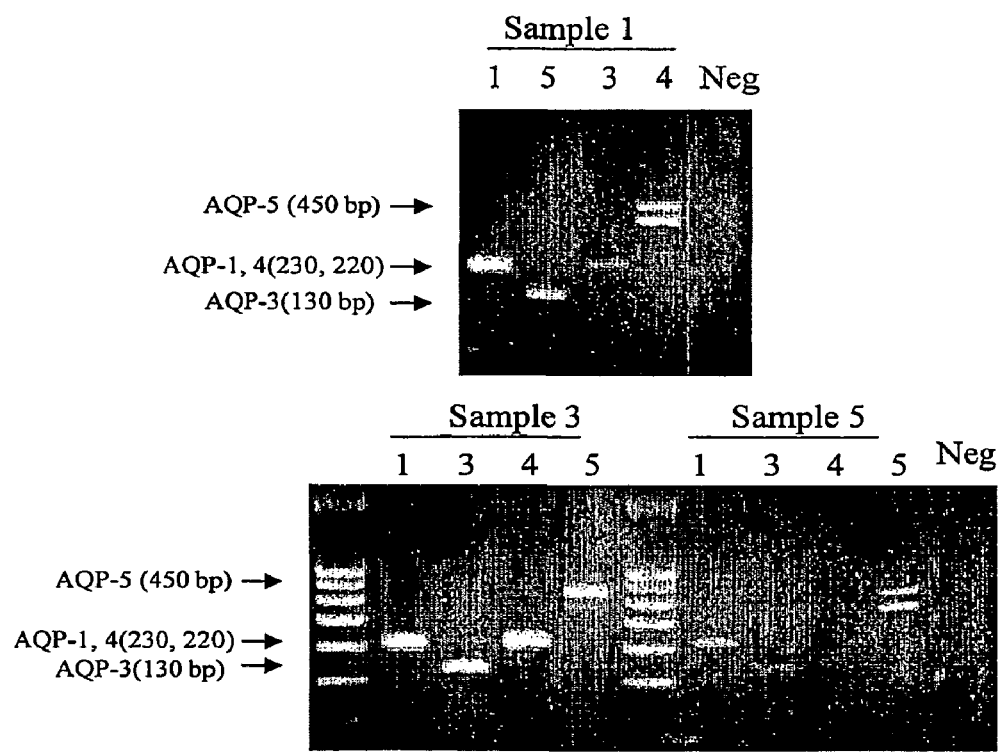

In A and B, antisense probe of AQP1 and sense probe of AQP1 was used for the study of bronchial epithelium and developing bronchiolar structure, respectively, In C and D, antisense probe of AQP1 and sense probe of AQP1 was used for the study of immature alveolar structure, respectively, In E and F, antisense probe of AQP5 and sense probe of AQP5 was used for the study of bronchial epithelium and developing bronchiolar structure, respectively, In G and H, antisense probe of AQP5 and sense probe of AQP5 was used for the study of immature alveolar structure, respectively, FIG. 3 illustrates expression of aquaporin gene family in bronchial tissues of 3 men with history of smoking as analyzed by reverse transcription polymerase chain reaction (RT-PCR) assay. Products of RT-PCR were shown on gel electrophoresis.

1: AQP1
3: AQP3
4: AQP4
5: AQP5

The sample number indicates serial number of man under study.

Figure 4:
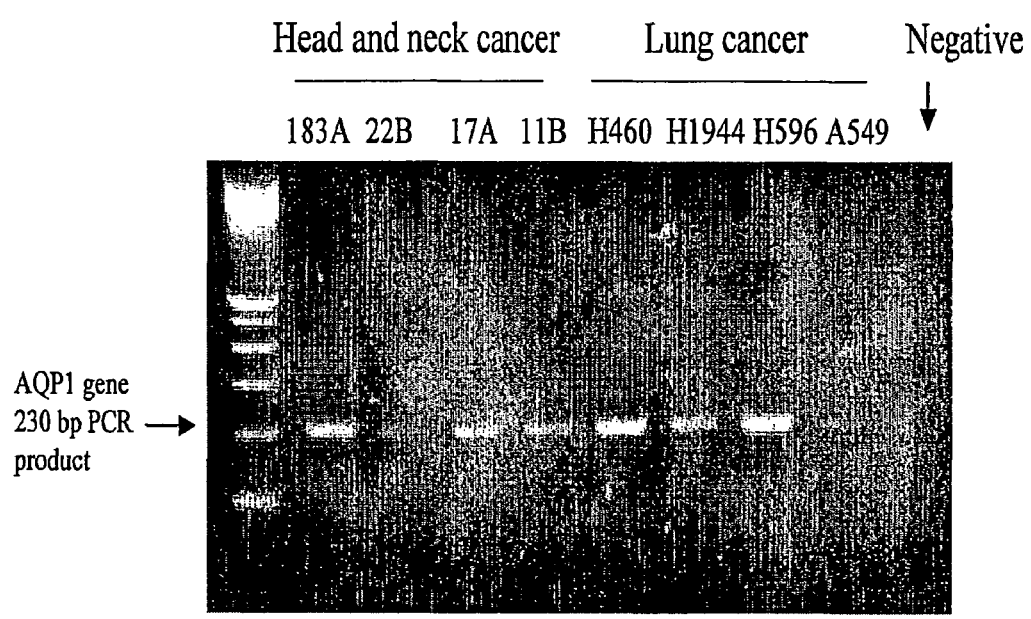

FIG. 4 illustrates expression of AQP1 gene in human head and neck cancer cell lines and human lung cancer cell lines as analyzed by RT-PCR. Products of RT-PCR were identified on gel electrophoresis.

Figure 5:
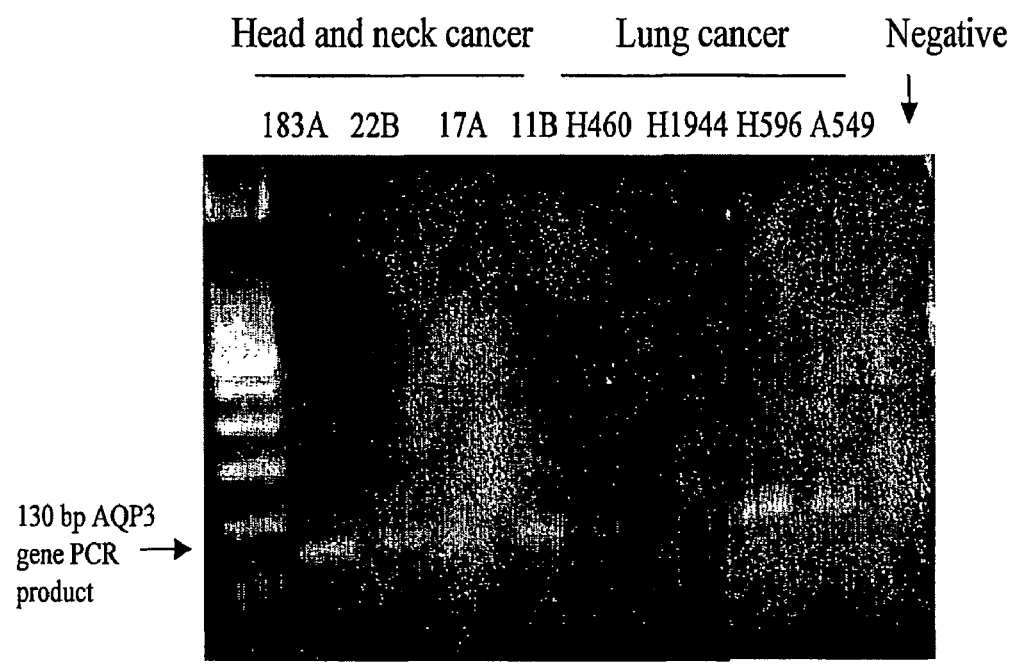

FIG. 5 illustrates expression of AQP3 in human head and neck cancer cell lines and human lung cancer cell lines as analyzed by RT-PCR. Products of RT-PCR are shown on gel electrophoresis.

Figure 6:
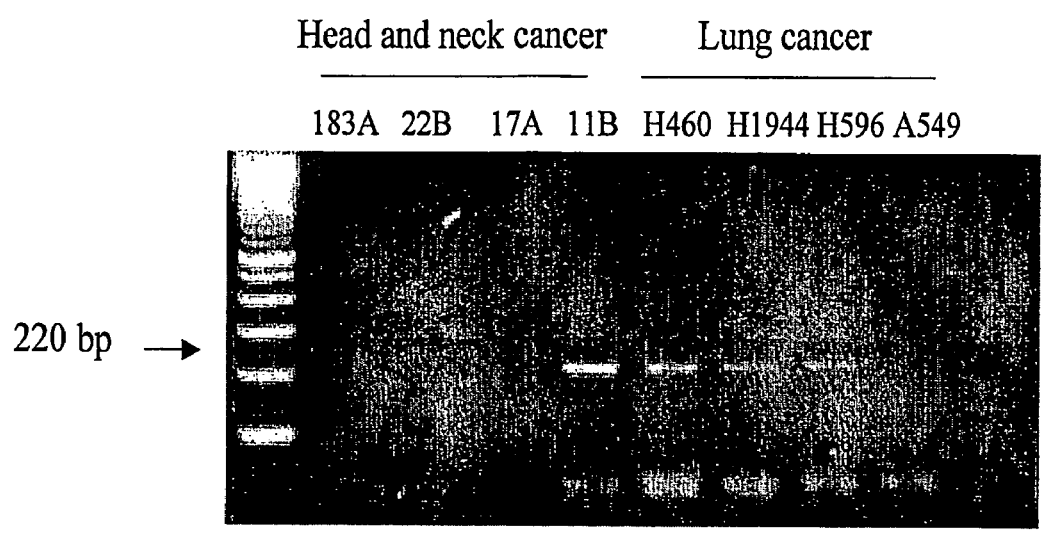

FIG. 6 illustrates expression of AQP4 in human head and neck cancer cell lines and human lung cancer cell lines as analyzed by RT-PCR. Products of RT-PCR are shown on gel electrophoresis.

Figure 7:
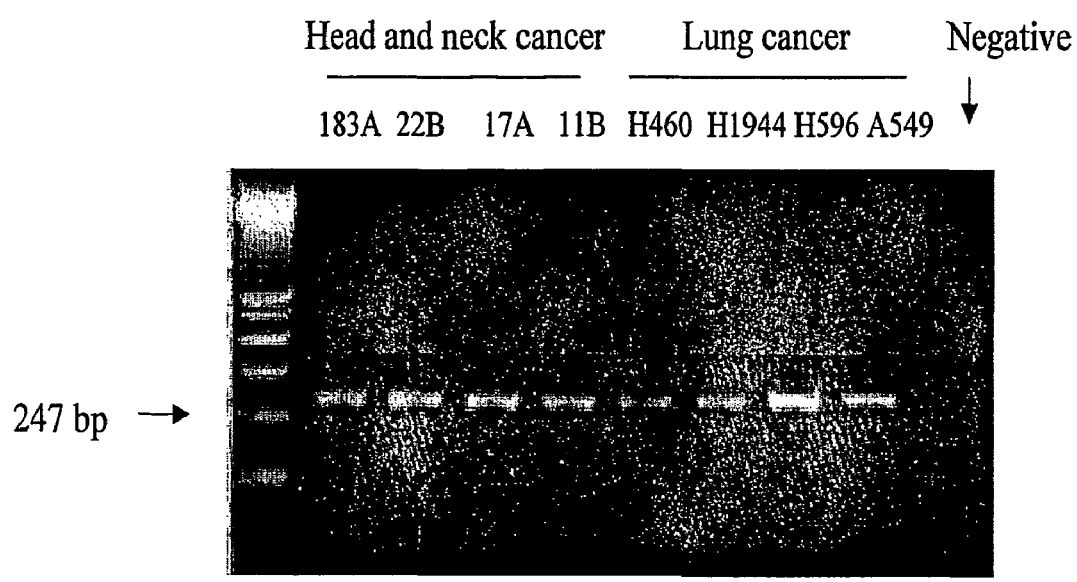

FIG. 7 illustrates expression of AQP5 in human head and neck cancer cell lines and human lung cancer cell lines as analyzed by RT-PCR. Products of RT-PCR are shown on gel electrophoresis.

Figure 8:
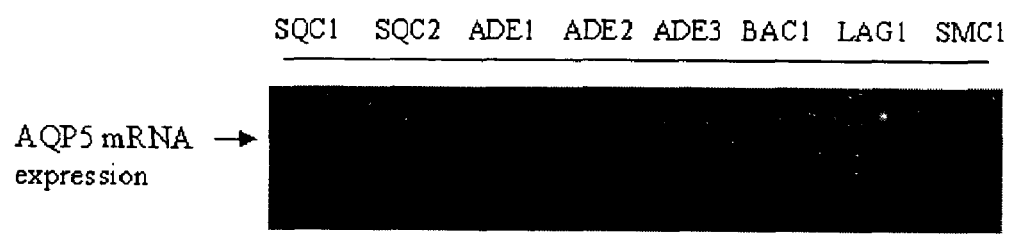

FIG. 8 illustrates expression of AQP5 in human lung cancer tissues as analyzed by Nothern blotting. SQC1 and SQC2 indicate tissue of squamous cell carcinoma, ADE1, ADE2 and ADE3 adenocarcinoma, BAC1 bronchioalveolar carcinoma, LAG large-cell carcinoma, and SMC1 small cell carcinoma, respectively.

Figure 9:
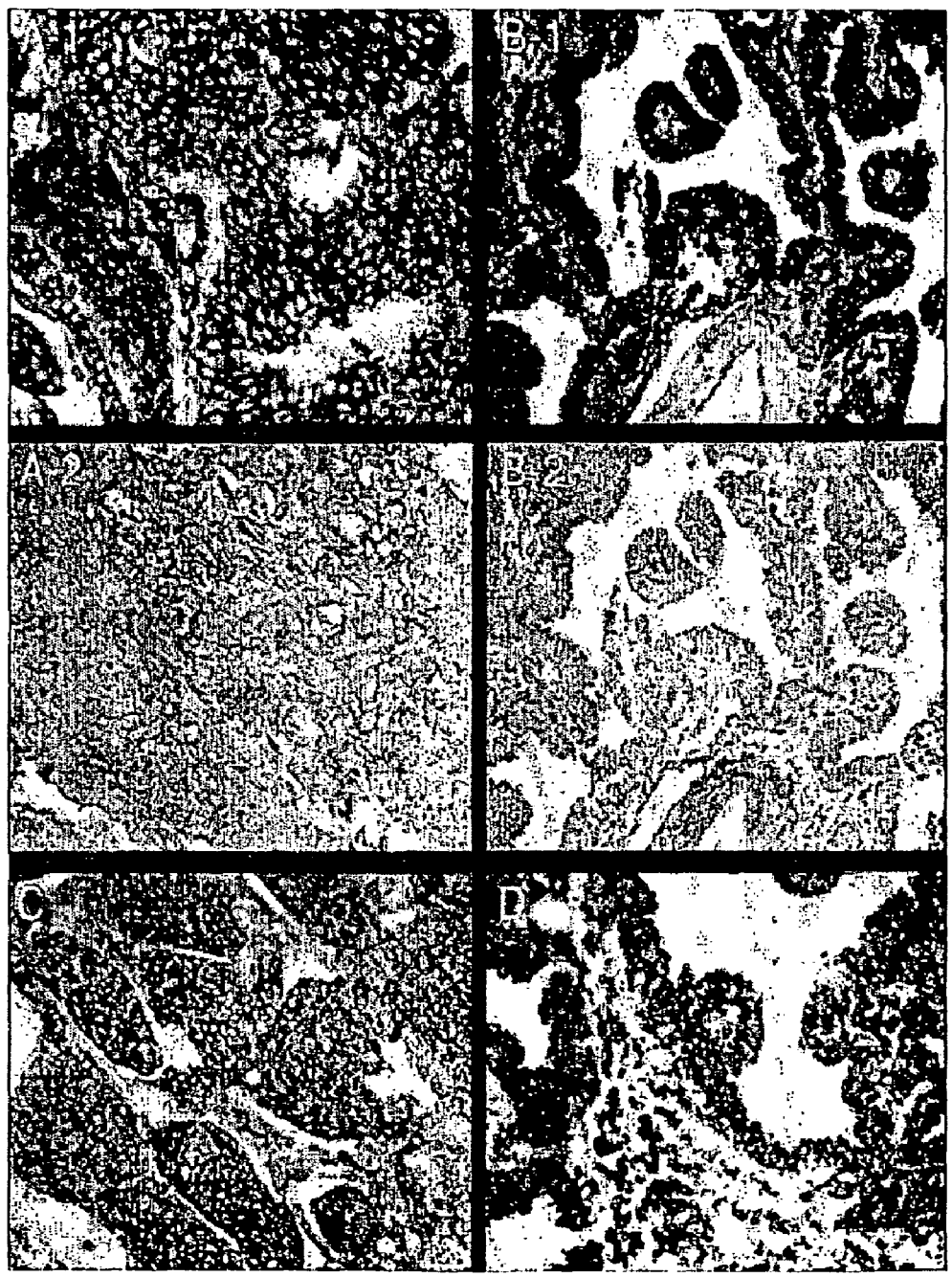

FIG. 9 illustrates expression of AQP gene family in human lung cancer tissues as analyzed by in situ hybridization.

Figure 10:
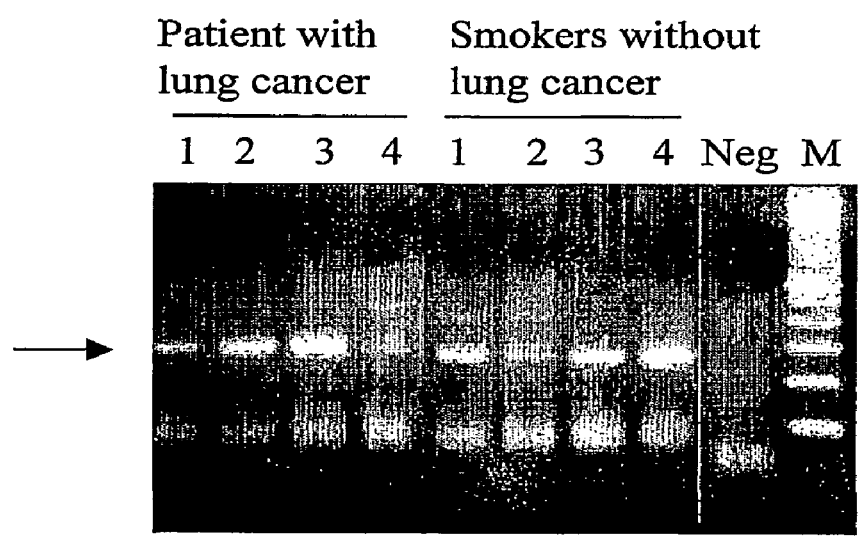

In A-1, antisense probe of AQP1 was used in the analysis of a tissue of squamous cell carcinoma, In A-2, sense probe of AQP1 was used in the analysis of a tissue of squamous cell carcinoma, In B-1, antisense probe of AQP1 was used in the analysis of a tissue of brochioalveolar carcinoma, In B-2, sense probe of AQP1 was used in the analysis of a tissue of bronchioalveolar carcinoma, In C, antisense probe of AQP5 was used in the analysis of a tissue of squamous cell carcinoma, In D, antisense probe of AQP5 was used in the analysis of a tissue of bronchioalveolar carcinoma, FIG. 10 illustrates detection of AQP expression in sputum of patients with lung cancer and normal man as analyzed by using RT-PCR. Products of RT-PCR are shown on gel electrophoresis.

Figure 11:
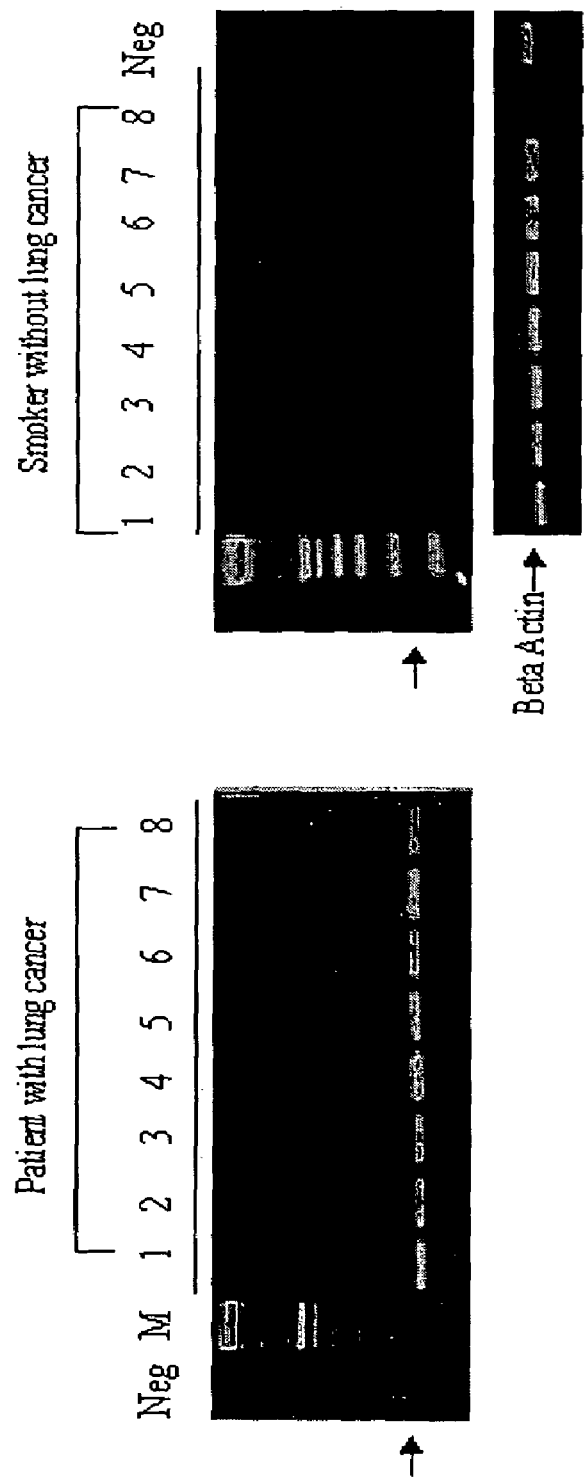

FIG. 11 illustrates detection of AQP expression in blood of patients with lung cancer and normal man as analyzed by using RT-PCR. Products of RT-PCR were identified on gel electrophoresis.

Figure 12:
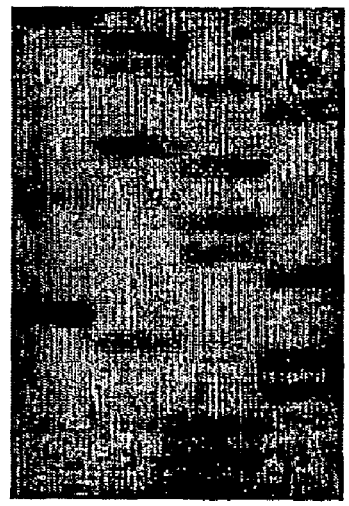
Figure 12:
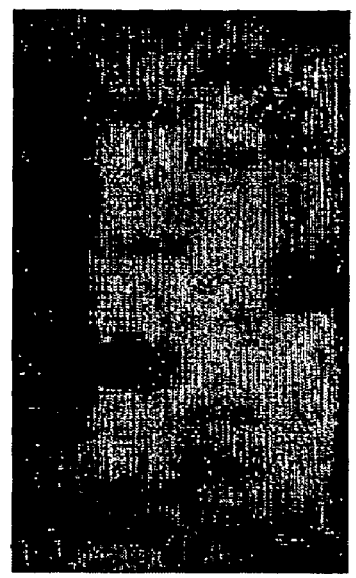

FIG. 12 illustrates the results of nucleic acid sequencing analysis of cDNA of AQP5 which were obtained from normal lung tissues and lung cancer tissues by RT-PCR followed by cloning.

Figure 13:
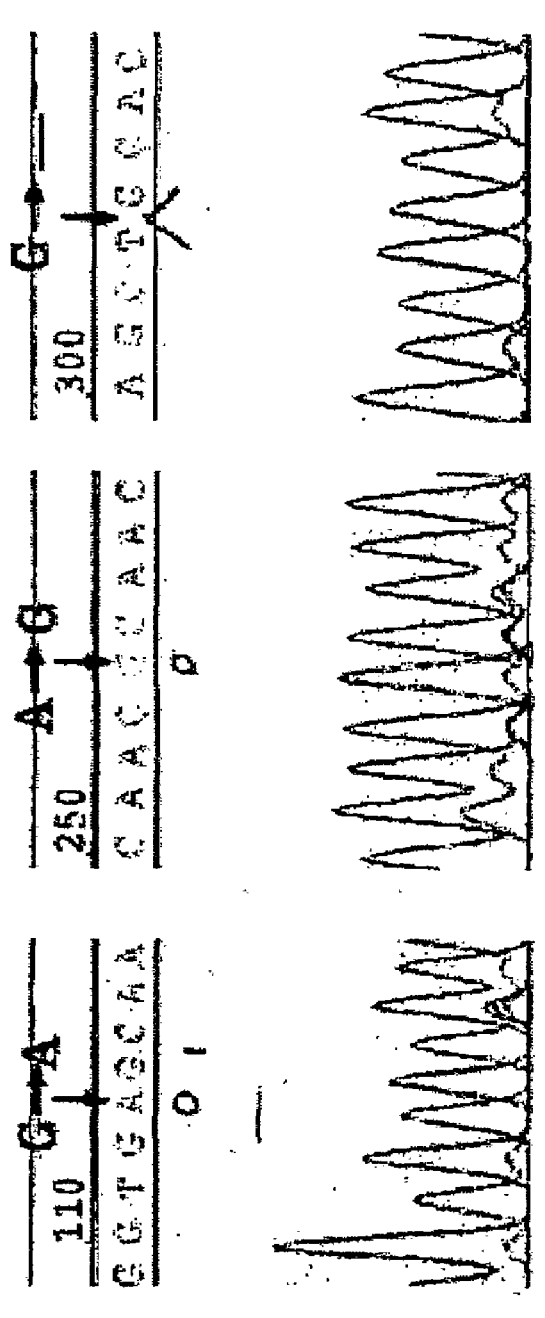

FIG. 13 illustrates the results of automated sequencing analysis of cDNA of mutant AQP5 gene which was obtained from bronchoscopic lavage sample of a patient with lung cancer by using RT-PCR followed by cloning.

Figure 14:
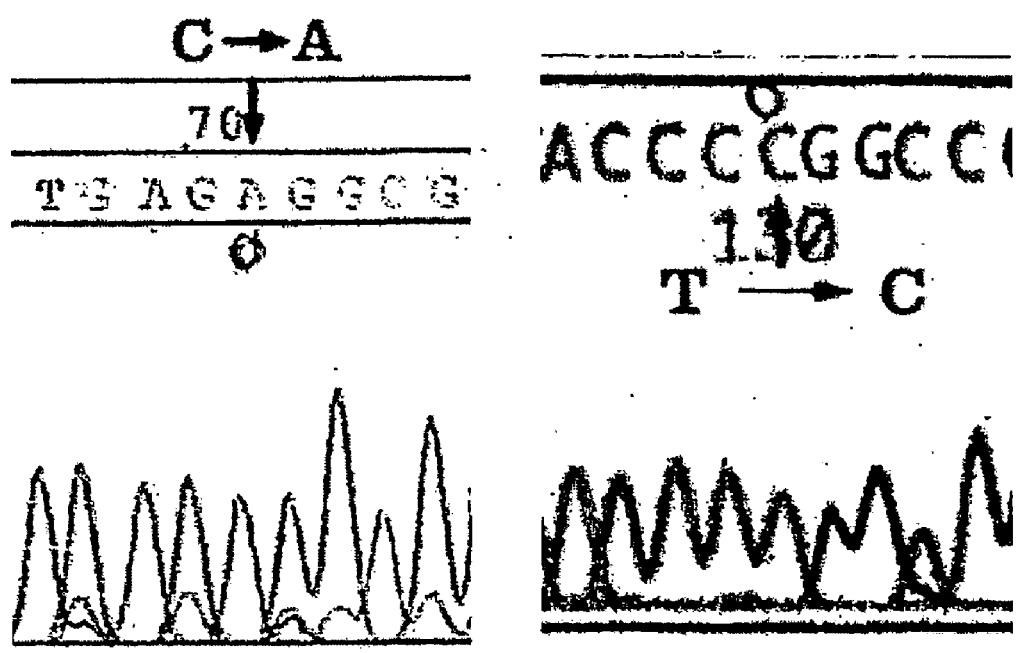

FIG. 14 illustrates the result of automated sequencing analysis of cDNA of mutant AQP5 gene which was obtained by RT-PCR followed by cloning from sputum of a patient with lung cancer.

FIG 15 illustrates the frequency of mutation of AQP5 gene, which was found in human lung cancer tissues.

Figure 15A:
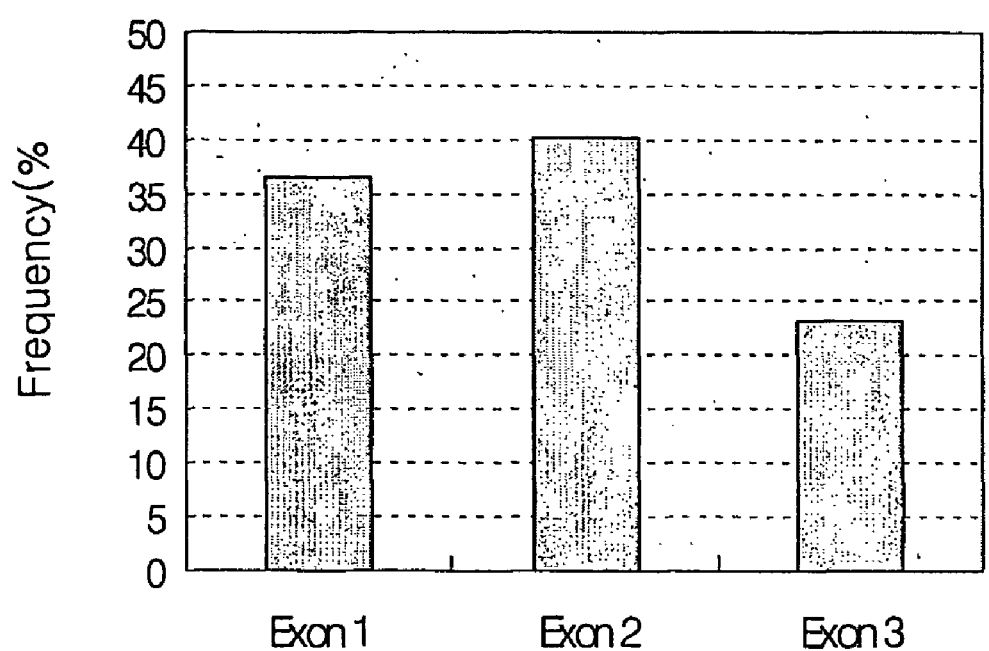

In FIG. 15a, the mutation frequency of AQP5 were analyzed depending on exon number.

Figure 15B:
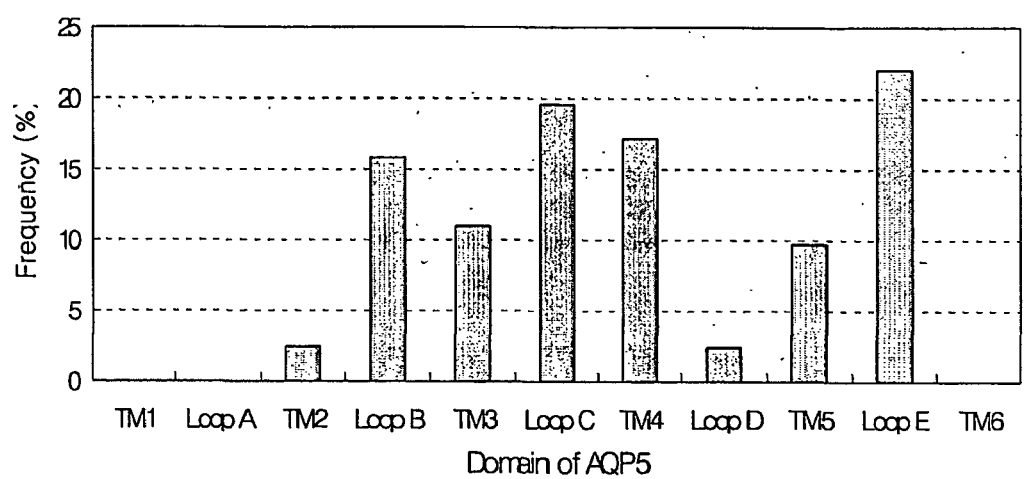
Figure 16:
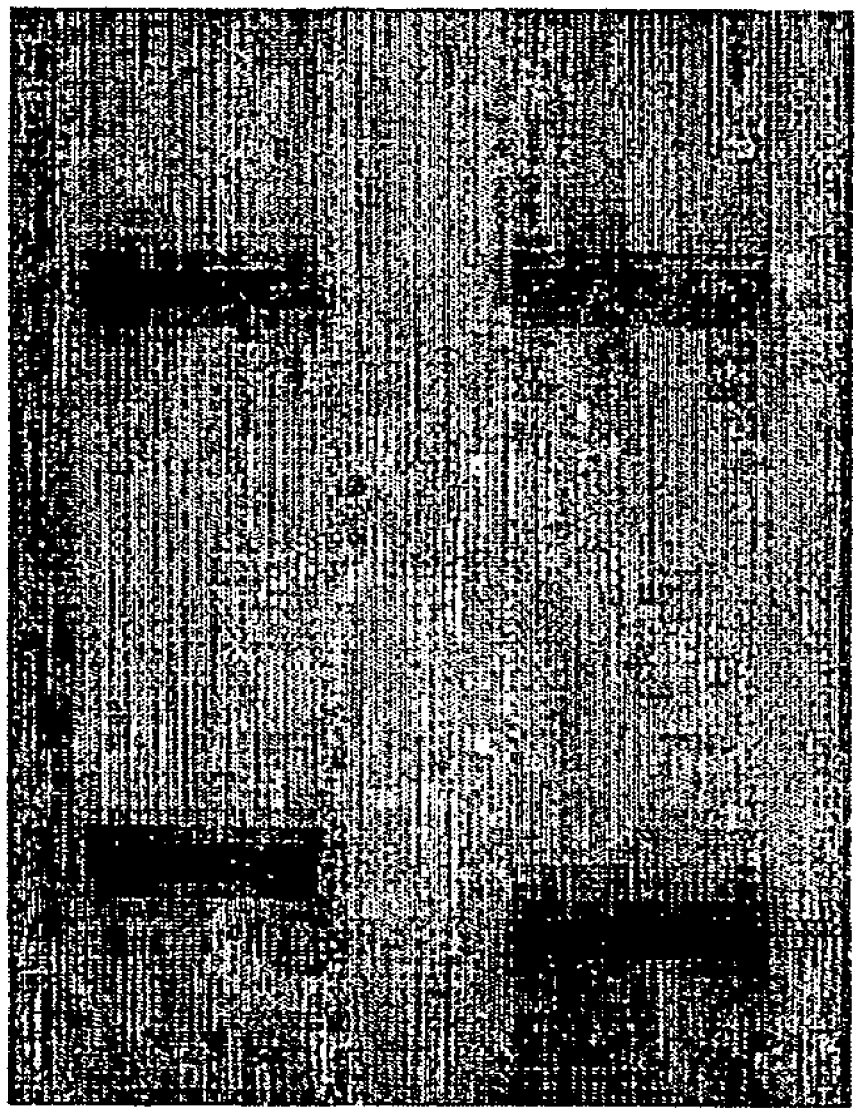

In FIG. 15b, the mutation frequency of AQP5 were analyzed depending on codon number, FIG. 16 illustrates an example of detection of mutation of exon 1 of AQP5 by using single strand conformational polymorphism (SSCP) analysis.

Figure 17:

FIG. 17 illustrates an example of detection of AQP5 mutation by using mutant specific oligonucleotide (MSO) hybridization method.

Figure 18:
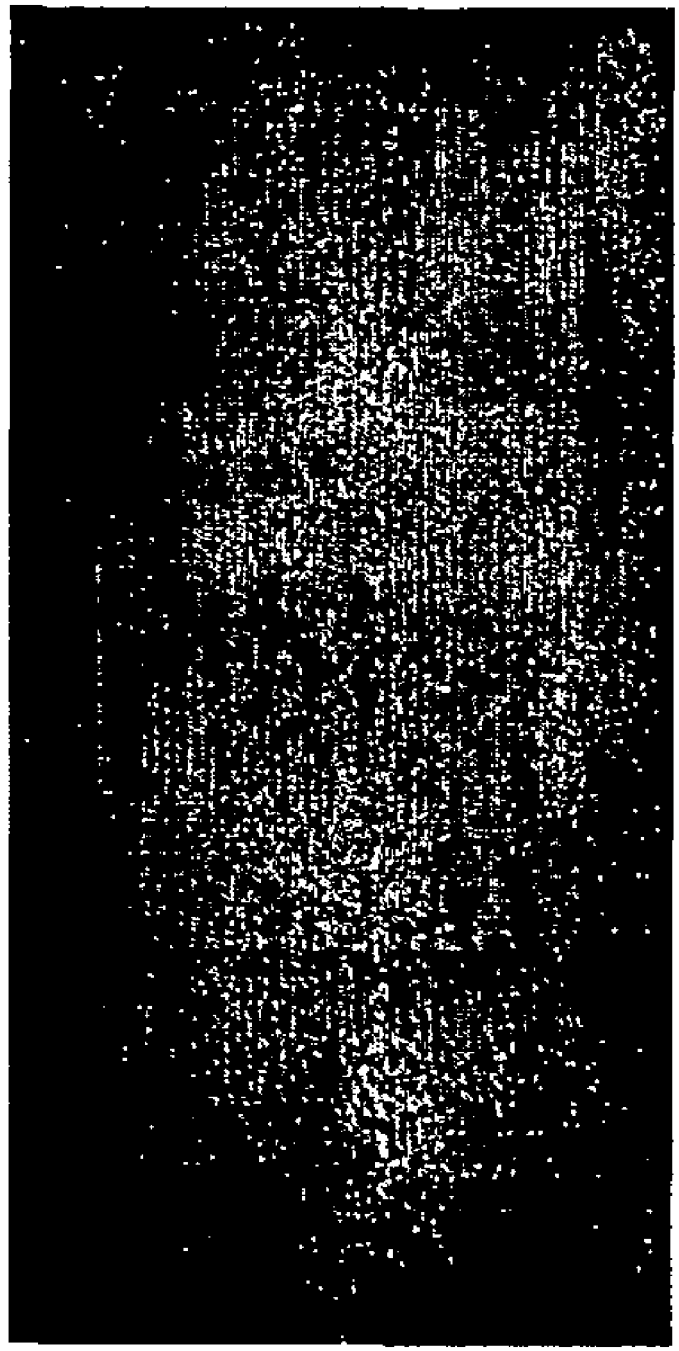

FIG. 18 illustrates an example of detection of mutation of AQP5 by using multiplex PCR. LANE 1: mutant AQP5, LANE 2: wild type AQP5.

Figure 19:
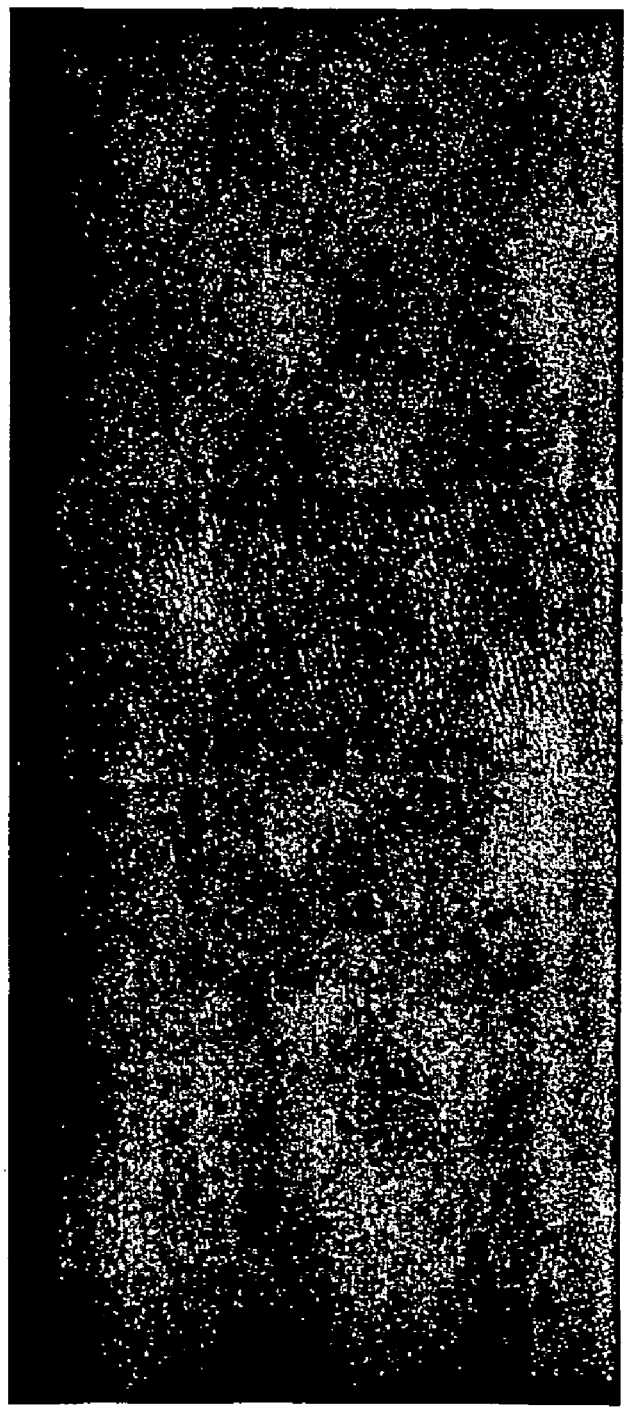

FIG. 19 illustrates an example of analysis of mutation of AQP5 by using DNA chip of the present invention.

FIG. 20 illustrates a list of nucleic acid sequences of sense primer and antisense primer which were arrayed on an oligonucleotide chip of the present invention. The nucleic acid sequences presented in this figure are set forth in SEQ ID NOs:28 to 929, respectively.

Figure 21:

FIG. 21 illustrates a four-colored image of oligonucleotide chip of AQP5 gene in which each base of adenine (A), cytosine (C), guanine (G) and thymine (T) is shown in different color and thus is easily discriminated.

Figure 22:
Figure 22:
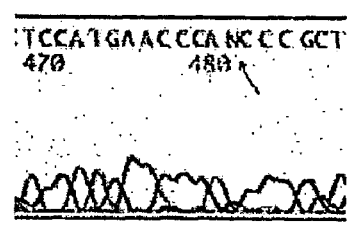

FIG. 22 illustrates an example of test for AQP5 mutation by using oligonucleotide DNA chip and automated nucleic acid sequencing assay.

In FIG. 22a, point mutation of AQP5 was found in the form of heterozygosity of A/G. This point mutation was missed on automated sequencing analysis (ABI Prism) of FIG. 22b.

Figure 23:
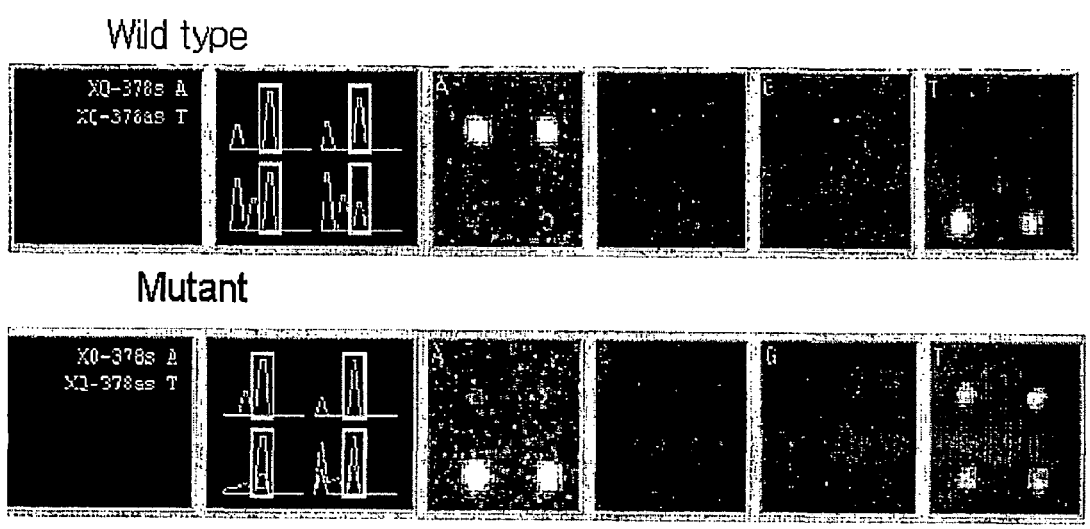

FIG. 23. illustrates an example of test for AQP5 point mutation by using oligonucleotide chip of the present invention. A base was changed to T on analysis of both sense strand and antisense strand.

BEST MODE FOR CARRYING OUT THE INVENTION

In the followings are provided detailed description of the present invention.

First, the inventors investigated expression pattern of aquaporins in bronchial tissues of normal adult humans.

To identify novel molecular markers of cancer inventors have previously focused on genes, proteins or nuclear transcription factors which play important roles in regulation of cell cycle, signal transduction, survival and death. However, we have only found that different genes act in development or proliferation of each cancer (ie. clonal heterogeneity) and could not find any pan-tumor marker, which is common to every human cancer. We herein had turned our focus to cell membrane and cell surface, and through comparative analysis of expression and nucleic acid coding sequences of membrane proteins in both normal tissue and cancer tissue, we have found that AQP gene is a very unique gene which commonly shows change (mutation and/or abnormal expression) in human cancers, in particular lung cancers.

Figure 1:
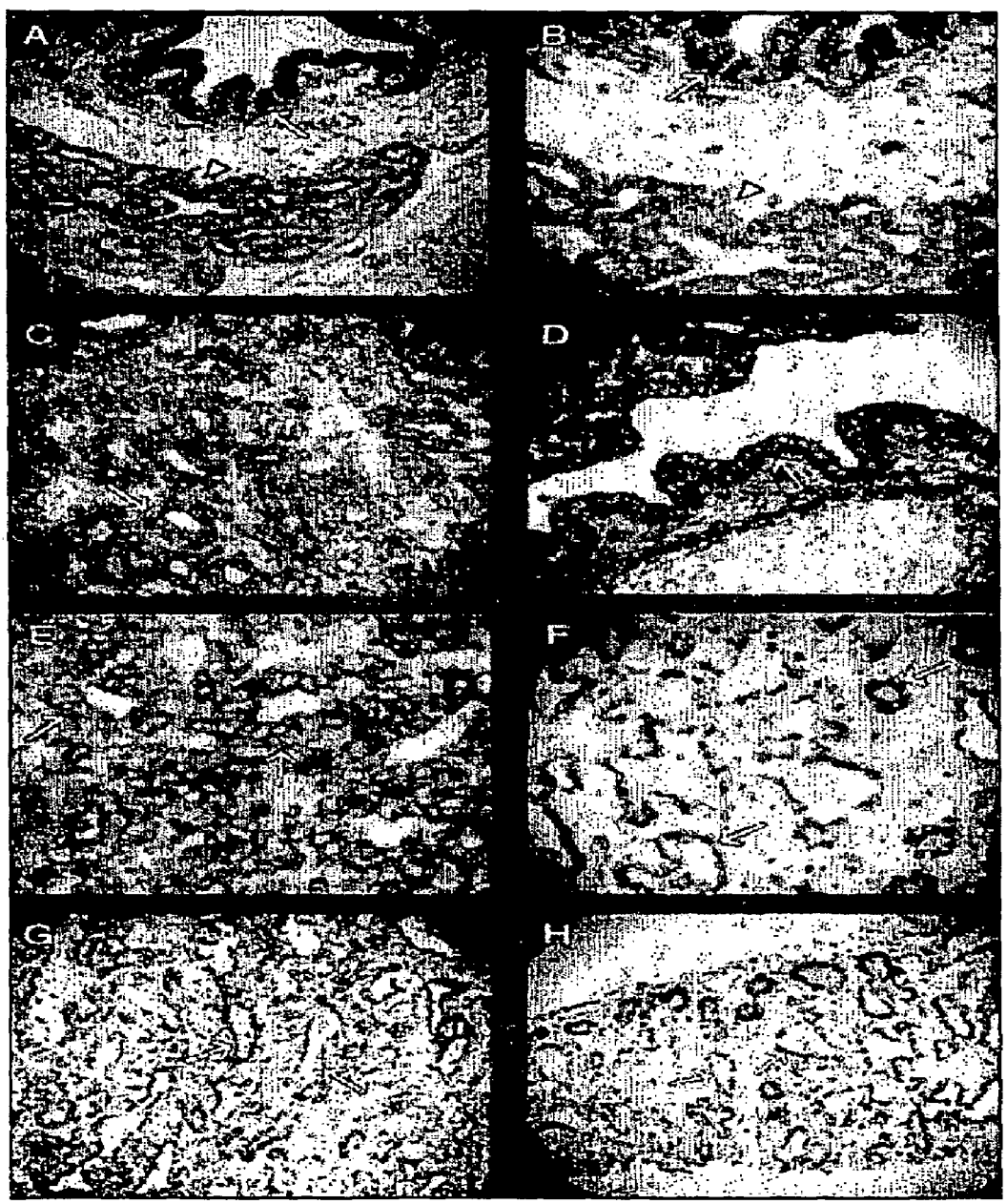
FIG. 1 illustrates expression of aquaporin (AQP) gene in bronchial and airway tissues of adult human by using in situ hybridization methodology.

As the first step of study, we investigated expression pattern of a various type of AQP in normal lung tissues from both adult and infant human by in situ hybridization analysis, because these have not been previously defined. From these studies, we have found that all of AQP 1, AQP3, AQP4 and AQP5 were expressed in bronchial epithelia of both adults and infants and that AQP1 is abundant in pulmonary microvascular endothelial cells and AQP5 in type 1 pneumocytes, respectively (See FIGS. 1 and 2). We also have found by RT-PCR analysis that all of AQP1, AQP3, AQP4 and AQP5 were expressed in bronchial tissues of adults who have never smoked and have no evidence of cancer (FIG. 3). These results indicate that human bronchial epithelia express 4 types of AQP and simultaneous expression of AQP1, AQP3, AQP4 and AQP5 may be a marker of bronchial epithelia. In addition to in situ hybridization and RT-PCR, a variety of methods, including immunohistochemical study western blotting, and DNA microarray analysis can be used to test expression of AQPs.

In the next step of study in the present invention, expression pattern of AQP in human lung cancers was analyzed. First, expression of AQP1, AQP2, AQP3, AQP4, AQP5 and AQP6 in human head and neck carcinoma cell lines and lung cancer cell lines were analyzed by RT-PCR, All of the cell lines were found to express AQP1, AQP3 and AQP5, expression level of AQP5 was highest among all AQPs investigated, AQP4 was expressed by 3 of 4 human lung cancer cell lines, and AQP 2 and AQP6 were not expressed in any of the cell lines investigated (See FIGS. 4, 5, 6 and 7).

The expression and its level of AQP gene family in a variety of human lung cancer cell lines were investigated by northern blotting analysis, which showed that all of the cell lines tested expressed AQP5 in high level (FIG. 8). In addition, expression pattern of AQP gene family in human lung cancer tissues was analyzed by in situ hybridization, the result of which showed that human lung cancer tissues expressed AQP5, AQP1, AQP3 and/or AQP4 (FIG. 9).

In addition, expression profiles of AQP in lung cancer tissue specimens, sample of sputum, bronchoalveolarlavage, pleural fluid and blood of patients with lung cancer were investigated by RT-PCR, the results of which showed that AQP5, AQP3 and AQP1 were clearly expressed in all of the samples investigated (FIG. 10). Messenger RNA (mRNA) of AQP1, AQP3, AQP4 and AQP5 were clearly found in mononuclear cells from blood of lung cancer patients, whereas, only AQP1 was consistently expressed, and AQP3 was rarely expressed, but AQP4 and AQP5 were not expressed in blood mononuclear cells from control people without evidence of lung cancer (FIG. 11). In addition, all of AQP1, AQP3, AQP4 and AQP5 were expressed in cancer cells of stomach, colon and rectum and prostate.

These results indicate: first, human cancer cells including lung cancer simultaneously express AQP1, AQP3, AQP4 and AQP5; second, mRNA of AQP can be easily detected in not only tissue but also in sample of sputum, bronchoalveolar lavage, pleural fluid, blood and other body fluids; third, simultaneous tests for expression of AQP1, AQP3, AQP4 and AQP5 in lung tissue, sample of sputum, bronchial lavage, pleural fluid and blood can be of value to identify the presence of lung cancer.

A variety of methods can be used to investigate expression of AQP in cancer cell lines, lung tissues, sputum, bronchoalveolar lavage sample, pleural fluid, blood and other body fluids, which include RT-PCR, RT-PCR-Southern blotting or oligonucleotide hybridization, in situ hybridization, nothern blotting, immunohistochemical study, western blotting, DNA microarray, etc.

The expression of AQP gene in human lung cancer tissues were investigated by northern blotting analysis and in situ hybridization, which showed that human lung cancer tissues expressed AQP1, AQP3, and AQP5 and especially, expressed AQP5 in high level (See FIGS. 8 and 9).

The object of the next study of the present invention was to identify the mutation of AQP in human lung cancer. The inventors performed PCR amplification of coding sequence of genomic DNA of AQP1, AQP3, AQP4 and AQP5 from lung cancer tissues and peripheral blood lymphocytes of control population with no evidence of lung cancer, followed by cloning and nucleic acid sequencing analysis of PCR products. The sequences of cloned PCR products were comparatively analyzed with that of wild type AQP1 (Genebank No. NM-000385), wild type AQP3 (Genebank No. NM-004925), wild type AQP4 (Genebank No. U63623) and wild type AQP5 (Genebank No. NM-001651). The results of this comparative study showed that most of the lung cancers tested carried mutation of AQP5 gene in widely variable pattern and that none of the control population carried mutation of AQP5 gene. To further confirm these results, functioning domains of AQP5 cDNA, which include most of exon 1, the whole exon 2 and most of exon 3 (from the one hundred forty third base to five hundred ninety third base), were amplified by RT-PCR, and their nucleic acid sequences were analyzed. The results of this study again showed that most of lung cancer tissues tested and none of the lung tissues from normal control population carried mutation of AQP5 (See FIGS. 12, 13 and 14). Mutational pattern of AQP in human cancers, in particular lung cancer, were variable, but we could identify major hot spots of AQP5 mutation, which are listed in Table 5a and 5b.

Remarkably, almost all human lung cancers tested were found to carry mutant AQP5 gene and these AQP5 mutation were concentrated in central 4 domains, including loop B, loop C, loop E and the fourth domain (TM4), all of which play key role in water channel function (See FIG. 15). Therefore, mutation of AQP5, is a promising genetic tumor marker to detect lung cancer. In addition, the other human cancers, including prostate cancer, colorectal cancer, and stomach cancer also commonly carry mutation of AQP5, and therefore, mutation of AQP5 can be regarded as a pan-tumor marker.

The inventors also tested mutation of AQP5 in samples of bronchial lavage, sputum and malignant pleural fluid from patients with lung cancer and found AQP5 mutation in 100% frequency from bronchoscopic ravage, in 96.7% frequency from sputum and in 100% frequency from malignant pleural fluid, respectively.

In addition to nucleic acid sequencing analysis, a variety of methods can be used to detect mutation of AQP5, which include SSCP (Single strand conformational polymorphism) analysis (See FIG. 16), MSO (Mutant specific oligonucleotide) hybridization analysis (See FIG. 17), ARMS (amplification refractory mutation system) analysis (See FIG. 18 and EXAMPLE 7) and other known methods.

DNA chip or DNA microarray is a biochip onto which several hundreds to several hundred thousands of DNA fragments are arrayed by using robotic and computer technology. For example, DNA chip is a microarray chip onto which a number of DNA fragments are arrayed in extremely high density and is used for a wide variety of genetic study. The DNA chip can replace a number of existing methods for genetic study, including Southern blotting, nothern blotting, DNA sequencing analysis and a variety of mutation analysis methods. The major difference of DNA chip from methods of classical genetic study are that matrix for arraying genetic materials in DNA chips are sold materials such as glass, but matrix in classical methods are usually nitrocellulose or nylon membrane and that DNA chip makes it possible to analyze many genes simultaneously in a short time (Case-Green S C et al. Analyzing genetic information with DNA arrays, Current Opinions in Chemical Biology (1998) 2, 404-410; Lemieux B et al. Overview of DNA chip technology, Molecular Breeding(1998), 4, 277-289).

DNA chip is classified into complementary DNA (cDNA) chip and oligonucleotide chip (oligochip) depending on the type and size of genetic materials to be arrayed on the chip. cDNA chip is arrayed by a number of cDNA fragments which are whole or part of open reading frame (with more than 500 bases in length) or EST. Oligonucleotide chip is arrayed by oligonucleotides with 15 to 25 bases in length. Oligonucleotide chip is highly useful for detection of mutation or polymorphism, and cDNA chip for analysis of gene expression, respectively. One of the main objects of the present invention was to make oligonucleotide chip which can detect mutation of AQP5, accurately and efficiently from large number of clinical samples. The inventors have designed and produced hybridization type oligonucleotide chip on the basis of mutation profile information of AQP5 in lung cancer which were obtained from nucleic acid sequencing analysis as in EXAMPLE 4. These oligonucleotide chips are based on oligonucleotide probe hybridization principles and can accurately detect mutation of AQP5.

With oligonucleotide DNA chips produced as in the above, mutation of AQP5. was analyzed in tissues of lung cancer and normal lung tissues, and in samples of bronchoscopic lavage and sputum from patients with lung cancer and control people without evidence of lung cancer. By using the oligonucleotide chip analysis, mutation of AQP5 cDNA was found in all of the samples from lung cancer patients but no mutation was found in any of the samples from normal control group. This result strongly suggest that the above oligonucleotide chip is useful to test for mutation of AQP5 (See FIG. 19).

The other method invented by us to detect mutation of AQP5 is a novel oligonucleotide chip which interprets nucleic acid sequence by using arrayed primer extension (APEX) reaction. This sequencing type oligochip combines both microarray technology and Sanger's dideoxy sequencing analysis technology and thus are called minisequencing chip (Kurg A. et al. Arrayed primer extension: solid-phase four-color DNA resequencing and mutation detection technology. Genet Test (2000) 4, 1-7; Tonisson N et al. Arrayed primer extension on the DNA chip: Method and application. In Schena M ed. Microarray biochip technology. Eaton Publishing:Natick,2000; 247-264). The basic technology of analysis of AQP5 mutation by using this minisequencing type oligonucleotide chip are as follows:

First, oligonucleotide chips were designed and produced. The appropriate oligonucleotide primers were designed for each base of sequence of AQP5 cDNA, modified by attaching chemical linker to their 5' ends, and were arrayed (ie spotted or printed) by using microarrayer machine onto microscopic glass slides, which had been treated by special coating solutions.

Second, target DNAs were prepared. Genomic DNA or cDNA are isolated from clinical samples of cancer or control population, coding sequence of AQP5 are amplified by PCR, and then PCR products are changed into fragments of nucleotides with 50 to 100 base pairs in length.

Third, APEX reaction was performed on the oligonucleotide chips. Fragmented PCR products, each of four dideoxynucleotides(ddATP, ddCTP, ddGTP, ddTTP) which were labeled by different fluorescence and DNA polymerase were placed onto oligonucleotide chips; and then APEX reaction, a variant of Sanger's sequencing reaction, was carried out.

Fourth, oligonucleotide chips were analyzed after APEX reaction by using 4 color fluorescence DNA scanner and the sequence of each base of coding sequence of AQP5 gene from the target samples were interpreted. All the coding sequence of AQP5 can be analyzed automatically and quickly by using software of the scanner, and the equivocal results were corrected.

The results of AQP5 cDNA mutation analysis by conventional automated nucleic acid sequencing method (ABI PRISM) were comparatively analyzed with those by the above minisequencing type oligonucleotide chip. The results of AQP5 cDNA mutation test by using oligonucleotide chip concurred with those by conventional automated sequencing method in 98 percent of sample tested. In the remaining 2 percent of samples, oligonucleotide chip detected additional point mutation of AQP5 which were missed by automated sequencing analysis (See FIGS. 21, 22, and 23).

The inventors recommend test for expression of AQP1, AQP3, AQP4 and AQP5 as the first step to detect or screen cancer. The next step necessary to confirm the presence of cancer is to test for mutation of AQP5. To test for AQP5 mutation, cDNA of AQP5 are PCR-amplified from target DNA or cDNA isolated from clinical samples, PCR products are initially screened by MSO hybridization or ARMS and finally analyzed by oligonucleotide chip and/or automated nucleic acid sequencing method. We recommend oligonucleotide chip in the present invention as the best single tool to test for mutation of AQP5. The methods described in the present invention, in particular oligonucleotide chip, can detect mutation of AQP5 from a wide variety of clinical samples, including tissue or cellular specimen, blood, sputum, stool, urine, sputum, cerebrospinal fluid, pleural fluid, peritoneal fluid and lavage samples obtained by endoscopy.

The methods described in the present invention can be applied to test for extent of cancer in clinical practice as follows: Cells or tissue specimens are taken under the guidance of computerized tomography scan or endoscopy from the body areas where tumor extension is suspected, and blood and pleural fluid are also-taken from patients with cancer. RNA are isolated from tissues, cells, blood or pleural fluid, RT-PCR analysis are carried out to identify cells which express all of AQP5, AQP3, AQP4 and AQP1, which is followed by test for AQP5 mutation by using oligonucleotide chip, etc. These molecular study make it possible to identify therapeutic response, residual or recurrent cancer after therapy for cancer, including surgery, radiation therapy and chemotherapy.

The above genetic tests for AQP are also of value to identify the efficacy of chemoprevention of cancer. Chemoprevention is indicated when cancer or precancerous lesion of the lung are highly suspected by finding AQP5 mutation in sputum or bronchoalveolar lavage, but no cancer is found on clinical study. The AQP5 mutation tests in the present invention can be ideally applied to sputum or bronchoalveolar lavage to identify the outcome of chemoprevention for lung cancer.

In the following examples, the present invention is described in more detail. However, these are only some of examples and the present invention is not limited to these examples:

EXAMPLE 1

Analysis of AQP Gene Expression in Normal Lung Tissues by Using in situ Hybridization and RT-PCR Method Bronchial tissue specimen were taken by bronchoscopic brush biopsy from adult human without evidence of lung cancer (some with smoking history) and 17-week old male infant, and were treated, by RNAsol (TEL-TEST, USA), followed by homogenization. Wherein, bronchial tissue from adult human with smoking history was obtained from bronchial brush biopsy.

The mixture was treated by chloroform, 0.2 ml, shaked, placed in 4° C. water bath for 15 minute, followed by centrifuge in 4° C. at 15,000 rpm. Two thirds of supernatant after centrifuge was taken to new tube, added by same volume of 2-propanol and were placed in 4° C. water bath for 15 minute. The pellet of RNA was obtained after precipitation using centrifugation in 4° C. at 15,000 rpm, washed by 80% ethanol containing diethyl pyrocarbonate (DEPC), dried at room temperature, treated by 50 μl DEPC-deionized water and then purified total RNA was obtained. The concentration of RNA was measured by spectrophotometer.

Complementary DNA (cDNA) was synthesized from the total RNA by reverse transcription (RT) reaction. Total RNA was mixed with DEPC-deionized water in 1:10 ratio, placed for 10 minutes in 70° C. water bath, mixed with 10×RT-buffer (500 mM Tris (pH 8.3), 60 mM $MgCl_2$, 400 mM KCl), 0.1 M DTT (Dithiothreitol), 25 mM dNTP, oligo(dT) primer 2μl, and RNAsin (Promega, USA) 1 μl. The reaction mixture was incubated for 10 minutes at 37° C., and was added by 100 nits of Superscript II reverse transcriptase (GIBCO BRL, USA), incubated for 1 hour 37° C., and then cDNA was obtained, which was used as the template of the following PCR reaction.

Sense and antisense oligonecleotide primer were designed and synthesized for each type of AQP as in Table 3. cDNA of each type of AQP was produced by RT, and was amplified by PCR reactions as in the condition listed in Table 4.

TABLE 3

Sequence of oligonucleotides which were used as the primer for PCR of each type of aquaporin.

| Target gene of PCR | Sense primer sequence | Antisense primer sequence |
|---|---|---|
| AQP1 | SEQ ID NO: 2 | SEQ ID NO: 3 |
| AQP3 | SEQ ID NO: 4 | SEQ ID NO: 5 |
| AQP4 | SEQ ID NO: 6 | SEQ ID NO: 7 |
| AQP5 | SEQ ID NO: 8 | SEQ ID NO: 9 |
| Beta-actin (control) | SEQ ID NO: 10 | SEQ ID NO: 11 |

TABLE 4

PCR condition of cDNA of AQP genes

| Composition of PCR reaction | Reaction condition |
|---|---|
| 10× Taq buffer<br>100 mM Tris-Cl<br>500 mM KCl<br>15 mM MgCl<br>0.01% gelatin<br>Taq polymerase<br>(5 units/μl)<br>dNTP 500 uM<br>sense primer (20 pmole)<br>antisense primer (20 pmole) | 1. Denaturation for 4 minutes at 95° C.<br>2. Repeat 40 cycles for AQP as follows:<br>(beta actin: 25-cycles)<br>10 seconds at 94° C.<br>50 seconds at 63° C.<br>50 seconds at 72° C.<br>3. Final extension for 10 minutes at 72° C. |

PCR products were visualized on 0.9% agarose gel electrophoresis. PCR product of AQP1 was shown as a band with size of 230-bp, AQP3 130-bp, AQP4 220-bp, AQP5 430-bp, and beta-actin 340-bp, respectively.

Human cDNA of AQP1, AQP3, AQP4 and AQP5 obtained in the way above were introduced into the plasmid pCRII-TOPO (Invitrogen, USA) and this construct was used as a template to generate sense and antisense probes during in vitro transcription reaction. During the transcription, non-radioactive labelling of the single strand RNA probe was performed using digoxygenin-UTP (DIG RNA labeling kit, Boehringer Mannheim, USA). DIG-labelled RNA probe was mixed with RNAase inhibitor, stored at −80° C. and used for in situ hybridization as follows.

Paraffin-embedded tissue section with 4 μm thickness were cut onto silane-coated slides (Signia Chemical, USA). The sections were deparaffinized in xylene, rehydrated in gradually decreasing concentrations of ethanol from 90% to 50%, and treated with 0.2 N HCl. The sections were then treated with protein kinase K for 15 min at 37° C., washed 3 times with 1×PBS, post-fixed in 4% paraformaldehyde for 5 min at room temperature, and re-rinsed with 1×PBS. Then they were acetylated in 0.25% acetic anhydride, 0.1M triethanolamine for 10 min. They were dehydrated in gradually increasing concentration of ethanol and air-dried prior to hybridization. They were prehybridized for 1 hour at 42° C. in hybridization buffer which consist of 20×SSC (3M NaCl, 0.3M sodium citrate, pH 7.0), 50% deionized formamide, 2.5 mg prenatured salmon sperm DNA, 1 g dextran sulfate, 2% 100× Denhart solution (20 g/l Ficoll, 20 g/l polyvinylpyrolidone, 20 g/l bovine serum albumin), 2% DTT and 4 mg of yeast tRNA. Hybridization was performed at 42° C. in the hybridization buffer containing 400 ng of probe of AQP1, AQP3, AQP4 and AQP5. The sections were then washed 2×SCC, and were treated with RNase solution (500 mM NaCl, 10 mM Tris-HCl (pH 7.5), 1 mM EDTA (pH 8.0), 20 μg/ml RNase A) for 30 min at 37° C. Then the sections were rinsed in buffer 1 (0.1M maleic acid, 0.15M NaCl) for 5 min at room temperature, and then incubated with buffer 2 (2% normal sheep serum, 0.3% Triton X-100) for 30 min also at room temperature. Slides were then incubated for 12 hours at 4° C. with an anti-digoxigenin antibody (in 1:500 dilution). After two rinses in buffer 1, slides were rinsed shortly in buffer 3 (100 mM Tris-HCl, 100 mM NaCl, 50 mM MgCl, pH 9.5). Color reaction was induced by treatment with 5-bromo-4-chloro-3-indoyl phosphate and nitro-blue tetrazolium chloride and then slides were rinsed in buffer 4 (10 mM Tris-HCl, 1 mM EDTA), mounted, were observed under microscopy and alkaline phosphatase present within sections was detected. Sections incubated with digoxygenin-labelled sense probe in the same condition were used as negative controls.

The results of in situ hybridization showed that all of AQP1, AQP3, AQP4 and AQP5 were expressed by bronchial epithelium of normal adults with or without history of smoking as well as normal infant. (See FIGS. 1, 2 and 3).

EXAMPLE 2

Analysis of AQP Gene Expression in Human Lung and Head and Neck Carcinoma Cell Lines.

Expression of each type of human AQP gene in human lung carcinoma cell lines and head a neck carcinoma cell lines were analyzed by RT-PCR, Nothern blotting and in situ hybridization assay. Human lung cancer cell lines, including H460, H1944, H596 and A549, and head and neck carcinoma cell lines, including 183A, 22B, 17A, 11B were purchased from ATCC company (USA) and these cell lines were examined for AQP expression by using RT-PCR. The methods of RT-PCR were as same as in EXAMPLE 1, except the sequences of oligonucleotide primer for PCR of cDNA of AQP5. The sequence of sense primer for AQP5 was as same as SEQ ID NO: 12 and antisense primer SEQ ID NO: 13, respectively. On electrophoresis, the PCR product of AQP1 was shown as a band with size of 230-bp, 247-bp for AQP5, and 340-bp for beta-actin, respectively. PCR products of AQP were introduced into TA cloning vector and sequenced to confirm each AQP specific sequences. On the RT-PCR assay, all of the cell lines studied were found to express AQP5, AQP1 and AQP3, and the expression level of AQP5 was highest of all types of AQP. AQP4 was expressed in 3 of 4 lung cancer cell line, including H460, H1944 and A596, and only 11B cell line out of 4 head neck cell lines (See FIGS. 4, 5, 6 and 7). AQP2 and AQP6 were not expressed in any of the cell lines tested.

Next, AQP gene expression was analyzed by Nothern blotting in cancer cell lines established from a variety of type of human lung cancer. The target cell lines included squamous carcinoma cell lines (SC1 and SC2); adenocarcinoma cell lines (ADE-1, ADE-2 and ADE-3), bronchoalveolar carcinoma cell lines (BAC), large cell carcinoma cell line (LAC) and small cell carcinoma cell line (SMC). All of these cell lines were purchased from ATCC (USA). The conventional method was used for northern blotting assay (Sambrook J et al. Molecular cloning, second edition, Cold Spring Harbor Laboratory Press (1989)). RNA was extracted from cell lines in the same method as in EXAMPLE 1 except that RNAsol B (Genomed, Germany) was used instead of RNAsol. Twenty μg of total RNA were heated for 1 min, mixed with agarose gel buffer for RNA which consist of agarose 1.2 g, 10 ml of 10×MOPS(3-[N-morpholino]propanesulfonic acid) buffer (41.8 g/l MOPS, 3M sodium acetate 16.6 ml, 20 ml of 0.5M EDTA, pH 8.0) and 18 ml of 37% formaldehyde, 100 ml of DEPC-treated deionized water and the mixture were loaded into electrophoresis. After electrophoresis, RNA was transferred into nylon membrane by using conventional capillary method (Sambrook J et als. Molecular cloning, second edition, Cold Spring Harbor Laboratory Press (1989)) and fixed with UV-crosslinker (1200 J/cm$^2$). The same probe as in EXAMPLE 1 was used as the AQP cDNA probe and GADPH cDNA probe was prepared in the same way as in EXAMPLE 1. The cDNA probes for AQP and GADPH were labeled by [α-32P] using the conventional methods (Sambrook J et al. Molecular cloning, second edition, Cold Spring Harbor Laboratory Press (1989)). Hybridization reaction was performed between the nylon membrane transferred by RNA of lung cancer cell lines and radio labelled probe of AQP and GADPH. After hybridization, membrane was washed with washing solutions 1 (50 ml 20×SSC, 5 ml 10% SDS, total volume 500 ml) twice or thrice for 10 min at 42° C., then washed again with washing solution 2 (2.5 ml 20×SSC, 5 ml 10% SDS, DEPC-treated deionized water, total volume 500 ml) twice at room temperature. Then membrane was exposed to X-ray film (Kodak, USA), the signals were observed and their density were analyzed by image analyzer.

The results of northern blotting showed that all of the lung cancer cell lines expressed AQP1, AQP4 and AQP5 regardless of the cell type of each cell line and AQP5 was expressed in highest level (see FIG. 8).

In addition, inventors investigated expression of AQP in tissues of a variety of type of human lung cancer by using in situ hybridization to identify the type of cells which express AQP and their level of expression of AQP. The same as in EXAMPLE 1 was used for in situ hybridization.

The results of this study showed that many types of human lung cancer, including squamous cell carcinoma, bronchioalveolar carcinoma and adenocarcinoma, expressed highly AQP5, AQP1 and AQP3 and that in particular, human lung cancer cells expressed AQP5 in high level regardless of type of carcinoma (See FIG. 9).

EXAMPLE 3

Analysis of AQP Gene Expression from Lung Tissue, Bronchial Lavage, Sputum, Blood and Pleural Fluid in Lung Cancer and Normal Control by RT-PCR Lung cancer tissues, normal bronchial tissues, samples of bronchoscopic lavage, sputum, peripheral venous blood and pleural fluid were obtained from patients with lung cancer and benign controls who underwent bronchoscopy but did not show evidence of lung cancer. In particular, blood samples were taken from patients with stage 3 or stage 4 lung cancer and pleural fluid from patients with lung cancer accompanied by malignant pleural effusion. RNA and DNA were extracted using the same method as in EXAMPLE 1 and cDNA of AQP were amplified by PCR using the same method as in EXAMPLE 1, except that PCR of AQP5 cDNA was performed by the method as in EXAMPLE 2. The PCR products were visualized in 0.9% agarose gel, in which PCR product of AQP1 cDNA was visualized as band with size of 230-bp, AQP3 130-bp, AQP4 220-bp, AQP5 247bp, and beta-actin 340-bp, respectively. In addition, dot blotting and Southern blotting were carried out using probes specific to each type of AQP and beta-actin in the conventional way (Sambrook J et al. Molecular cloning, second edition, Cold Spring Harbor Laboratory Press (1989)).

On the above study, mRNA of AQP1, AQP3 and AQP5 were found to present in high level in lung cancer tissues, and samples of sputum, bronchial lavage and pleural fluid from patients with lung cancer (See FIG. 10).

With respect to test of blood sample, all of AQP 1, AQP3, AQP4 and AQP5 were found to be expressed in mononuclear cells from patients with lung cancer, whereas, in normal controls, only AQP1 was consistently expressed, AQP4 and AQP5 were not expressed at all and rarely AQP3 was expressed, which may be due to contamination of erythrocytes (See FIG. 11).

These results indicate that expression of AQP5, AQP1 and AQP3 is detectable not only in lung cancer tissues but also in samples of sputum, blood, bronchial lavage and pleural fluid from patients with lung cancer. Of course, we can also detect information on nucleic acid sequence of AQP from this study.

EXAMPLE 4

Analysis of Nucleic Acid Sequences of AQP5 Gene in Lung Cancer Tissues and Samples of Bronchoscopic Lavage, Sputum and Blood.

Total RNA and cDNA were isolated from tumor tissues of 20 patients with lung cancer, and then most of exon 1, the whole exon 2 and most of exon 3 of cDNA of AQP1, AQP3, AQP4 and AQP5 were amplified by PCR followed by cloning by using the same methods as in the previous EXAMPLE 1. In addition, cloned cDNA of AQP were analyzed by automated sequencing method (ABI PRISM), followed by study of presence and location of mutation by using Blast Search Program.

In addition, lung cancer tissues were obtained from 112 patients with lung cancer and normal bronchial tissues from 105 control populations, respectively, RNA and cDNA were obtained from the tissues and cDNA of AQP5 was amplified by PCR by the same method as in previous EXAMPLE 2. The sequences of four hundred fifty-bp PCR product, which amplified central portion of AQP5 cDNA from the one hundred forty third base to five hundred ninety third base which include most of exon 1, the whole exon 2 and most of exon 3, were analyzed directly by nucleic acid sequencing or initially cloned in pGEM T-easy vector (Promega, USA), followed by nucleic acid sequencing analysis. The sequences of each amplified product of AQP5 were compared to normal cDNA sequence of human AQP5 gene (SEQ ID NO: 1), and then the presence or absence and location of mutation of AQP5 were investigated.

A variety of mutations of AQP5 were found in all of the cDNA samples from lung cancer tissues, whereas, mutation of AQP was rarely found in cDNA samples from normal lung tissues. Mutational hot spots of AQP5 are summarized in Table 5a and 5b (See FIGS. 12 and 15).

TABLE 5a

Mutational pattern of cDNA of AQP5 Gene: Summary of sixty mutational hot spots

| No. Hot spots | Exon No | Region | Codon No | Base No. | Mutation frequency (%) |
|---|---|---|---|---|---|
| 1 | 1 | TM2 | 54 | 162 | 1.8 |
| 2 | 1 | TM2 | 55 | 164 | 1.8 |
| 3 | 1 | Loop B | 64 | 192 | 7.1 |
| 4 | 1 | Loop B | 66 | 197 | 2.7 |
| 5 | 1 | Loop B | 69 | 205 | 2.7 |
| 6 | 1 | Loop B | 74 | 221 | 3.6 |
| 7 | 1 | Loop B | 78 | 233 | 2.7 |
| 8 | 1 | Loop B | 79 | 235 | 14.3 |
| 9 | 1 | Loop B | 80 | 238 | 2.7 |
| 10 | 1 | Loop B | 83 | 247 | 2.7 |
| 11 | 1 | Loop B | 84 | 251 | 3.6 |
| 12 | 1 | TM3 | 91 | 273 | 7.1 |
| 13 | 1 | TM3 | 95 | 283 | 2.7 |
| 14 | 1 | TM3 | 96 | 288 | 2.7 |
| 15 | 1 | TM3 | 97 | 290 | 7.1 |
| 16 | 1 | TM3 | 101 | 303 | 7.1 |
| 17 | 1 | TM3 | 103 | 307 | 7.1 |
| 18 | 1 | TM3 | 109 | 327 | 3.6 |
| 19 | 1 | Loop C | 111 | 331 | 7.1 |
| 20 | 1 | Loop C | 112 | 334 | 2.7 |
| 21 | 1 | Loop C | 112 | 335 | 1.8 |
| 22 | 1 | Loop C | 119 | 357 | 3.6 |
| 23 | 1 | Loop C | 121 | 363 | 2.7 |
| 24 | 2 | Loop C | 122 | 365 | 2.7 |
| 25 | 2 | Loop C | 123 | 367 | 1.8 |
| 26 | 2 | Loop C | 124 | 371 | 3.6 |
| 27 | 2 | Loop C | 126 | 376 | 17.9 |
| 28 | 2 | Loop C | 126 | 378 | 2.7 |
| 29 | 2 | Loop C | 127 | 381 | 2.7 |
| 30 | 2 | TM4 | 132 | 394 | 2.7 |
| 31 | 2 | TM4 | 135 | 404 | 2.7 |
| 32 | 2 | TM4 | 136 | 407 | 7.1 |
| 33 | 2 | TM4 | 138 | 412 | 1.8 |
| 34 | 2 | TM4 | 140 | 419 | 2.7 |
| 35 | 2 | TM4 | 142 | 426 | 14.3 |
| 36 | 2 | TM4 | 144 | 431 | 2.7 |
| 37 | 2 | TM4 | 145 | 433 | 2.7 |
| 38 | 2 | TM4 | 146 | 436 | 14.3 |
| 39 | 2 | Loop D | 152 | 455 | 2.7 |
| 40 | 2 | Loop D | 154 | 460 | 2.7 |
| 41 | 2 | TM5 | 158 | 476 | 3.6 |
| 42 | 2 | TM5 | 163 | 488 | 2.7 |
| 43 | 2 | TM5 | 164 | 491 | 2.7 |
| 44 | 2 | TM5 | 166 | 498 | 2.7 |
| 45 | 2 | TM5 | 168 | 502 | 7.1 |
| 46 | 2 | TM5 | 169 | 506 | 2.7 |
| 47 | 2 | TM5 | 175 | 524 | 2.7 |
| 48 | 3 | Loop E | 179 | 535 | 3.6 |
| 49 | 3 | Loop E | 179 | 536 | 7.1 |
| 50 | 3 | Loop E | 181 | 543 | 2.7 |
| 51 | 3 | Loop E | 182 | 544 | 1.8 |
| 52 | 3 | Loop E | 184 | 551 | 2.7 |
| 53 | 3 | Loop E | 184 | 552 | 2.7 |
| 54 | 3 | Loop E | 185 | 553 | 1.8 |
| 55 | 3 | Loop E | 186 | 558 | 3.5 |
| 56 | 3 | Loop E | 187 | 562 | 3.5 |
| 57 | 3 | Loop E | 189 | 565 | 2.7 |
| 58 | 3 | Loop E | 189 | 567 | 14.3 |
| 59 | 3 | Loop E | 190 | 569 | 2.7 |
| 60 | 3 | Loop E | 191 | 573 | 7.1 |

The results of analysis of mutation of AQP5 cDNA from lung cancer tissues are summarized as follows:

First, mutations of AQP5 were characteristically found in multiple bases in each sample with a mean of 2.9 mutant bases per single cDNA sample from lung cancer tissue.

Second, mutations of AQP5 in lung cancer were widely scattered from one hundred sixty second base (after A of start codon) to five hundred seventy third base.

Third, mutational hot spots were identified. Mutation of AQP5 were particularly prevalent in loop B (codon number 62 to 86 or base number 184 to 258), loop C (codon number 110 to 130, base number 328 to 390), loop D (codon number 151 to 157 or base number 451-471), loop E (codon number 179-204, base number 535 to 612) and transmembrane domain™ between the loop, all of which are important area of water channel structure. About ninety percent of samples from lung cancer showed mutation in the above four areas, and in only ten percent of the sample, mutation was found outside of these four areas (See FIG. 15).

In addition, the inventors investigated mutation of AQP5 in samples of bronchoscopic lavage, sputum, malignant pleural fluid and blood from patients with lung cancer. On the analysis of cases in which cDNA of AQP5 was adequately amplified from the samples, AQP5 mutation was found in all of bronchoscopic lavage sample, 96.7% of sputum sample and all of blood samples, respectively (See FIGS. 13 and 14).

EXAMPLE 5

Test for Mutation of AQP5 in Lung Cancer Tissues, Lung Cancer Cell Lines, Samples of Bronchial Lavage, Sputum and Blood by using SSCP (Single Strand Conformational Polymorphism) Analysis.

The SSCP is based on the principles that single-stranded DNA has a tendency to fold up and form complex structures stabilized by intramolecular bonding, ie. base-paring hydrogen bonding and the electrophorectic mobilities of such structures on denaturing gel depend on not only on their chain lengths but also on their conformations, which are dictated by the DNA sequence, ie. even single base difference makes mobility shift. For SSCP, PCR or RT-PCR is performed using primers specific to mutation site and PCR products are loaded on a denaturing polyacrylamide gel electrophoresis, and after silver staining, mutation can be detected by observing mobility difference of a specific PCR product from the wild type pattern. SSCP is adequately sensitive for detecting mutation in DNA fragments up to 200-bp long.

SSCP for AQP5 were performed as follows: First, Exon 1, 2 and 3 of AQP5 were amplified by RT-PCR of RNA obtained from lung cancer tissues, lung cancer cell lines, and sample of bronchial lavage, sputum and blood from patients with lung cancer and normal controls. The sequences of oligonucleotide primers are as follows: sense primer for exon 1, SEQ ID NO:16; antisense primer for exon 1, SEQ ID NO: 17; sense primer for exon 2, SEQ ID NO: 18; antisense primer for exon 2, SEQ ID NO:19; sense primer for exon 3, SEQ ID NO: 20; antisense primer for exon 3, SEQ ID NO: 21. Each PCR was performed in 25 µl reaction mixture containing 50 ng of target DNA, 30 ng of each primer, 67 mM Tris-HCl (pH 8.8), 1 mM $MgCl_2$, 100 µM dNTP, 16 mM $(NH_4)_2SO_4$, 0.45% Triton-X 100, 200 mg/ml gelatin and 0.5 U Taq polymerase. After initial denaturation for 4 min at 94° C., the above reaction mixture was subjected to 35 cycles of amplification with 30s at 94° C., 1 min at 62° C., and 1 min at 72° C. The PCR products were mixed with deionized water to make 7 µl aliquot and then were mixed with 8 µl of loading buffer (0.5% dextran, 95% formamide). These mixtures were denatured by incubation for 3 min at 95° C., chilled on ice for 1 min, and then were loaded on 12% polyacrylamide gel electrophoresis.

After applying silver staining to the gel, mutant DNA samples were easily identified by difference in mobility from normal AQP5 cDNA (See FIG. 12).

EXAMPLE 6

Test for Mutation of AQP5 Gene by MSO (Mutant Specific Oligonucleotide)-Hybridization Method Mutant specific oligonucleotide (MSO) hybridization is a form of reverse blotting: Oligonucleotide probes for wild type gene and mutant type gene are immobilized on nitrocellulose or nylon filter (membrane), and this filter is hybridized with radio- or biotin-labelled PCR products. MSO hybridization distinguishes between wild type DNA and mutant type DNA by detecting difference in hybridization intensity.

The inventors modified classical method of MSO to make novel MSO method to test for mutation of AQP5, which were performed as follows:

1) Oligonucleotide probes were synthesized based on mutated sequences of AQP5 which were identified from lung cancer tissues as in EXAMPLE 4. These oligonucleotides were immobilized on nylon filters.

2) The exon 1, 2 and 3 of AQP5 were PCR-amplified in the same condition as in EXAMPLE 4, except that oligonucleotide primers were labeled by biotin at their 5' end.

3) The biotin-labeled PCR products of AQP5 we denatured and hybridized, with nylon membrane for 30 min at 58° C. The unbound DNA was removed by washing solution twice for 20 min. at RT and once for 10 min at 58° C.

4) The hybridized nylon membrane was incubated with streptavidin-labeled alkaline phosphatase for 30 min at RT and then was treated by BCIP/NBT chromogen, which induced color reaction. The presence or absence of mutation of AQP5 can be identified by observed color reaction at specific site. The results of MSO hybridization were comparatively analyzed with those of automated nucleic acid sequencing. On MSO hybridization of DNA samples which had been confirmed to carry mutation in two sites of AQP5, two bands with strong color reaction were found, which represented double mutation of AQP5 (See FIG. 17).

EXAMPLE 7

Test for Mutations of AQP5 Gene by ARMS (Amplification Refractory Mutation System or Allele-Specific Amplification) Method.

The ARMS method is based on the principle that mismatch between the 3' end of the primer and the template DNA will result in its inability during DNA amplification, ie. fail to produce product on PCR (Newton, C R et al. Analysis of any point mutant in DNA. The amplification refractory mutation system (ARMS). *Nucleic Acid Res* (1989) 17:2503-2561). With information on specified mutation, ARMS can distinguish between mutant type and wild type by specifically amplifying mutant or normal DNA by using set of primer specific to the normal sequence and mutant sequence. The ARMS for AQP5 was performed as follows:

First, five oligonucleotide primers were synthesized based on information on mutational hot spots of AQP5 in lung cancer which were acquired in EXAMPLE 4. PCR was performed in 50 µl reaction mixture (25 mM Tris-acetate (pH 7.8), 100 mM potassium acetate, 1 mM DTT), 5 µl of DMSO, 3 µl of 25 mM dNTP, 4 µl of 25 mM $MgCl_2$, 2.5 U of Taq polymerase (Promega), 50 ng of each target DNA and 12.5 pmol of each primer. After initial denaturation for 6 min at 94° C., reaction mixtures were subjected to 35 cycles of PCR with 30 sec at 94° C., 30 sec at 53° C., and 4 min at 65° C., followed by a final extension step of 7 min at 65° C. Presence of mutant DNA was identified by electrophoresis of PCR products on 2% Metaphor gel (FMC company, USA). Mutation of AQP5 gene was easily detected by observation of PCR products under mutant specific condition as compared with negative control sample (See FIG. 18).

EXAMPLE 8

Test for AQP5 Mutation by using DNA Chip (Hybridization Type Oligonucleotide Microarray)

The inventors had designed and produced hybridization type oligonucleotide chip which can scan all of the mutation of AQP5 as follows: First, we had designed and synthesized about 400 different types of oligonucleotide probes which were 20-bp long and contain not only wild type AQP sequence as well as sequences of all the mutant type AQP as were found in EXAMPLE 4 and listed in Table 5a and 5b. These probes were modified by attaching amine at their 5' end and were spotted onto silanated glass slide (Telechem, USA) with spotting buffer (2×SSC, pH 7.0). After spotting, slides were dried to stimulate binding of oligonucleotide probes, and were washed by 0.2% SDS for 2 min and then deionized water to remove unbound oligonucleotide probes. These slides were denatured by heating for 2 min at 95° C., and washed with blocking solution(1.0 g NaBH4, 300 ml of PBS (pH 7.4), ethanol 100 ml) for 15 min, 0.2% SDS solution for 1 min, and finally with deionized water for 2 min, and then were dried at room temperature to produce final oligonucleotide chip ready for use.

Next, fluorescence-labeled target DNA (AQP5 cDNA) was prepared as follows: 1 μl of RNA was prepared from each sample as mentioned in EXAMPLE 2, mixed with oligo d(T)15-mer primer and incubated for 5 min at 70° C., and for 5 min at 4° C. The reverse transcription (RT) reaction mixture was prepared by mixing the above mixture of RNA and oligo d(T) primer with 1 μl of 25 mM dATP, dGTP, dTTP, 1 μl of 1 mM dCTP (Roche, USA), 21 μl of 1 mM Cy3-dCTP or 1 μl of Cy5-dCTP(NEN), 20 U of RNase inhibitor (Roche), 100 U of M-MLV reverse transcriptase (Roche), and 2 μl of 10× first strand buffer in a total volume of 20μl. This RT reaction mixture was incubated for 2 hours at 38° C. Unbound nucleotides were removed by ethanol precipitation and then fluorescence-labeled cDNA of AQP were obtained.

Finally, hybridization reaction was performed on oligonucleotide chip and was analyzed by fluorescence scanner. Hybridization of the oligonucleotide DNA chip with fluorescence labeled cDNA fragments as prepared in the above was accomplished in UniHyb hybridization solution (TeleChem) for 4 hours at 42° C. The slides were washed twice with SSC solution for 5 min at RT, and air-dried. Then the slides were inserted into ScanArray 5000 fluorescence scanner (GSI Lumonics), scanned and scanning results were analyzed by ImaGene software (BioDiscovery, USA) (See FIG. 19).

EXAMPLE 9

Production of Sequencing Type Oligonucleotide Microarray and Testing for AQP5 Mutation by using this DNA Chip 1) Design and Production of Oligo Chip The oligonucleotide primers are designed so that each base in the AQP cDNA is analyzed by two unique 25-mer oligonucleotides, one for sense and one for antisensestrand. The oligonucleotide primers were designed depending on the wild type sequence of AQP5 cDNA with their 3' ends one base upstream of the base to be identified. These oligonucleotide primers are spotted (arrayed) onto chips and will react with cDNA or genomic DNA of AQP5 gene of the subject.

It is important to consider secondary structure or GC contents on design of oligonucleotide primers, because secondary structure or high GC content induce self-priming and interfere with annealing to the DNA sample. To prevent this, about 15% of oligonucleotide s required modification of internal base sequence. Oligonucleotides prepared in this way were tested by APEX reaction and scanning analysis. Oligonucleotide primers which did not work well required modification for 2 to 5 times. Finally the present inventors have established complete set of oligonucleotide primers (both sense and antisense) for AQP5, the sequences of which are listed in FIG. 20.

The oligonucleotide primers were modified by attaching chemical linker to their 5' ends. The linker is an amino linker with 12 carbon arm. This linker makes oligonucleotide primers to bind to glass surface firmly. Sequencing reaction (APEX reaction) occurs via 3' end of the oligonucleotide primers. The oligonucleotide primer with amino linkers at their 5' ends were purchased from MWG (Germany).

The raw material of DNA chip is microscopic glass slide which is 24×60 mm in size and 0.13-0.16 mm in thickness and were purchased from Menzel (Germany). To activate the slide surface for tight chemical binding of oligonucleotide primers, the slides were coated in advance before spotting as follows: Glass slides were washed in Alconox solution, sequentially washed and sonicated in deionized MilliQ water, acetone, MilliQ water, 2M NaOH/95% ethanol solution, MilliQ water, and acetone. Finally, the slides were was placed in 1% silane solution (380 ml of acetone, 16 ml of water, 3 ml of 3-aminopropyltrimethoxysilane), washed in aceton/95% ethanol, and dried. The slides were stored in 0.2% 1,4-phenylenediisothiocyanate/10% pyridine-dimethylformamide solution, rinsed in MeOH, acetone, and 95% ethanol, and were dried by centrifugation.

Oligonucleotide primers of AQP5 were spotted onto the glass slide prepared as above by using GMS-417 arrayer (GMS, USA). The process of spotting was performed depending on the guide of software of GMS 417.

The present method of design and production is just one of the examples. The design and manufacture of sequencing type oligonucleotide chip can be freely modified and supplemented.

2) Preparation of Samples

DNA and RNA were purified from patient's sample by conventional method and RNA was reverse transcribed into cDNA. Genomic DNA or cDNA of AQP5 were amplified by PCR as follows:

PCR was performed in 50 μl reaction mixture containing 5 μl of 10× reaction buffer, 5 μl of 25 mM MgCl$_2$, 5 μl of 2.5 mM dNTP (20% dUTP), 2 μl of each primer, 0.5 μl of cDNA, 1 μl of Taq DNA polymerase, and 29.5 μl of water. After initial denaturation for 5 min at 95° C., reaction mixtures were subjected to 2 cycle of PCR with 20 sec at 95° C., 30 sec at 64° C., for 30 sec at 72° C., respectively, followed by 30 cycles of PCR with 20 sec at 95° C., 30 sec at 58° C., 30 sec at 72° C., and 4 min at 65° C., followed by a final extension step of 7 min at 72° C.

Oligonucleotide primers for the above PCR were sense primer with SEQ ID NO: 22 for exon 1 and antisense primer with SEQ ID NO: 23 for exon 1, sense primer with SEQ ID NO: 24 for exon 2 and antisense primer with SEQ ID NO: 25 for exon 2, sense primer with SEQ ID NO: 26 for exon 3 and antisense primer with SEQ ID NO: 27 for exon 3, respectively.

PCR products were purified by conventional method including ammonium acetate/cold ethanol precipitation, ethanol treatment and centrifuge. Purified PCR products were fragmented to approximately 50-100 bp nucleotides in length as follows. PCR products were mixed with 0.5 □l Epicentre UNG (1 unit/l), 0.5 □l USB sAP (1 unit/l) and 2 □l 10× Epicentre buffer solution and this mixture was incubated for 1 hour at 37° C., and heated for 10 min at 95° C. Electrophoresis was performed to confirm appropriate fragmentation of PCR products.

3) APEX Reaction

Target DNA produced by PCR and fragmented as above were added onto oligonucleotide array on glass and APEX reaction was performed as follows. APEX reaction is a kind of Sanger's sequencing reaction.

APEX reaction was performed in a reaction mixture containing 5-10 μl of single stranded PCR product, 0.8 μl of 50M Texas-Red ddATP, 0.8 μl of 50M Cy3-ddCTP, 50M Cy5-ddUTP, 0.8 μl of 50M Fluorescein-ddGTP, and 150M Cy3-ddCTP, thermosequnase and 10× thermosequnase reaction buffer. The reaction mixture was denatured for 5 min at 95° C., added onto glass slide, covered by parafilm and incubated for 25 min at 58° C. Then parafilm was removed, slides were washed with boiling water, and were analyzed by fluorescence scanner.

4) Analysis of Nucleotide Sequences

The final step after APEX reaction is scanning analysis of nucleotide sequences of AQP5 from sample in oligo chip by using fluorescence scanner. Here, GENORAMA fluorescence DNA scanner (Asper, Estonia) was used, which is a 4-channel microarray fluorescence image system with 4 color lasers and CCD detector. The sequence of each base of AQP5 can be interpreted in an automated and quick way by using Genorama 3.0 genotyping software (Asper, Estonia), 5) Results About two hundred cDNA samples from a various type of human cancer and peripheral blood lymphocytes of normal population were comparatively analyzed by both oligonucleotide chip analysis and automated sequencing. The results of mutation test by using oligonucleotide chip concurred with those by automated sequencing in 98% of cases analyzed. In the remaining 2% of samples, oligonucleotide chip detected additional point mutation of AQP5, which were missed by automated sequencing analysis (See FIG. 21, 22, and 23).

INDUSTRIAL APPLICABILITY

As described hereinbefore, the method described in the present invention to detect AQP5 mutation including sequencing type oligonucleotide chips, is highly accurate, quick, easy and thus invaluable for cancer diagnosis.

The invention claimed is:

1. An oligonucleotide chip wherein the oligonucleotide sequences consisting of SEQ ID NOs: 28 through 929 are arrayed.

* * * * *

SEQUENCE LISTING

<160> NUMBER OF SEQ ID NOS: 27

<210> SEQ ID NO 1
<211> LENGTH: 798
<212> TYPE: DNA
<213> ORGANISM: Homo sapiens

<400> SEQUENCE: 1

```
atgaagaagg aggtgtgctc cgtggccttc ctcaaggccg tgttcgcaga gttcttggcc      60
accctcatct tcgtcttctt tggcctgggc tcggccctca agtggccgtc ggcgctgcct     120
accatcctgc agatcgcgct ggcgtttggc ctggccatag gcacgctggc ccaggccctg     180
ggacccgtga gcggcggcca catcaacccc gccatcaccc tggccctctt ggtgggcaac     240
cagatctcgc tgctccgggc tttcttctac gtggcggccc agctggtggg cgccattgcc     300
ggggctggca tcctctacgg tgtggcaccg ctcaatgccc ggggcaatct ggccgtcaac     360
gcgctcaaca acaacacaac gcagggccag gccatggtgg tggagctgat tctgaccttc     420
cagctggcac tctgcatctt cgcctccact gactcccgcc gcaccagccc tgtgggctcc     480
ccagccctgt ccattggcct gtctgtcacc ctgggccacc ttgtcggaat ctacttcact     540
ggctgctcca tgaacccagc ccgctctttt ggccctgcgg tggtcatgaa tcggttcagc     600
cccgctcact gggttttctg ggtagggccc atcgtgggg cggtcctggc tgccatcctt     660
tacttctacc tgctcttccc caactccctg agcctgagtg agcgtgtggc catcatcaaa     720
ggcacgtatg agcctgacga ggactgggag gagcagcggg aagagcggaa gaagaccatg     780
gagctgacca cccgctga                                                  798
```

<210> SEQ ID NO 2
<211> LENGTH: 21
<212> TYPE: DNA
<213> ORGANISM: Artificial Sequence
<220> FEATURE:

```
<223> OTHER INFORMATION: Forward primer for AQP1 cloning

<400> SEQUENCE: 2
atcgccacgc tggcgcagag t                                              21

<210> SEQ ID NO 3
<211> LENGTH: 21
<212> TYPE: DNA
<213> ORGANISM: Artificial Sequence
<220> FEATURE:
<223> OTHER INFORMATION: Backward primer for AQP1 cloning

<400> SEQUENCE: 3
cccgagttca caccatcagc c                                              21

<210> SEQ ID NO 4
<211> LENGTH: 20
<212> TYPE: DNA
<213> ORGANISM: Artificial Sequence
<220> FEATURE:
<223> OTHER INFORMATION: Forward primer for AQP3 cloning

<400> SEQUENCE: 4
atgggtcgac agaaggagct                                                20

<210> SEQ ID NO 5
<211> LENGTH: 20
<212> TYPE: DNA
<213> ORGANISM: Artificial Sequence
<220> FEATURE:
<223> OTHER INFORMATION: Backward primer for AQP3 cloning

<400> SEQUENCE: 5
tcagatctgc tccttgtgct                                                20

<210> SEQ ID NO 6
<211> LENGTH: 21
<212> TYPE: DNA
<213> ORGANISM: Artificial Sequence
<220> FEATURE:
<223> OTHER INFORMATION: Forward primer for AQP4 cloning

<400> SEQUENCE: 6
ccatggtgca gtgctttggc c                                              21

<210> SEQ ID NO 7
<211> LENGTH: 22
<212> TYPE: DNA
<213> ORGANISM: Artificial Sequence
<220> FEATURE:
<223> OTHER INFORMATION: Backward primer for AQP4 cloning

<400> SEQUENCE: 7
gaccagcggt aagatttcca tg                                             22

<210> SEQ ID NO 8
<211> LENGTH: 21
<212> TYPE: DNA
<213> ORGANISM: Artificial Sequence
<220> FEATURE:
<223> OTHER INFORMATION: Forward primer for AQP5 cloning

<400> SEQUENCE: 8
cgtttggcct ggccataggc a                                              21
```

<210> SEQ ID NO 9
<211> LENGTH: 21
<212> TYPE: DNA
<213> ORGANISM: Artificial Sequence
<220> FEATURE:
<223> OTHER INFORMATION: Backward primer for AQP5 cloning

<400> SEQUENCE: 9
tggccctgcg ttgtgttgtt g                                      21

<210> SEQ ID NO 10
<211> LENGTH: 23
<212> TYPE: DNA
<213> ORGANISM: Artificial Sequence
<220> FEATURE:
<223> OTHER INFORMATION: Forward primer for beta-actin cloning

<400> SEQUENCE: 10
acactgtgcc catctacgag ggg                                    23

<210> SEQ ID NO 11
<211> LENGTH: 29
<212> TYPE: DNA
<213> ORGANISM: Artificial Sequence
<220> FEATURE:
<223> OTHER INFORMATION: Backward primer for beta-actin cloning

<400> SEQUENCE: 11
atgatggagt tgaaggtagt ttcgtggat                              29

<210> SEQ ID NO 12
<211> LENGTH: 21
<212> TYPE: DNA
<213> ORGANISM: Artificial Sequence
<220> FEATURE:
<223> OTHER INFORMATION: Another forward primer for AQP5 cloning

<400> SEQUENCE: 12
cgtttggcct ggccataggc a                                      21

<210> SEQ ID NO 13
<211> LENGTH: 21
<212> TYPE: DNA
<213> ORGANISM: Artificial Sequence
<220> FEATURE:
<223> OTHER INFORMATION: Another backward primer for AQP5 cloning

<400> SEQUENCE: 13
tggccctgcg ttgtgttgtt g                                      21

<210> SEQ ID NO 14
<211> LENGTH: 21
<212> TYPE: DNA
<213> ORGANISM: Artificial Sequence
<220> FEATURE:
<223> OTHER INFORMATION: Forward primer for partial AQP5 cloning

<400> SEQUENCE: 14
cgtttggcct ggccataggc a                                      21

<210> SEQ ID NO 15
<211> LENGTH: 21
<212> TYPE: DNA
<213> ORGANISM: Artificial Sequence
<220> FEATURE:
<223> OTHER INFORMATION: Backward primer for partial AQP5 cloning

<400> SEQUENCE: 15
cgattcatga ccaccgcagg g                                    21

<210> SEQ ID NO 16
<211> LENGTH: 24
<212> TYPE: DNA
<213> ORGANISM: Artificial Sequence
<220> FEATURE:
<223> OTHER INFORMATION: Forward primer for cloning AQP5 exon 1

<400> SEQUENCE: 16
ggcgtttggc ctggccatag gcac                                 24

<210> SEQ ID NO 17
<211> LENGTH: 24
<212> TYPE: DNA
<213> ORGANISM: Artificial Sequence
<220> FEATURE:
<223> OTHER INFORMATION: Backward primer for cloning AQP5 exon 1

<400> SEQUENCE: 17
cggtgccaca ccgtagagga tgcc                                 24

<210> SEQ ID NO 18
<211> LENGTH: 24
<212> TYPE: DNA
<213> ORGANISM: Artificial Sequence
<220> FEATURE:
<223> OTHER INFORMATION: Forward primer for cloning of AQP5 exon 2

<400> SEQUENCE: 18
ggggcaatct ggccgtcaac gcgc                                 24

<210> SEQ ID NO 19
<211> LENGTH: 25
<212> TYPE: DNA
<213> ORGANISM: Artificial Sequence
<220> FEATURE:
<223> OTHER INFORMATION: Backward primer for cloning of AQP5 exon 2

<400> SEQUENCE: 19
ggtggcccca gggtgacaga caggc                                25

<210> SEQ ID NO 20
<211> LENGTH: 24
<212> TYPE: DNA
<213> ORGANISM: Artificial Sequence
<220> FEATURE:
<223> OTHER INFORMATION: Forward primer for cloning of AQP5 exon 3

<400> SEQUENCE: 20
gactcccgcc gcaccagccc tgtg                                 24

<210> SEQ ID NO 21
<211> LENGTH: 25
<212> TYPE: DNA
<213> ORGANISM: Artificial Sequence
<220> FEATURE:
<223> OTHER INFORMATION: Backward primer for cloning of AQP5 exon 3

<400> SEQUENCE: 21
ccctacccag aaaaccccag tgagc                                25

<210> SEQ ID NO 22
<211> LENGTH: 20

```
<212> TYPE: DNA
<213> ORGANISM: Artificial Sequence
<220> FEATURE:
<223> OTHER INFORMATION: Forward primer for pcr of AQP5 exon 1

<400> SEQUENCE: 22
gcggccacca tgaagaagga                                              20

<210> SEQ ID NO 23
<211> LENGTH: 20
<212> TYPE: DNA
<213> ORGANISM: Artificial Sequence
<220> FEATURE:
<223> OTHER INFORMATION: Backward primer for pcr of AQP5 exon 1

<400> SEQUENCE: 23
cccagggcac tcaccgcgtt                                              20

<210> SEQ ID NO 24
<211> LENGTH: 20
<212> TYPE: DNA
<213> ORGANISM: Artificial Sequence
<220> FEATURE:
<223> OTHER INFORMATION: Forward primer for pcr of AQP5 exon 2, 3

<400> SEQUENCE: 24
ctatcccctt gcagctcaac                                              20

<210> SEQ ID NO 25
<211> LENGTH: 20
<212> TYPE: DNA
<213> ORGANISM: Artificial Sequence
<220> FEATURE:
<223> OTHER INFORMATION: Backward primer for pcr of AQP5 exon 2, 3

<400> SEQUENCE: 25
agggacagac tcacccagtg                                              20

<210> SEQ ID NO 26
<211> LENGTH: 20
<212> TYPE: DNA
<213> ORGANISM: Artificial Sequence
<220> FEATURE:
<223> OTHER INFORMATION: Forward primer for pcr of AQP5 exon 1, 2, 3

<400> SEQUENCE: 26
ccaccctcat cttcgtcttc                                              20

<210> SEQ ID NO 27
<211> LENGTH: 19
<212> TYPE: DNA
<213> ORGANISM: Artificial Sequence
<220> FEATURE:
<223> OTHER INFORMATION: Backward primer for pcr of AQP5 exon 1, 2, 3

<400> SEQUENCE: 27
tgagcctgag tgagcgtgt                                               19
```